(12) United States Patent
Yang et al.

(10) Patent No.: US 7,867,491 B2
(45) Date of Patent: Jan. 11, 2011

(54) IMMUNOGLOBULIN FUSION PROTEINS

(75) Inventors: Sehwan Yang, Gyeongbuk (KR); Young Chul Sung, Pohang-si (KR)

(73) Assignees: Genexine Co., Ltd., Seoul (KR); Postech Academy-Industry Foundation of Pohang University of Science and Technology, Kyung-Buk (KR)

( * ) Notice: Subject to any disclaimer, the term of this patent is extended or adjusted under 35 U.S.C. 154(b) by 0 days.

(21) Appl. No.: 12/130,002

(22) Filed: May 30, 2008

(65) Prior Publication Data

US 2008/0300188 A1  Dec. 4, 2008

Related U.S. Application Data

(60) Provisional application No. 60/940,753, filed on May 30, 2007.

(51) Int. Cl.
  *A61K 39/395* (2006.01)
  *A61K 39/00* (2006.01)
  *C07K 16/00* (2006.01)
  *C12P 21/06* (2006.01)
  *C07H 21/04* (2006.01)

(52) U.S. Cl. ............. 424/130.1; 424/178.1; 424/192.1; 435/69.1; 530/387.1; 536/23.1

(58) Field of Classification Search .................. None
  See application file for complete search history.

(56) References Cited

PUBLICATIONS

Knauf et al., "Relationship of Effective Molecular Size to Systemic Clearance in Rats of Recombinant Interleukin-2 Chemically Modified with Water-Soluble Polymers," 1988, The Journal of Biological Chemistry, vol. 263, No. 29, pp. 15064-15070.

Riott et al., "Structural Variants of the Basic Immunoglobulin Molecule," Essential Immunology, 2001, 10th Edition, pp. 41 and 55.

Delgado et al., "The Uses and Properties of PEG-Linked Proteins," Critical Reviews in Therapeutic Drug Carrier Systems, 1992, vol. 9, Nos. 3 and 4, pp. 249-304.

Capon et al., "Designing CD4 Immunoadhesins for AIDS Therapy," Nature, 1989, vol. 337, pp. 525-531.

Paige et al., "Prolonged Circulation of Recombinant Human Granulocyte-Colony Stimulating Factor by Covalent Linkage to Albumin Through a Heterobifunctional Polyethylene Glycol," Pharmaceutical Research, 1995, vol. 12, No. 12, pp. 1883-1888.

Linsley et al., "Binding of the B Cell Activation Antigen B7 to CD28 Costimulates T Cell Proliferation and Interleukin 2 mRNA Accumulation," J. Exp. Med., 1991, vol. 173, pp. 721-730.

Mohler et al., "Soluble Tumor Necrosis Factor (TNF) Receptors Are Effective Therapeutic Agents in Lethal Endotoxemia and Function Simultaneously as Both TNF Carriers and TNF Antagonists," The Journal of Immunology, 1993, vol. 151, No. 3, pp. 1548-1561.

Morton et al., Differential Effects of CTLA-4 Substitutions on the Binding of Human CD80 (B7-1) and CD86 (B7-2), The American Association of Immunologists, 1996, pp. 1047-1054.

*Primary Examiner*—Lorraine Spector
*Assistant Examiner*—Elly-Gerald Stoica
(74) *Attorney, Agent, or Firm*—Sughrue Mion, PLLC

(57) ABSTRACT

Disclosed are fusion proteins comprising a biologically active molecule and an immunoglobulin (Ig) Fc domain which is linked to the biologically active molecule. The Fc domain is a hybrid human Fc domain of (i) IgG1, IgG2 or IgG4 or (ii) IgG4 and IgD. The hybrid Fc is useful as a carrier of biologically active molecules.

26 Claims, 18 Drawing Sheets

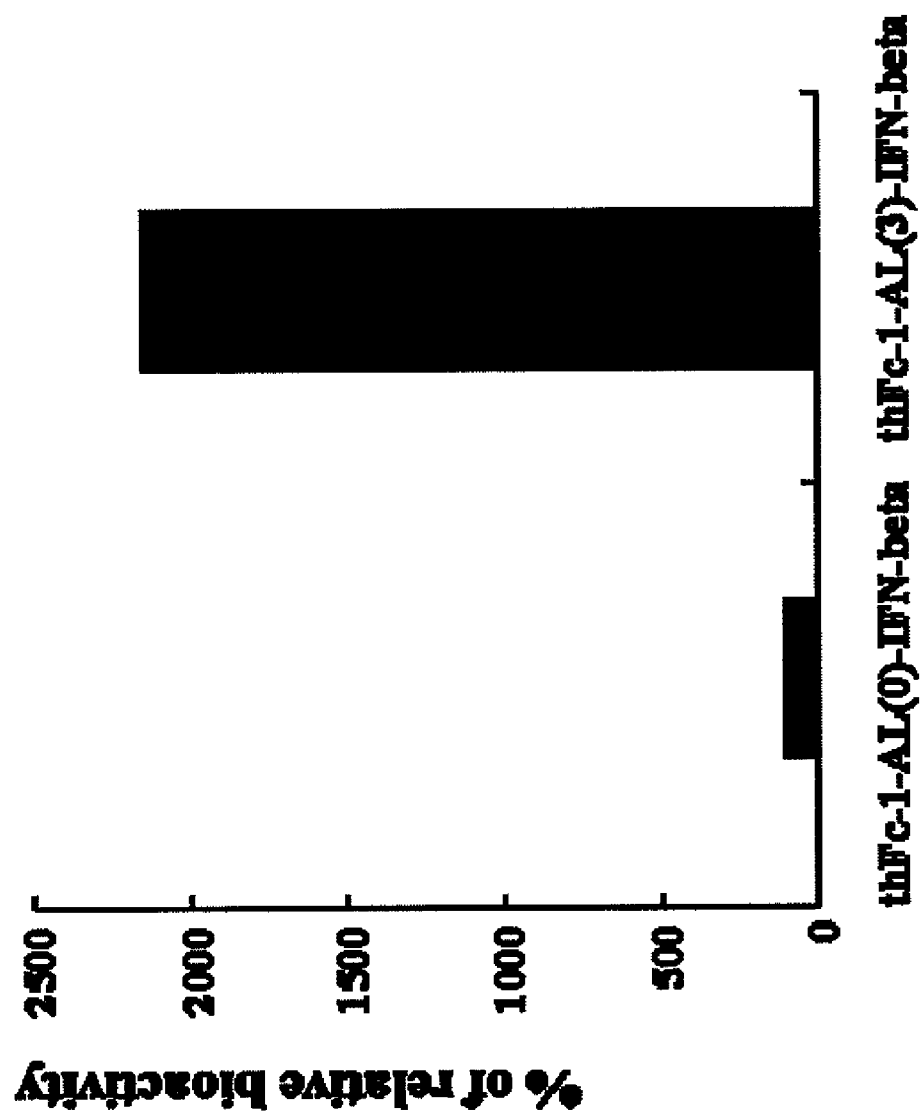

SEQUENCE LISTING

<160> NUMBER OF SEQ ID NOS: 32

<210> SEQ ID NO 1
<211> LENGTH: 720

```
<212> TYPE: DNA
<213> ORGANISM: Artificial Sequence
<220> FEATURE:
<223> OTHER INFORMATION: hybrid Fc fragment 1 (hFc-1)

<400> SEQUENCE: 1
agcaacacca aggtggacaa gagagtggaa cccaagagct gcgacaagac ccacacctgc     60
cctccctgcc ccgcccctcc cgtggccggc ccagcgtgt tcctgtttcc tcccaagccc    120
aaggataccc tgatgatctc cagaaccct gaggtgacct gcgtggtcgt ggatgtgagc    180
caggaagatc ccgaagtgca gttcaactgg tacgtggatg gcgtggaagt gcacaacgcc    240
aagaccaagc ccagagaaga gcagttcaac tccacctaca gagtggtgag cgtgctgacc    300
gtgctgcacc aggactggct gaacggcaag gagtacaagt gcaaggtgtc caacaaaggc    360
ctgcccagct ccatcgagaa gaccatcagc aaagccaaag ccagcccag agaacccag    420 gtgtacaccc tgcctcccag ccaggaagag atgaccaaga ccaggtgtc cctgacctgc    480 ctggtgaaag gcttctaccc cagcgacatc gccgtggagt gggaaagcaa cggccagccc    540
gagaacaatt acaagacaac ccctcccgtg ctggatagcg atggcagctt ctttctgtac    600
agcagactga ccgtggacaa gagcagatgg caggaaggca acgtgttcag ctgcagcgtg    660
atgcacgaag ccctgcacaa ccactacacc cagaagagcc tgtccctgag cctgggcaag    720

<210> SEQ ID NO 2
<211> LENGTH: 660
<212> TYPE: DNA
<213> ORGANISM: Artificial Sequence
<220> FEATURE:
<223> OTHER INFORMATION: hybrid Fc fragment 2 (hFC-2)

<400> SEQUENCE: 2 accccccgagt gccccagcca cacccagccc ctgggcgtgt tcctgttccc ccccaagccc    60
aaggacaccc tgatgatcag ccgcaccccc gaggtgacct gcgtggtcgt ggatgtgagc    120
caggaagatc ccgaagtgca gttcaactgg tacgtggatg gcgtggaagt gcacaacgcc    180
aagaccaagc ccagagaaga gcagttcaac tccacctaca gagtggtgag cgtgctgacc    240
gtgctgcacc aggactggct gaacggcaag gagtacaagt gcaaggtgtc caacaaaggc    300
ctgcccagct ccatcgagaa gaccatcagc aaagccaaag ccagcccag agaacccag    360 gtgtacaccc tgcctcccag ccaggaagag atgaccaaga ccaggtgtc cctgacctgc    420 ctggtgaaag gcttctaccc cagcgacatc gccgtggagt gggaaagcaa cggccagccc    480
gagaacaatt acaagacaac ccctcccgtg ctggatagcg atggcagctt ctttctgtac    540
agcagactga ccgtggacaa gagcagatgg caggaaggca acgtgttcag ctgcagcgtg    600
atgcacgaag ccctgcacaa ccactacacc cagaagagcc tgtccctgag cctgggcaag    660

<210> SEQ ID NO 3
<211> LENGTH: 675
<212> TYPE: DNA
<213> ORGANISM: Artificial Sequence
<220> FEATURE:
<223> OTHER INFORMATION: hybrid Fc fragment 3 (hFC-3)

<400> SEQUENCE: 3
gagcgcgaga ccaagacccc cgagtgcccc agccacaccc agccctgggg cgtgttcctg     60 ttcccccca gcccaagga caccctgatg atcagccgca ccccgaggt gacctgcgtg    120 gtcgtggatg tgagccagga agatcccgaa gtgcagttca ctggtacgt ggatggcgtg    180
```

```
gaagtgcaca acgccaagac caagcccaga gaagagcagt tcaactccac ctacagagtg    240
gtgagcgtgc tgaccgtgct gcaccaggac tggctgaacg gcaaggagta caagtgcaag    300
gtgtccaaca aaggcctgcc cagctccatc gagaagacca tcagcaaagc caaaggccag    360
cccagagaac ccaggtgta caccctgcct cccagccagg aagagatgac caagaaccag    420
gtgtccctga cctgcctggt gaaaggcttc taccccagcg acatcgccgt ggagtgggaa    480
agcaacggcc agcccgagaa caattacaag acaacccctc ccgtgctgga tagcgatggc    540
agcttctttc tgtacagcag actgaccgtg gacaagagca atggcagga aggcaacgtg    600 ttcagctgca gcgtgatgca cgaagccctg cacaaccact acacccagaa gagcctgtcc    660
ctgagcctgg gcaag                                                    675
```

```
<210> SEQ ID NO 4
<211> LENGTH: 705
<212> TYPE: DNA
<213> ORGANISM: Artificial Sequence
<220> FEATURE:
<223> OTHER INFORMATION: hybrid Fc fragment 4 (hFC-4)

<400> SEQUENCE: 4
aagaaggaga aggagaagga ggagcaggag gagcgcgaga ccaagacccc cgagtgcccc     60
agccacaccc agcccctggg cgtgttcctg ttccccccca gcccaagga caccctgatg    120 atcagccgca ccccgaggt gacctgcgtg gtcgtggatg tgagccagga agatcccgaa    180
gtgcagttca actggtacgt ggatggcgtg gaagtgcaca acgccaagac caagcccaga    240
gaagagcagt tcaactccac ctacagagtg gtgagcgtgc tgaccgtgct gcaccaggac    300
tggctgaacg gcaaggagta caagtgcaag gtgtccaaca aaggcctgcc cagctccatc    360
gagaagacca tcagcaaagc caaaggccag cccagagaac ccaggtgta caccctgcct    420 cccagccagg aagagatgac caagaaccag gtgtccctga cctgcctggt gaaaggcttc    480
taccccagcg acatcgccgt ggagtgggaa agcaacggcc agcccgagaa caattacaag    540
acaacccctc ccgtgctgga tagcgatggc agcttctttc tgtacagcag actgaccgtg    600
gacaagagca atggcagga aggcaacgtg ttcagctgca gcgtgatgca cgaagccctg    660
cacaaccact acacccagaa gagcctgtcc ctgagcctgg gcaag                   705
```

```
<210> SEQ ID NO 5
<211> LENGTH: 735
<212> TYPE: DNA
<213> ORGANISM: Artificial Sequence
<220> FEATURE:
<223> OTHER INFORMATION: hybrid Fc fragment 5 (hFC-5)

<400> SEQUENCE: 5
cgcaacaccg ccgcggcgg cgaggagaag aagaaggaga aggagaagga ggagcaggag     60
gagcgcgaga ccaagacccc cgagtgcccc agccacaccc agcccctggg cgtgttcctg    120
ttccccccca gcccaagga caccctgatg atcagccgca ccccgaggt gacctgcgtg    180 gtcgtggatg tgagccagga agatcccgaa gtgcagttca actggtacgt ggatggcgtg    240
gaagtgcaca acgccaagac caagcccaga gaagagcagt tcaactccac ctacagagtg    300
gtgagcgtgc tgaccgtgct gcaccaggac tggctgaacg gcaaggagta caagtgcaag    360
gtgtccaaca aaggcctgcc cagctccatc gagaagacca tcagcaaagc caaaggccag    420
cccagagaac ccaggtgta caccctgcct cccagccagg aagagatgac caagaaccag    480
gtgtccctga cctgcctggt gaaaggcttc taccccagcg acatcgccgt ggagtgggaa    540
```

-continued

```
agcaacggcc agcccgagaa caattacaag acaacccctc ccgtgctgga tagcgatggc    600
agcttctttc tgtacagcag actgaccgtg gacaagagca gatggcagga aggcaacgtg    660
ttcagctgca gcgtgatgca cgaagccctg cacaaccact acacccagaa gagcctgtcc    720
ctgagcctgg gcaag                                                    735
```

<210> SEQ ID NO 6
<211> LENGTH: 864
<212> TYPE: DNA
<213> ORGANISM: Artificial Sequence
<220> FEATURE:
<223> OTHER INFORMATION: hybrid Fc fragment 6 (hFc-6)

<400> SEQUENCE: 6

```
gctagcaaga gcaagaagga gatcttccgc tggcccgaga gccccaaggc ccaggccagc     60
agcgtgccca ccgcccagcc ccaggccgag ggcagcctgg ccaaggccac caccgccccc    120
gccaccaccc gcaacaccgg ccgcggcggc gaggagaaga gaaggagaa ggagaaggag     180 gagcaggagg agcgcgagac caagaccccc gagtgcccca gccacaccca gcccctgggc    240
gtgttcctgt tccccccaa gcccaaggac accctgatga tcagccgcac ccccgaggtg    300
acctgcgtgg tcgtggatgt gagccaggaa gatcccgaag tgcagttcaa ctggtacgtg    360
gatggcgtgg aagtgcacaa cgccaagacc aagcccagag aagagcagtt caactccacc    420
tacagagtgg tgagcgtgct gaccgtgctg caccaggact ggctgaacgg caaggagtac    480
aagtgcaagg tgtccaacaa aggcctgccc agctccatcg agaagaccat cagcaaagcc    540
aaaggccagc ccagagaacc ccaggtgtac accctgcctc ccagccagga agagatgacc    600
aagaaccagg tgtccctgac ctgcctggtg aaaggcttct accccagcga catcgccgtg    660
gagtgggaaa gcaacggcca gcccgagaac aattacaaga caacccctcc cgtgctggat    720
agcgatggca gcttctttct gtacagcaga ctgaccgtgg acaagagcag atggcaggaa    780
ggcaacgtgt tcagctgcag cgtgatgcac gaagccctgc acaaccacta cacccagaag    840
agcctgtccc tgagcctggg caag                                          864
```

<210> SEQ ID NO 7
<211> LENGTH: 579
<212> TYPE: DNA
<213> ORGANISM: artificial sequence
<220> FEATURE:
<223> OTHER INFORMATION: human EPO gene synthesized according to
      codon-optimization

<400> SEQUENCE: 7

```
atgggcgtgc acgagtgccc cgcctggctg tggctgctgc tgagcctgct gagcctgccc    60
ctgggcctgc ccgtgctggg cgccccccc cgcctgatct gcgacagccg cgtgctggag    120
cgctacctgc tggaggccaa ggaggccgag aacatcacca ccggctgcgc cgagcactgc    180
agcctgaacg agaacatcac cgtgcccgac accaaggtga acttctacgc ctggaagcgc    240
atggaggtgg gccagcaggc cgtggaggtg tggcagggcc tggccctgct gagcgaggcc    300
gtgctgcgcg gccaggccct gctggtgaac agcagccagc cctgggagcc cctgcagctg    360
cacgtggaca ggccgtgag cggcctgcgc agcctgacca ccctgctgcg cgccctgggc    420
gcccagaagg aggccatcag ccccccgac gccgcagcg ccgccccct gcgcaccatc    480 accgccgaca ccttccgcaa gctgttccgc gtgtacagca cttcctgcg cggcaagctg    540 aagctgtaca ccggcgaggc ctgccgcacc ggcgaccgc                          579
```

<210> SEQ ID NO 8
<211> LENGTH: 612
<212> TYPE: DNA
<213> ORGANISM: artificial sequence
<220> FEATURE:
<223> OTHER INFORMATION: human G-CSF gene synthesized according to
      codon-optimization

<400> SEQUENCE: 8

| | | | |
|---|---|---|---|
| atggccggcc ccgccaccca gagccccatg aagctgatgg ccctgcagct gctgctgtgg | | | 60 |
| cacagcgccc tgtggaccgt gcaggaggcc accccctgg ccccgccag cagcctgccc | | | 120 |
| cagagcttcc tgctgaagtg cctggagcag gtgcgcaaga tccagggcga cggcgccgcc | | | 180 |
| ctgcaggaga gctgtgcgc cacctacaag ctgtgccacc cgaggagct ggtgctgctg | | | 240 |
| ggccacagcc tgggcatccc ctgggcccc ctgagcagct gccccagcca ggccctgcag | | | 300 |
| ctggccggct gcctgagcca gctgcacagc ggcctgttcc tgtaccaggg cctgctgcag | | | 360 |
| gccctggagg gcatcagccc cgagctgggc ccacccctgg acaccctgca gctggacgtg | | | 420 |
| gccgacttcg ccaccaccat ctggcagcag atggaggagc tgggcatggc ccccgccctg | | | 480 |
| cagcccaccc agggcgccat gcccgccttc gccagcgcct tccagcgccg cgccggcggc | | | 540 |
| gtgctggtgg ccagccacct gcagagcttc ctggaggtga gctaccgcgt gctgcgccac | | | 600 |
| ctggcccagc cc | | | 612 |

<210> SEQ ID NO 9
<211> LENGTH: 984
<212> TYPE: DNA
<213> ORGANISM: Artificial Sequence
<220> FEATURE:
<223> OTHER INFORMATION: human p40 gene synthesized according to
      codon-optimization

<400> SEQUENCE: 9

| | | | |
|---|---|---|---|
| atgtgccacc agcagctggt gatcagctgg ttcagcctgg tgttcctggc cagccccctg | | | 60 |
| gtggccatct gggagctgaa gaaggacgtg tacgtggtgg agctggactg gtaccccgac | | | 120 |
| gcccccggcg agatggtggt gctgacctgc gacaccccg aggaggacgg catcacctgg | | | 180 |
| accctggacc agagcagcga ggtgctgggc agcggcaaga ccctgaccat ccaggtgaag | | | 240 |
| gagttcggcg acgccggcca gtacacctgc cacaagggcg gcgaggtgct gagccacagc | | | 300 |
| ctgctgctgc tgcacaagaa ggaggacggc atctggagca ccgacatcct gaaggaccag | | | 360 |
| aaggagccca gaacaagac cttcctgcgc tgcgaggcca gaactacag cggccgcttc | | | 420 |
| acctgctggt ggctgaccac catcagcacc gacctgacct tcagcgtgaa gagcagccgc | | | 480 |
| ggcagcagcg acccccaggg cgtgacctgc ggcgccgcca ccctgagcgc cgagcgcgtg | | | 540 |
| cgcggcgaca caaggagta cgagtacagc gtggagtgcc aggaggacag cgcctgcccc | | | 600 |
| gccgccgagg agagcctgcc catcgaggtg atggtggacg ccgtgcacaa gctgaagtac | | | 660 |
| gagaactaca ccagcagctt cttcatccgc gacatcatca gcccgaccc cccaagaac | | | 720 |
| ctgcagctga gcccctgaa gaacagccgc caggtggagg tgagctggga gtaccccgac | | | 780 |
| acctggagca ccccccacag ctacttcagc ctgaccttct gcgtgcaggt cagggcaag | | | 840 |
| agcaagcgcg agaagaagga ccgcgtgttc accgacaaga ccagcgccac cgtgatctgc | | | 900 |
| cgcaagcagg ccagcatcag cgtgcgcgcc caggaccgct actacagcag cagctggagc | | | 960 |
| gagtgggcca gcgtgccctg cagc | | | 984 |

<210> SEQ ID NO 10
<211> LENGTH: 5698
<212> TYPE: DNA
<213> ORGANISM: Artificial Sequence
<220> FEATURE:
<223> OTHER INFORMATION: pAD11

<400> SEQUENCE: 10

| | | | | | |
|---|---|---|---|---|---|
| gacggatcgg | gactagagca | ttgggggggg | ggacagctca | gggctgcgat | ttcgcgccaa | 60 |
| acttgacggc | aatcctagcg | tgaaggctgg | taggatttta | tccccgctgc | catcatggtt | 120 |
| cgaccattga | actgcatcgt | cgccgtgtcc | caaaatatgg | ggattggcaa | gaacggagac | 180 |
| ctaccctggc | ctccgctcag | gaacgagttc | aagtacttcc | aaagaatgac | cacaacctct | 240 |
| tcagtggaag | gtaaacagaa | tctggtgatt | atgggtagga | aaacctggtt | ctccattcct | 300 |
| gagaagaatc | gacctttaaa | ggacagaatt | aatatagttc | tcagtagaga | actcaaagaa | 360 |
| ccaccacgag | gagctcattt | tcttgccaaa | agtttggatg | atgccttaag | acttattgaa | 420 |
| caaccggaat | tggcaagtaa | agtagacatg | gtttggatag | tcggaggcag | ttctgtttac | 480 |
| caggaagcca | tgaatcaacc | aggccacctc | agactctttg | tgacaaggat | catgcaggaa | 540 |
| tttgaaagtg | acacgttttt | cccagaaatt | gatttgggga | aatataaact | tctcccagaa | 600 |
| tacccaggcg | tcctctctga | ggtccaggag | gaaaaaggca | tcaagtataa | gtttgaagtc | 660 |
| tacgagaaga | aagactaaca | ggaagatgct | ttcaagttct | ctgctcccct | cctaaagcta | 720 |
| tgcatttttta | taagaccatg | ggacttttgc | tggctttaga | tctttgtgaa | ggaaccttac | 780 |
| ttctgtggtg | tgacataatt | ggacaaacta | cctacagaga | tttaaagctc | taaggtaaat | 840 |
| ataaaatttt | taagtgtata | atgtgttaaa | ctactgattc | taattgtttg | tgtattttag | 900 |
| attccaacct | atggaactga | tgaatgggag | cagtggtgga | atgcctttaa | tgaggaaaac | 960 |
| ctgttttgct | cagaagaaat | gccatcagt | gatgatgagg | ctactgctga | ctctcaacat | 1020 |
| tctactcctc | caaaaaagaa | gagaaaggta | gaagacccca | aggactttcc | ttcagaattg | 1080 |
| ctaagttttt | tgagtcatgc | tgtgtttagt | aatagaactc | ttgcttgctt | tgctatttac | 1140 |
| accacaaagg | aaaaagctgc | actgctatac | aagaaaatta | tggaaaaata | ttctgtaacc | 1200 |
| tttataagta | ggcataacag | ttataatcat | aacatactgt | tttttcttac | tccacacagg | 1260 |
| catagagtgt | ctgctattaa | taactatgct | caaaaattgt | gtacctttag | cttttttaatt | 1320 |
| tgtaaagggg | ttaataagga | atatttgatg | tatagtgcct | tgactagaga | tcataatcag | 1380 |
| ccataccaca | tttgtagagg | ttttacttgc | tttaaaaaac | ctcccacacc | tccccctgaa | 1440 |
| cctgaaacat | aaaatgaatg | caattgttgt | tgttaacttg | tttattgcag | cttataatgg | 1500 |
| ttacaaataa | agcaatagca | tcacaaattt | cacaaataaa | gcatttttt | cactgcattc | 1560 |
| tagttgtggt | ttgtccaaac | tcatcaatgt | atcttatcat | gtctggatct | cccgatcccc | 1620 |
| tatggtgcac | tctcagtaca | atctgctctg | atgccgcata | gttaagccag | tatctgctcc | 1680 |
| ctgcttgtgt | gttggaggtc | gctgagtagt | gcgcgagcaa | aatttaagct | acaacaaggc | 1740 |
| aaggcttgac | cgacaattgc | atgaagaatc | tgcttagggt | taggcgtttt | gcgctgcttc | 1800 |
| gcgatgtacg | ggccagatat | acgcgttgac | attgattatt | gactagttat | taatagtaat | 1860 |
| caattacggg | gtcattagtt | catagcccat | atatggagtt | ccgcgttaca | taacttacgg | 1920 |
| taaatggccc | gcctggctga | ccgcccaacg | acccccgccc | attgacgtca | ataatgacgt | 1980 |
| atgttcccat | agtaacgcca | ataggggactt | tccattgacg | tcaatgggtg | gagtatttac | 2040 |
| ggtaaactgc | ccacttggca | gtacatcaag | tgtatcatat | gccaagtacg | ccccctattg | 2100 |

```
acgtcaatga cggtaaatgg cccgcctggc attatgccca gtacatgacc ttatgggact    2160
ttcctacttg gcagtacatc tacgtattag tcatcgctat taccatggtg atgcggtttt    2220
ggcagtacat caatgggcgt ggatagcggt ttgactcacg gggatttcca agtctccacc    2280
ccattgacgt caatgggagt ttgttttggc accaaaatca acgggacttt ccaaaatgtc    2340
gtaacaactc cgccccattg acgcaaatgg gcggtaggcg tgtacggtgg gaggtctata    2400
taagcagagc tctctggcta actagagaac ccactgctta ctggcttatc gaaattaata    2460
cgactcacta tagggagacc caagctggct agcgtgagtt tggggaccct tgattgttct    2520 ttcttttcg ctattgtaaa attcatgtta tatggagggg caaagtttt cagggtgttg     2580 tttagaacgg gaagatgtcc cttgtatcac catggaccct catgataatt ttgtttcttt    2640
cactttctac tctgttgaca accattgtct cctcttattt tcttttcatt ttctgtaact    2700
ttttcgttaa actttagctt gcatttgtaa cgaattttta aattcacttt tgtttatttg    2760
tcagattgta agtactttct ctaatcactt tttttcaag gcaatcaggg tatattatat      2820
tgtacttcag cacagtttta gagaacaatt gttataatta aatgataagg tagaatattt    2880
ctgcatataa attctggctg gcgtggaaat attcttattg gtagaaacaa ctacatcctg    2940
gtcatcatcc tgccttttct tttatggtta caatgatata cactgtttga gatgaggata    3000
aaatactctg agtccaaacc gggcccctct gctaaccatg ttcatgcctt cttcttttc     3060 ctacagctcc tgggcaacgt gctggttatt gtgctgtctc atcattttgg caaagaattg    3120
taatacgact cactataggg cgaattgaag cttggtaccg agctcggatc cactagtcca    3180
gtgtggtgga attcaccgcg gccgctctag agggccctat tctatagtgt cacctaaatg    3240
ctagagctcg ctgatcagcc tcgactgtgc cttctagttg ccagccatct gttgtttgcc    3300
cctcccccgt gccttccttg accctggaag gtgccactcc cactgtcctt tcctaataaa    3360
atgaggaaat tgcatcgcat tgtctgagta ggtgtcattc tattctgggg ggtggggtgg    3420
ggcaggacag caaggggag gattgggaag acaatagcag gcatgctggg gatgcggtgg     3480
gctctatggc ttctgaggcg gaaagaacca gctgggctc gagagcttgg cgtaatcatg     3540
gtcatagctg tttcctgtgt gaaattgtta tccgctcaca attccacaca atacgagc      3600 cggaagcata aagtgtaaag cctggggtgc ctaatgagtg agctaactca cattaattgc    3660
gttgcgctca ctgcccgctt tccagtcggg aaacctgtcg tgccagctgc attaatgaat    3720
cggccaacgc gcggggagag gcggtttgcg tattgggcgc tcttccgctt cctcgctcac    3780
tgactcgctg cgctcggtcg ttcggctgcg gcgagcggta tcagctcact caaaggcggt    3840
aatacggtta tccacagaat cagggataa cgcaggaaag aacatgtgag caaaaggcca     3900
gcaaaaggcc aggaaccgta aaaaggccgc gttgctggcg ttttccata ggctccgccc     3960 ccctgacgag catcacaaaa atcgacgctc aagtcagagg tggcgaaacc cgacaggact    4020
ataaagatac caggcgtttc ccctggaag ctccctcgtg cgctctcctg ttccgaccct     4080
gccgcttacc ggatacctgt ccgcctttct cccttcggga agcgtggcgc tttctcatag    4140
ctcacgctgt aggtatctca gttcggtgta ggtcgttcgc tccaagctgg gctgtgtgca    4200 cgaaccccc gttcagcccg accgctgcgc cttatccggt aactatcgtc ttgagtccaa     4260
cccggtaaga cacgacttat cgccactggc agcagccact ggtaacagga ttagcagagc    4320
gaggtatgta ggcggtgcta cagagttctt gaagtggtgg cctaactacg gctacactag    4380
aagaacagta tttggtatct gcgctctgct gaagccagtt accttcggaa aaagagttgg    4440
```

```
tagctcttga tccggcaaac aaaccaccgc tggtagcggt ggttttttg tttgcaagca    4500
gcagattacg cgcagaaaaa aaggatctca agaagatcct ttgatctttt ctacggggtc   4560
tgacgctcag tggaacgaaa actcacgtta agggattttg gtcatgagat tatcaaaaag   4620
gatcttcacc tagatccttt taaattaaaa atgaagtttt aaatcaatct aaagtatata   4680
tgagtaaact tggtctgaca gttaccaatg cttaatcagt gaggcaccta tctcagcgat   4740
ctgtctattt cgttcatcca tagttgcctg actccccgtc gtgtagataa ctacgatacg   4800
ggagggctta ccatctggcc ccagtgctgc aatgataccg cgagacccac gctcaccggc   4860
tccagattta tcagcaataa accagccagc cggaagggcc gagcgcagaa gtggtcctgc   4920
aactttatcc gcctccatcc agtctattaa ttgttgccgg gaagctagag taagtagttc   4980
gccagttaat agtttgcgca acgttgttgc cattgctaca ggcatcgtgg tgtcacgctc   5040
gtcgtttggt atggcttcat tcagctccgg ttcccaacga tcaaggcgag ttacatgatc   5100
ccccatgttg tgcaaaaaag cggttagctc cttcggtcct ccgatcgttg tcagaagtaa   5160
gttggccgca gtgttatcac tcatggttat ggcagcactg cataattctc ttactgtcat   5220
gccatccgta agatgctttt ctgtgactgg tgagtactca accaagtcat tctgagaata   5280
gtgtatgcgg cgaccgagtt gctcttgccc ggcgtcaata cgggataata ccgcgccaca   5340
tagcagaact ttaaaagtgc tcatcattgg aaaacgttct cgggggcgaa aactctcaag   5400
gatcttaccg ctgttgagat ccagttcgat gtaacccact cgtgcaccca actgatcttc   5460
agcatctttt actttcacca gcgtttctgg gtgagcaaaa acaggaaggc aaaatgccgc   5520
aaaaaaggga ataagggcga cacggaaatg ttgaatactc atactcttcc ttttcaata   5580
ttattgaagc atttatcagg gttattgtct catgagcgga tacatatttg aatgtattta   5640
gaaaaataaa caaataggg ttccgcgcac atttccccga aaagtgccac ctgacgtc     5698
```

```
<210> SEQ ID NO 11
<211> LENGTH: 330
<212> TYPE: PRT
<213> ORGANISM: Homo sapiens
<220> FEATURE:
<223> OTHER INFORMATION: partial human IgG1 constant region
      (Genbank accession No. CAA75032)

<400> SEQUENCE: 11
```

Ala Ser Phe Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

```
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 12
<211> LENGTH: 326
<212> TYPE: PRT
<213> ORGANISM: Homo sapiens
<220> FEATURE:
<223> OTHER INFORMATION: human IgG2 constant region(GenBank accesion
      No. CAC20455)

<400> SEQUENCE: 12

Ala Ser Phe Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
            85                  90                  95

Thr Val Glu Arg Lys Cys Cys Val Glu Cys Pro Pro Cys Pro Ala Pro
        100                 105                 110

Pro Val Ala Gly Pro Ser Val Phe Leu Phe Pro Pro Lys Pro Lys Asp
    115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
```

```
                165                 170                 175
Ser Thr Phe Cys Val Val Ser Val Leu Thr Val His Gln Asp Trp
            180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 13
<211> LENGTH: 327
<212> TYPE: PRT
<213> ORGANISM: Homo sapiens
<220> FEATURE:
<223> OTHER INFORMATION: Partial human IgG4 constant region
      (Genbank accession No. AAH25985)

<400> SEQUENCE: 13

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190
```

```
Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
        210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 14
<211> LENGTH: 383
<212> TYPE: PRT
<213> ORGANISM: Homo sapiens
<220> FEATURE:
<223> OTHER INFORMATION: human IgD constant region(Genbank accession
      No. P01880)

<400> SEQUENCE: 14

Ala Pro Thr Lys Ala Pro Asp Val Phe Pro Ile Ile Ser Gly Cys Arg
1               5                   10                  15

His Pro Lys Asp Asn Ser Pro Val Val Leu Ala Cys Leu Ile Thr Gly
            20                  25                  30

Tyr His Pro Thr Ser Val Thr Val Thr Trp Tyr Met Gly Thr Gln Ser
        35                  40                  45

Gln Pro Gln Arg Thr Phe Pro Glu Ile Gln Arg Arg Asp Ser Tyr Tyr
    50                  55                  60

Met Thr Ser Ser Gln Leu Ser Thr Pro Leu Gln Gln Trp Arg Gln Gly
65                  70                  75                  80

Glu Tyr Lys Cys Val Val Gln His Thr Ala Ser Lys Ser Lys Lys Glu
                85                  90                  95

Ile Phe Arg Trp Pro Glu Ser Pro Lys Ala Gln Ala Ser Ser Val Pro
            100                 105                 110

Thr Ala Gln Pro Gln Ala Glu Gly Ser Leu Ala Lys Ala Thr Thr Ala
        115                 120                 125

Pro Ala Thr Thr Arg Asn Thr Gly Arg Gly Gly Glu Glu Lys Lys Lys
    130                 135                 140

Glu Lys Glu Lys Glu Glu Gln Glu Glu Arg Glu Thr Lys Thr Pro Glu
145                 150                 155                 160

Cys Pro Ser His Thr Gln Pro Leu Gly Val Tyr Leu Leu Thr Pro Ala
                165                 170                 175

Val Gln Asp Leu Trp Leu Arg Asp Lys Ala Thr Phe Thr Cys Phe Val
            180                 185                 190

Val Gly Ser Asp Leu Lys Asp Ala His Leu Thr Trp Glu Val Ala Gly
        195                 200                 205

Lys Val Pro Thr Gly Gly Val Glu Glu Gly Leu Leu Glu Arg His Ser
    210                 215                 220
```

```
Asn Gly Ser Gln Ser Gln His Ser Arg Leu Thr Leu Pro Arg Ser Leu
225                 230                 235                 240

Trp Asn Ala Gly Thr Ser Val Thr Cys Thr Leu Asn His Pro Ser Leu
            245                 250                 255

Pro Pro Gln Arg Leu Met Ala Leu Arg Glu Pro Ala Ala Gln Ala Pro
        260                 265                 270

Val Lys Leu Ser Leu Asn Leu Leu Ala Ser Ser Asp Pro Pro Glu Ala
    275                 280                 285

Ala Ser Trp Leu Leu Cys Glu Val Ser Gly Phe Ser Pro Pro Asn Ile
290                 295                 300

Leu Leu Met Trp Leu Glu Asp Gln Arg Glu Val Asn Thr Ser Gly Phe
305                 310                 315                 320

Ala Pro Ala Arg Pro Pro Gln Pro Gly Ser Thr Thr Phe Trp Ala
            325                 330                 335

Trp Ser Val Leu Arg Val Pro Ala Pro Pro Ser Pro Gln Pro Ala Thr
            340                 345                 350

Tyr Thr Cys Val Val Ser His Glu Asp Ser Arg Thr Leu Leu Asn Ala
            355                 360                 365

Ser Arg Ser Leu Glu Val Ser Tyr Val Thr Asp His Gly Pro Met
370                 375                 380

<210> SEQ ID NO 15
<211> LENGTH: 193
<212> TYPE: PRT
<213> ORGANISM: Homo sapiens
<220> FEATURE:
<223> OTHER INFORMATION: human EPO precursor(Genbank accession No.
      NP_000790)

<400> SEQUENCE: 15

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg
```

<210> SEQ ID NO 16
<211> LENGTH: 207
<212> TYPE: PRT
<213> ORGANISM: Homo sapiens
<220> FEATURE:
<223> OTHER INFORMATION: human G-CSF(Genbank accession No. CAA27291)

<400> SEQUENCE: 16

Met Ala Gly Pro Ala Thr Gln Ser Pro Met Lys Leu Met Ala Leu Gln
 1               5                  10                  15

Leu Leu Leu Trp His Ser Ala Leu Trp Thr Val Gln Glu Ala Thr Pro
            20                  25                  30

Leu Gly Pro Ala Ser Ser Leu Pro Gln Ser Phe Leu Leu Lys Cys Leu
        35                  40                  45

Glu Gln Val Arg Lys Ile Gln Gly Asp Gly Ala Ala Leu Gln Glu Lys
    50                  55                  60

Leu Val Ser Glu Cys Ala Thr Tyr Lys Leu Cys His Pro Glu Glu Leu
65                  70                  75                  80

Val Leu Leu Gly His Ser Leu Gly Ile Pro Trp Ala Pro Leu Ser Ser
                85                  90                  95

Cys Pro Ser Gln Ala Leu Gln Leu Ala Gly Cys Leu Ser Gln Leu His
            100                 105                 110

Ser Gly Leu Phe Leu Tyr Gln Gly Leu Leu Gln Ala Leu Glu Gly Ile
        115                 120                 125

Ser Pro Glu Leu Gly Pro Thr Leu Asp Thr Leu Gln Leu Asp Val Ala
    130                 135                 140

Asp Phe Ala Thr Thr Ile Trp Gln Gln Met Glu Glu Leu Gly Met Ala
145                 150                 155                 160

Pro Ala Leu Gln Pro Thr Gln Gly Ala Met Pro Ala Phe Ala Ser Ala
                165                 170                 175

Phe Gln Arg Arg Ala Gly Gly Val Leu Val Ala Ser His Leu Gln Ser
            180                 185                 190

Phe Leu Glu Val Ser Tyr Arg Val Leu Arg His Leu Ala Gln Pro
        195                 200                 205

<210> SEQ ID NO 17
<211> LENGTH: 328
<212> TYPE: PRT
<213> ORGANISM: Homo sapiens
<220> FEATURE:
<223> OTHER INFORMATION: human IL12 p40 subunit(Genbank accession No.
      AAG32620)

<400> SEQUENCE: 17

Met Cys His Gln Gln Leu Val Ile Ser Trp Phe Ser Leu Val Phe Leu
 1               5                  10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

```
Leu Ser His Ser Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
115                 120                 125

Leu Arg Cys Glu Ala Lys Asn Tyr Ser Gly Arg Phe Thr Cys Trp Trp
            130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
    210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
    290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser
                325

<210> SEQ ID NO 18
<211> LENGTH: 240
<212> TYPE: PRT
<213> ORGANISM: Artificial Sequence
<220> FEATURE:
<223> OTHER INFORMATION: amino acid sequence of hFc-1

<400> SEQUENCE: 18

Ser Asn Thr Lys Val Asp Lys Arg Val Glu Pro Lys Ser Cys Asp Lys
1               5                   10                  15

Thr His Thr Cys Pro Pro Cys Pro Ala Pro Pro Val Ala Gly Pro Ser
            20                  25                  30

Val Phe Leu Phe Pro Pro Lys Pro Lys Asp Thr Leu Met Ile Ser Arg
        35                  40                  45

Thr Pro Glu Val Thr Cys Val Val Val Asp Val Ser Gln Glu Asp Pro
    50                  55                  60

Glu Val Gln Phe Asn Trp Tyr Val Asp Gly Val Glu Val His Asn Ala
65                  70                  75                  80

Lys Thr Lys Pro Arg Glu Glu Gln Phe Asn Ser Thr Tyr Arg Val Val
                85                  90                  95

Ser Val Leu Thr Val Leu His Gln Asp Trp Leu Asn Gly Lys Glu Tyr
            100                 105                 110

Lys Cys Lys Val Ser Asn Lys Gly Leu Pro Ser Ser Ile Glu Lys Thr
        115                 120                 125
```

```
Ile Ser Lys Ala Lys Gly Gln Pro Arg Glu Pro Gln Val Tyr Thr Leu
130                 135                 140

Pro Pro Ser Gln Glu Glu Met Thr Lys Asn Gln Val Ser Leu Thr Cys
145                 150                 155                 160

Leu Val Lys Gly Phe Tyr Pro Ser Asp Ile Ala Val Glu Trp Glu Ser
                165                 170                 175

Asn Gly Gln Pro Glu Asn Asn Tyr Lys Thr Thr Pro Val Leu Asp
                180                 185                 190

Ser Asp Gly Ser Phe Phe Leu Tyr Ser Arg Leu Thr Val Asp Lys Ser
                195                 200                 205

Arg Trp Gln Glu Gly Asn Val Phe Ser Cys Ser Val Met His Glu Ala
210                 215                 220

Leu His Asn His Tyr Thr Gln Lys Ser Leu Ser Leu Ser Leu Gly Lys
225                 230                 235                 240

<210> SEQ ID NO 19
<211> LENGTH: 220
<212> TYPE: PRT
<213> ORGANISM: Artificial Sequence
<220> FEATURE:
<223> OTHER INFORMATION: amino acid sequence of hFc-2

<400> SEQUENCE: 19

Thr Pro Glu Cys Pro Ser His Thr Gln Pro Leu Gly Val Phe Leu Phe
1               5                   10                  15

Pro Pro Lys Pro Lys Asp Thr Leu Met Ile Ser Arg Thr Pro Glu Val
                20                  25                  30

Thr Cys Val Val Val Asp Val Ser Gln Glu Asp Pro Glu Val Gln Phe
                35                  40                  45

Asn Trp Tyr Val Asp Gly Val Glu Val His Asn Ala Lys Thr Lys Pro
        50                  55                  60

Arg Glu Glu Gln Phe Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Gly Leu Pro Ser Ser Ile Glu Lys Thr Ile Ser Lys Ala
                100                 105                 110

Lys Gly Gln Pro Arg Glu Pro Gln Val Tyr Thr Leu Pro Pro Ser Gln
                115                 120                 125

Glu Glu Met Thr Lys Asn Gln Val Ser Leu Thr Cys Leu Val Lys Gly
130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Arg Leu Thr Val Asp Lys Ser Arg Trp Gln Glu
                180                 185                 190

Gly Asn Val Phe Ser Cys Ser Val Met His Glu Ala Leu His Asn His
                195                 200                 205

Tyr Thr Gln Lys Ser Leu Ser Leu Ser Leu Gly Lys
                210                 215                 220

<210> SEQ ID NO 20
<211> LENGTH: 225
<212> TYPE: PRT
<213> ORGANISM: Artificial Sequence
<220> FEATURE:
```

-continued

<223> OTHER INFORMATION: amino acid sequence of hFc-3

<400> SEQUENCE: 20

Glu Arg Glu Thr Lys Thr Pro Glu Cys Pro Ser His Thr Gln Pro Leu
1               5                   10                  15

Gly Val Phe Leu Phe Pro Pro Lys Pro Lys Asp Thr Leu Met Ile Ser
            20                  25                  30

Arg Thr Pro Glu Val Thr Cys Val Val Val Asp Val Ser Gln Glu Asp
        35                  40                  45

Pro Glu Val Gln Phe Asn Trp Tyr Val Asp Gly Val Glu Val His Asn
    50                  55                  60

Ala Lys Thr Lys Pro Arg Glu Glu Gln Phe Asn Ser Thr Tyr Arg Val
65              70                  75                  80

Val Ser Val Leu Thr Val Leu His Gln Asp Trp Leu Asn Gly Lys Glu
                85                  90                  95

Tyr Lys Cys Lys Val Ser Asn Lys Gly Leu Pro Ser Ser Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Gln Glu Glu Met Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Arg Leu Thr Val Asp Lys
            180                 185                 190

Ser Arg Trp Gln Glu Gly Asn Val Phe Ser Cys Ser Val Met His Glu
        195                 200                 205

Ala Leu His Asn His Tyr Thr Gln Lys Ser Leu Ser Leu Ser Leu Gly
    210                 215                 220

Lys
225

<210> SEQ ID NO 21
<211> LENGTH: 235
<212> TYPE: PRT
<213> ORGANISM: Artificial Sequence
<220> FEATURE:
<223> OTHER INFORMATION: amino acid sequence of hFc-4

<400> SEQUENCE: 21

Lys Lys Glu Lys Glu Lys Glu Glu Gln Glu Glu Arg Glu Thr Lys Thr
1               5                   10                  15

Pro Glu Cys Pro Ser His Thr Gln Pro Leu Gly Val Phe Leu Phe Pro
            20                  25                  30

Pro Lys Pro Lys Asp Thr Leu Met Ile Ser Arg Thr Pro Glu Val Thr
        35                  40                  45

Cys Val Val Val Asp Val Ser Gln Glu Asp Pro Glu Val Gln Phe Asn
    50                  55                  60

Trp Tyr Val Asp Gly Val Glu Val His Asn Ala Lys Thr Lys Pro Arg
65              70                  75                  80

Glu Glu Gln Phe Asn Ser Thr Tyr Arg Val Val Ser Val Leu Thr Val
                85                  90                  95

Leu His Gln Asp Trp Leu Asn Gly Lys Glu Tyr Lys Cys Lys Val Ser
            100                 105                 110

Asn Lys Gly Leu Pro Ser Ser Ile Glu Lys Thr Ile Ser Lys Ala Lys
            115                 120                 125

Gly Gln Pro Arg Glu Pro Gln Val Tyr Thr Leu Pro Pro Ser Gln Glu
        130                 135                 140

Glu Met Thr Lys Asn Gln Val Ser Leu Thr Cys Leu Val Lys Gly Phe
145                 150                 155                 160

Tyr Pro Ser Asp Ile Ala Val Glu Trp Glu Ser Asn Gly Gln Pro Glu
                165                 170                 175

Asn Asn Tyr Lys Thr Thr Pro Pro Val Leu Asp Ser Asp Gly Ser Phe
            180                 185                 190

Phe Leu Tyr Ser Arg Leu Thr Val Asp Lys Ser Arg Trp Gln Glu Gly
        195                 200                 205

Asn Val Phe Ser Cys Ser Val Met His Glu Ala Leu His Asn His Tyr
            210                 215                 220

Thr Gln Lys Ser Leu Ser Leu Ser Leu Gly Lys
225                 230                 235

<210> SEQ ID NO 22
<211> LENGTH: 245
<212> TYPE: PRT
<213> ORGANISM: Artificial Sequence
<220> FEATURE:
<223> OTHER INFORMATION: amino acid sequence of hFc-5

<400> SEQUENCE: 22

Arg Asn Thr Gly Arg Gly Gly Glu Glu Lys Lys Lys Glu Lys Glu Lys
1               5                   10                  15

Glu Glu Gln Glu Glu Arg Glu Thr Lys Thr Pro Glu Cys Pro Ser His
            20                  25                  30

Thr Gln Pro Leu Gly Val Phe Leu Phe Pro Pro Lys Pro Lys Asp Thr
        35                  40                  45

Leu Met Ile Ser Arg Thr Pro Glu Val Thr Cys Val Val Val Asp Val
    50                  55                  60

Ser Gln Glu Asp Pro Glu Val Gln Phe Asn Trp Tyr Val Asp Gly Val
65                  70                  75                  80

Glu Val His Asn Ala Lys Thr Lys Pro Arg Glu Glu Gln Phe Asn Ser
                85                  90                  95

Thr Tyr Arg Val Val Ser Val Leu Thr Val Leu His Gln Asp Trp Leu
            100                 105                 110

Asn Gly Lys Glu Tyr Lys Cys Lys Val Ser Asn Lys Gly Leu Pro Ser
        115                 120                 125

Ser Ile Glu Lys Thr Ile Ser Lys Ala Lys Gly Gln Pro Arg Glu Pro
    130                 135                 140

Gln Val Tyr Thr Leu Pro Pro Ser Gln Glu Glu Met Thr Lys Asn Gln
145                 150                 155                 160

Val Ser Leu Thr Cys Leu Val Lys Gly Phe Tyr Pro Ser Asp Ile Ala
                165                 170                 175

Val Glu Trp Glu Ser Asn Gly Gln Pro Glu Asn Asn Tyr Lys Thr Thr
            180                 185                 190

Pro Pro Val Leu Asp Ser Asp Gly Ser Phe Phe Leu Tyr Ser Arg Leu
        195                 200                 205

Thr Val Asp Lys Ser Arg Trp Gln Glu Gly Asn Val Phe Ser Cys Ser
    210                 215                 220

Val Met His Glu Ala Leu His Asn His Tyr Thr Gln Lys Ser Leu Ser
225                 230                 235                 240

```
Leu Ser Leu Gly Lys
            245
```

<210> SEQ ID NO 23
<211> LENGTH: 288
<212> TYPE: PRT
<213> ORGANISM: Artificial Sequence
<220> FEATURE:
<223> OTHER INFORMATION: amino acid sequence of hFc-6

<400> SEQUENCE: 23

```
Ala Ser Lys Ser Lys Lys Glu Ile Phe Arg Trp Pro Glu Ser Pro Lys
 1               5                  10                  15

Ala Gln Ala Ser Ser Val Pro Thr Ala Gln Pro Gln Ala Glu Gly Ser
            20                  25                  30

Leu Ala Lys Ala Thr Thr Ala Pro Ala Thr Thr Arg Asn Thr Gly Arg
        35                  40                  45

Gly Gly Glu Glu Lys Lys Lys Glu Lys Glu Lys Glu Glu Gln Glu Glu
    50                  55                  60

Arg Glu Thr Lys Thr Pro Glu Cys Pro Ser His Thr Gln Pro Leu Gly
65                  70                  75                  80

Val Phe Leu Phe Pro Pro Lys Pro Lys Asp Thr Leu Met Ile Ser Arg
                85                  90                  95

Thr Pro Glu Val Thr Cys Val Val Asp Val Ser Gln Glu Asp Pro
            100                 105                 110

Glu Val Gln Phe Asn Trp Tyr Val Asp Gly Val Glu Val His Asn Ala
        115                 120                 125

Lys Thr Lys Pro Arg Glu Glu Gln Phe Asn Ser Thr Tyr Arg Val Val
    130                 135                 140

Ser Val Leu Thr Val Leu His Gln Asp Trp Leu Asn Gly Lys Glu Tyr
145                 150                 155                 160

Lys Cys Lys Val Ser Asn Lys Gly Leu Pro Ser Ser Ile Glu Lys Thr
                165                 170                 175

Ile Ser Lys Ala Lys Gly Gln Pro Arg Glu Pro Gln Val Tyr Thr Leu
            180                 185                 190

Pro Pro Ser Gln Glu Glu Met Thr Lys Asn Gln Val Ser Leu Thr Cys
        195                 200                 205

Leu Val Lys Gly Phe Tyr Pro Ser Asp Ile Ala Val Glu Trp Glu Ser
    210                 215                 220

Asn Gly Gln Pro Glu Asn Asn Tyr Lys Thr Thr Pro Pro Val Leu Asp
225                 230                 235                 240

Ser Asp Gly Ser Phe Phe Leu Tyr Ser Arg Leu Thr Val Asp Lys Ser
                245                 250                 255

Arg Trp Gln Glu Gly Asn Val Phe Ser Cys Ser Val Met His Glu Ala
            260                 265                 270

Leu His Asn His Tyr Thr Gln Lys Ser Leu Ser Leu Ser Leu Gly Lys
        275                 280                 285
```

<210> SEQ ID NO 24
<211> LENGTH: 377
<212> TYPE: PRT
<213> ORGANISM: Homo sapiens
<220> FEATURE:
<223> OTHER INFORMATION: human IgG3 constant region(Genbank accession
      No. CAC20456)

<400> SEQUENCE: 24

```
Ala Ser Phe Lys Gly Pro Ser Val Phe Pro Leu Ala Pro Cys Ser Arg
  1               5                  10                  15

Ser Thr Pro Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
 65                  70                  75                  80

Tyr Thr Cys Asn Val Asn His Lys Pro Ser Asn Thr Lys Val Asp Lys
                 85                  90                  95

Arg Val Glu Leu Lys Thr Pro Leu Gly Asp Thr Thr His Thr Cys Pro
             100                 105                 110

Arg Cys Pro Glu Pro Lys Ser Cys Asp Thr Pro Pro Cys Pro Arg
         115                 120                 125

Cys Pro Glu Pro Lys Ser Cys Asp Thr Pro Pro Cys Pro Arg Cys
130                 135                 140

Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Pro Lys
             165                 170                 175

Pro Lys Asp Thr Leu Met Ile Ser Arg Thr Pro Glu Val Thr Cys Val
             180                 185                 190

Val Val Asp Val Ser His Glu Asp Pro Glu Val Gln Phe Lys Trp Tyr
         195                 200                 205

Val Asp Gly Val Glu Val His Asn Ala Lys Thr Lys Pro Arg Glu Glu
210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
             245                 250                 255

Ala Leu Pro Ala Pro Ile Glu Lys Thr Ile Ser Lys Thr Lys Gly Gln
         260                 265                 270

Pro Arg Glu Pro Gln Val Tyr Thr Leu Pro Pro Ser Arg Glu Glu Met
     275                 280                 285

Thr Lys Asn Gln Val Ser Leu Thr Cys Pro Val Lys Gly Phe Tyr Pro
290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
             325                 330                 335

Tyr Ser Lys Leu Thr Val Asp Lys Ser Arg Trp Gln Gln Gly Asn Ile
         340                 345                 350

Phe Ser Cys Ser Val Met His Glu Ala Leu His Asn Arg Phe Thr Gln
     355                 360                 365

Lys Ser Leu Ser Leu Ser Pro Gly Lys
370                 375

<210> SEQ ID NO 25
<211> LENGTH: 609
<212> TYPE: PRT
<213> ORGANISM: Homo sapiens
<220> FEATURE:
<223> OTHER INFORMATION: human albumin(Genbank accession No. CAA00606)
```

```
<400> SEQUENCE: 25

Met Lys Trp Val Thr Phe Ile Ser Leu Leu Phe Leu Phe Ser Ser Ala
 1               5                  10                  15

Tyr Ser Arg Gly Val Phe Arg Arg Asp Ala His Lys Ser Glu Val Ala
             20                  25                  30

His Arg Phe Lys Asp Leu Gly Glu Glu Asn Phe Lys Ala Leu Val Leu
         35                  40                  45

Ile Ala Phe Ala Gln Tyr Leu Gln Gln Cys Pro Phe Glu Asp His Val
     50                  55                  60

Lys Leu Val Asn Glu Val Thr Glu Phe Ala Lys Thr Cys Val Ala Asp
 65                  70                  75                  80

Glu Ser Ala Glu Asn Cys Asp Lys Ser Leu His Thr Leu Phe Gly Asp
                 85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
    130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
    210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
        275                 280                 285

Cys Glu Asn Gln Asp Ser Ile Ser Ser Lys Leu Lys Glu Cys Cys Glu
    290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
            340                 345                 350

Met Phe Leu Tyr Glu Tyr Ala Arg Arg His Pro Asp Tyr Ser Val Val
        355                 360                 365

Leu Leu Leu Arg Leu Ala Lys Thr Tyr Glu Thr Thr Leu Glu Lys Cys
    370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
```

```
                405                 410                 415
Glu Leu Phe Glu Gln Leu Gly Glu Tyr Lys Phe Gln Asn Ala Leu Leu
            420                 425                 430

Val Arg Tyr Thr Lys Lys Val Pro Gln Val Ser Thr Pro Thr Leu Val
            435                 440                 445

Glu Val Ser Arg Asn Leu Gly Lys Val Gly Ser Lys Cys Cys Lys His
        450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
                485                 490                 495

Val Thr Lys Cys Cys Thr Glu Ser Leu Val Asn Arg Arg Pro Cys Phe
            500                 505                 510

Ser Ala Leu Glu Val Asp Glu Thr Tyr Val Pro Lys Glu Phe Asn Ala
            515                 520                 525

Glu Thr Phe Thr Phe His Ala Asp Ile Cys Thr Leu Ser Glu Lys Glu
        530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
            580                 585                 590

Ala Glu Glu Gly Lys Lys Leu Val Ala Ala Ser Gln Ala Ala Leu Gly
            595                 600                 605

Leu

<210> SEQ ID NO 26
<211> LENGTH: 762
<212> TYPE: DNA
<213> ORGANISM: Artificial Sequence
<220> FEATURE:
<223> OTHER INFORMATION: hybrid Fc fragment 1 (thFc-1)

<400> SEQUENCE: 26
atggatgcca tgctgagagg cctgtgctgc gtgctgctgc tgtgcggcgc cgtgttcgtg      60
agcccctccg aacccaagag ctgcgacaag acccacacct gccctccctg ccccgcccct     120
cccgtggccg cccccagcgt gttcctgttt cctcccaagc ccaaggatac cctgatgatc     180
tccagaaccc ctgaggtgac ctgcgtggtc gtggatgtga gccaggaaga tcccgaagtg     240
cagttcaact ggtacgtgga tggcgtggaa gtgcacaacg ccaagaccaa gccagagaa      300 gagcagttca actccaccta cagagtggtg agcgtgctga ccgtgctgca ccaggactgg     360
ctgaacggca aggagtacaa gtgcaaggtg tccaacaaag gcctgccag ctccatcgag      420 aagaccatca gcaaagccaa aggccagccc agagaacccc aggtgtacac cctgcctccc     480
agccaggaag agatgaccaa gaaccaggtg tccctgacct gcctggtgaa aggcttctac     540
cccagcgaca tcgccgtgga gtgggaaagc aacggccagc ccgagaacaa ttacaagaca     600
acccctcccg tgctggatag cgatggcagc ttctttctgt acagcagact gaccgtggac     660
aagagcagat ggcaggaagg caacgtgttc agctgcagcg tgatgcacga agccctgcac     720
aaccactaca cccagaagag cctgtccctg agcctgggat cc                        762

<210> SEQ ID NO 27
<211> LENGTH: 759
```

```
<212> TYPE: DNA
<213> ORGANISM: Artificial Sequence
<220> FEATURE:
<223> OTHER INFORMATION: hybrid Fc fragment 2 (thFc-2)

<400> SEQUENCE: 27
atggatgcca tgctgagagg cctgtgctgc gtgctgctgc tgtgcggcgc cgtgttcgtg      60
agcccctcca aggaggagca ggaggagcgc gagaccaaga cccccgagtg ccccagccac     120
acccagcccc tgggcgtgtt cctgttcccc cccaagccca aggacaccct gatgatcagc     180
cgcacccccg aggtgacctg cgtggtcgtg gatgtgagcc aggaagatcc cgaagtgcag     240
ttcaactggt acgtggatgg cgtggaagtg cacaacgcca gaccaagcc cagagaagag     300
cagttcaact ccacctacag agtggtgagc gtgctgaccg tgctgcacca ggactggctg     360
aacggcaagg agtacaagtg caaggtgtcc aacaaaggcc tgcccagctc catcgagaag     420
accatcagca agccaaagg ccagcccaga gaacccagg tgtacaccct gcctcccagc      480
caggaagaga tgaccaagaa ccaggtgtcc ctgacctgcc tggtgaaagg cttctacccc     540
agcgacatcg ccgtggagtg ggaaagcaac ggccagcccg agaacaatta caagacaacc     600
cctcccgtgc tggatagcga tggcagcttc tttctgtaca gcagactgac cgtggacaag     660
agcagatggc aggaaggcaa cgtgttcagc tgcagcgtga tgcacgaagc cctgcacaac     720
cactacaccc agaagagcct gtccctgagc ctgggcaag                            759

<210> SEQ ID NO 28
<211> LENGTH: 254
<212> TYPE: PRT
<213> ORGANISM: Artificial Sequence
<220> FEATURE:
<223> OTHER INFORMATION: amino acid sequence of thFc-1

<400> SEQUENCE: 28

Met Asp Ala Met Leu Arg Gly Leu Cys Cys Val Leu Leu Leu Cys Gly
  1               5                  10                  15

Ala Val Phe Val Ser Pro Ser Glu Pro Lys Ser Cys Asp Lys Thr His
                 20                  25                  30

Thr Cys Pro Pro Cys Pro Ala Pro Val Ala Gly Pro Ser Val Phe
             35                  40                  45

Leu Phe Pro Pro Lys Pro Lys Asp Thr Leu Met Ile Ser Arg Thr Pro
         50                  55                  60

Glu Val Thr Cys Val Val Val Asp Val Ser Gln Glu Asp Pro Glu Val
 65                  70                  75                  80

Gln Phe Asn Trp Tyr Val Asp Gly Val Glu Val His Asn Ala Lys Thr
                 85                  90                  95

Lys Pro Arg Glu Glu Gln Phe Asn Ser Thr Tyr Arg Val Val Ser Val
                100                 105                 110

Leu Thr Val Leu His Gln Asp Trp Leu Asn Gly Lys Glu Tyr Lys Cys
            115                 120                 125

Lys Val Ser Asn Lys Gly Leu Pro Ser Ser Ile Glu Lys Thr Ile Ser
        130                 135                 140

Lys Ala Lys Gly Gln Pro Arg Glu Pro Gln Val Tyr Thr Leu Pro Pro
145                 150                 155                 160

Ser Gln Glu Glu Met Thr Lys Asn Gln Val Ser Leu Thr Cys Leu Val
                165                 170                 175

Lys Gly Phe Tyr Pro Ser Asp Ile Ala Val Glu Trp Glu Ser Asn Gly
            180                 185                 190
```

```
Gln Pro Glu Asn Asn Tyr Lys Thr Thr Pro Val Leu Asp Ser Asp
            195                 200                 205

Gly Ser Phe Phe Leu Tyr Ser Arg Leu Thr Val Asp Lys Ser Arg Trp
    210                 215                 220

Gln Glu Gly Asn Val Phe Ser Cys Ser Val Met His Glu Ala Leu His
225                 230                 235                 240

Asn His Tyr Thr Gln Lys Ser Leu Ser Leu Ser Leu Gly Ser
            245                 250
```

<210> SEQ ID NO 29
<211> LENGTH: 253
<212> TYPE: PRT
<213> ORGANISM: Artificial Sequence
<220> FEATURE:
<223> OTHER INFORMATION: amino acid sequence of thFc-2

<400> SEQUENCE: 29

```
Met Asp Ala Met Leu Arg Gly Leu Cys Cys Val Leu Leu Cys Gly
 1               5                  10                  15

Ala Val Phe Val Ser Pro Ser Lys Glu Glu Gln Glu Glu Arg Glu Thr
                 20                  25                  30

Lys Thr Pro Glu Cys Pro Ser His Thr Gln Pro Leu Gly Val Phe Leu
            35                  40                  45

Phe Pro Pro Lys Pro Lys Asp Thr Leu Met Ile Ser Arg Thr Pro Glu
 50                  55                  60

Val Thr Cys Val Val Val Asp Val Ser Gln Glu Asp Pro Glu Val Gln
65                  70                  75                  80

Phe Asn Trp Tyr Val Asp Gly Val Glu Val His Asn Ala Lys Thr Lys
                85                  90                  95

Pro Arg Glu Glu Gln Phe Asn Ser Thr Tyr Arg Val Val Ser Val Leu
            100                 105                 110

Thr Val Leu His Gln Asp Trp Leu Asn Gly Lys Glu Tyr Lys Cys Lys
        115                 120                 125

Val Ser Asn Lys Gly Leu Pro Ser Ser Ile Glu Lys Thr Ile Ser Lys
    130                 135                 140

Ala Lys Gly Gln Pro Arg Glu Pro Gln Val Tyr Thr Leu Pro Pro Ser
145                 150                 155                 160

Gln Glu Glu Met Thr Lys Asn Gln Val Ser Leu Thr Cys Leu Val Lys
                165                 170                 175

Gly Phe Tyr Pro Ser Asp Ile Ala Val Glu Trp Glu Ser Asn Gly Gln
            180                 185                 190

Pro Glu Asn Asn Tyr Lys Thr Thr Pro Val Leu Asp Ser Asp Gly
        195                 200                 205

Ser Phe Phe Leu Tyr Ser Arg Leu Thr Val Asp Lys Ser Arg Trp Gln
    210                 215                 220

Glu Gly Asn Val Phe Ser Cys Ser Val Met His Glu Ala Leu His Asn
225                 230                 235                 240

His Tyr Thr Gln Lys Ser Leu Ser Leu Ser Leu Gly Lys
                245                 250
```

<210> SEQ ID NO 30
<211> LENGTH: 771
<212> TYPE: DNA
<213> ORGANISM: artificial sequence
<220> FEATURE:
<223> OTHER INFORMATION: human soluble TNF receptor 2 gene synthesized
      according to codon-optimization

<400> SEQUENCE: 30

```
atggctcccg tggccgtgtg ggccgctctg ccgtgggcc tggagctgtg ggccgctgcc    60
cacgccctgc ctgcccaggt ggcctttaca ccctatgctc ccgagcccgg cagcacctgc   120
agactgagag agtactacga ccagacagcc agatgtgtt gcagcaagtg cagccccggc   180
cagcacgcca aggtgttctg caccaagacc agcgacaccg tgtgtgacag ctgcgaggac   240
agcacctaca cccagctgtg gaactgggtg cccgagtgcc tgagctgtgg cagcagatgc   300
agctccgacc aggtggagac ccaggcctgc accagagagc agaatagaat ctgcacctgc   360
agacctggct ggtactgtgc cctgagcaag caggagggct gcagactgtg tgcccctctg   420
agaaagtgca gacctggctt tggcgtggcc agacccggca ccgagaccag cgacgtggtg   480
tgcaaaccct gtgcccctgg caccttcagc aacaccacat ccagcaccga catctgcaga   540
ccccaccaga tctgcaacgt ggtggccatt cccggcaatg ccagcatgga tgccgtgtgc   600
accagcacca gccccaccag aagcatggcc cctggcgccg tgcacctgcc ccagcccgtg   660
agcaccagaa gccagcacac ccagcccaca cccgagccca gcacagcccc tagcaccagc   720
ttcctgctgc ccatgggccc cagccctcct gccgagggca gcacaggcga t           771
```

<210> SEQ ID NO 31
<211> LENGTH: 257
<212> TYPE: PRT
<213> ORGANISM: artificial sequence
<220> FEATURE:
<223> OTHER INFORMATION: human soluble TNF receptor 2 encoded by gene synthesized according to codon-optimization

<400> SEQUENCE: 31

```
Met Ala Pro Val Ala Val Trp Ala Ala Leu Ala Val Gly Leu Glu Leu
 1               5                  10                  15

Trp Ala Ala Ala His Ala Leu Pro Ala Gln Val Ala Phe Thr Pro Tyr
            20                  25                  30

Ala Pro Glu Pro Gly Ser Thr Cys Arg Leu Arg Glu Tyr Tyr Asp Gln
        35                  40                  45

Thr Ala Gln Met Cys Cys Ser Lys Cys Ser Pro Gly Gln His Ala Lys
    50                  55                  60

Val Phe Cys Thr Lys Thr Ser Asp Thr Val Cys Asp Ser Cys Glu Asp
65                  70                  75                  80

Ser Thr Tyr Thr Gln Leu Trp Asn Trp Val Pro Glu Cys Leu Ser Cys
                85                  90                  95

Gly Ser Arg Cys Ser Ser Asp Gln Val Glu Thr Gln Ala Cys Thr Arg
            100                 105                 110

Glu Gln Asn Arg Ile Cys Thr Cys Arg Pro Gly Trp Tyr Cys Ala Leu
        115                 120                 125

Ser Lys Gln Glu Gly Cys Arg Leu Cys Ala Pro Leu Arg Lys Cys Arg
    130                 135                 140

Pro Gly Phe Gly Val Ala Arg Pro Gly Thr Glu Thr Ser Asp Val Val
145                 150                 155                 160

Cys Lys Pro Cys Ala Pro Gly Thr Phe Ser Asn Thr Thr Ser Ser Thr
                165                 170                 175

Asp Ile Cys Arg Pro His Gln Ile Cys Asn Val Val Ala Ile Pro Gly
            180                 185                 190

Asn Ala Ser Met Asp Ala Val Cys Thr Ser Thr Ser Pro Thr Arg Ser
        195                 200                 205

Met Ala Pro Gly Ala Val His Leu Pro Gln Pro Val Ser Thr Arg Ser
```

-continued

```
                    210                 215                 220
Gln His Thr Gln Pro Thr Pro Glu Pro Ser Thr Ala Pro Ser Thr Ser
225                     230                 235                 240

Phe Leu Leu Pro Met Gly Pro Ser Pro Pro Ala Glu Gly Ser Thr Gly
                245                 250                 255

Asp

<210> SEQ ID NO 32
<211> LENGTH: 15
<212> TYPE: PRT
<213> ORGANISM: Artificial Sequence
<220> FEATURE:
<223> OTHER INFORMATION: Gly-Ser linker

<400> SEQUENCE: 32

Gly Gly Gly Gly Ser Gly Gly Gly Gly Ser Gly Gly Gly Ser Gly
1               5                   10                  15
```

IMMUNOGLOBULIN FUSION PROTEINS

This is a non-provisional application under 35 U.S.C. §111 (a) which claims benefit from U.S. provisional application 60/940,753 filed on May 30, 2007, which is incorporated herein by reference.

TECHNICAL FIELD

The present invention relates to a hybrid human Fc and an immunoglobulin fusion protein in which the hybrid human Fc is joined to a biologically active molecule. In particular, it relates to a hybrid human Fc, which is derived from combinations of human immunoglobulin G (IgG) subclasses or combinations of human IgD and IgG, and a fusion protein in which such an Fc is coupled to a biologically active molecule via a covalent bond.

RELEVANT ART

Biologically active molecules may be of great interest therapeutically. However, they may have disadvantages as a therapeutic agent because their in vivo stability is low. Their circulating half-life or serum half-life is short because they are digested by various enzymes in living body. Therefore, it has been desired to improve circulating half-life of biologically active molecules.

It has been known that increasing the size of a protein can increase its half-life by preventing removal of the protein by kidney (Knauf et al., J. Biol. Chem. 1988. 263:15064-15070). For example, it was reported to increase protein stability by coupling an active protein to human albumin (Kinstler et al., Pharm. Res. 1995. 12: 1883-1888). However, since the coupling of an active protein to human albumin only slightly increases its residence time, it was not an effective method to develop an effective pharmaceutical formulation containing the active protein which is coupled to human albumin.

The other reported method is to modulate glycosylation of a protein. The additional glycosyltion at the protein and the introduction of sialic acids to the proteins lead to the prevention of degradation of the proteins in liver. But, the increase in glycosylation of the proteins also leads to a decrease of bioactivity of the proteins.

To stabilize proteins and prevent clearance by kidney, proteins have been conjugated to polyethylene glycol (PEG). The covalent conjugation to PEG has been widely used to deliver a drug of a prolonged half-life (Delgado et al., 1992. 9: 249-304). However, it was reported that PEG conjugation to cytokines or hormones results in a reduced receptor binding affinity due to steric hindrance caused by the conjugation.

Recently, fusion proteins manufactured using an immunoglobulin (Ig) has been researched and developed. Ig is a major component of blood. Human Ig (hIg) includes various classes such as IgG, IgM, IgA, IgD, and IgE (Roitt et al., "Immunology" 1989, Gower Medical Publishing, London, U. K.; New York, N. Y.). Human IgGs can be further classified into various subtypes known as human IgG1 (hIgG1), human IgG2 (hIgG2), human IgG3 (hIgG3), and human IgG4 (hIgG4).

Immunoglobulins are comprised of four polypeptide chains, two heavy chains and two light chains, which are associated via disulfide bonds to form tetramers. Each chain is composed of a variable region and a constant region. The constant region of the heavy chain is further divided into three or four regions (CH1, CH2, CH3, and CH4), depending on the isotypes. The Fc portion of the heavy chain constant region, depending on the Ig isotype, includes hinge, CH2, CH3, and/or CH4 domains.

Regarding serum half-life, IgG1, IgG2, and IgG4 have long half-lives of 21 days, while other immunoglobulins have relatively short half lives with less than a week. The chimeric proteins fused to Fc portion of IgG shows increased stability and increased serum half-life (Capon et al., Nature 1989. 337: 525-531). The biologically active proteins have been fused at the N-terminus of the CH1 region, the N-terminus of Fc region, or at the C-terminus of CH3 region of IgGs.

At the beginning period, IgG fusion proteins have been created with the extracellular domains of cell surface receptors such as CD4 (Capon et al., Nature 1989. 337: 525-531), TNFR (Mohler et al., J. Immunology 1993. 151: 1548-1561), CTLA4 (Linsley et al., J. Exp. Med. 1991. 173: 721-730), CD86 (Morton et al., J. Immunology 1996. 156: 1047-1054). Also, there are several cytokines and growth hormones which have been fused to IgG domains. However, unlike the fusion with the extracellular domains of cell surface receptors, the fusion with soluble proteins to IgGs leads to reduced biological activities, compared to the non-fused cytokine or growth factors. The chimeric proteins exist as dimers, which lead to the steric hindrance from the interacting with their target molecules like receptors, due to the presence of two active proteins in close proximity to one another. Therefore, this problem should be overcome to make an efficient fusion protein.

The other limitation of the Fc fusion technology is the presence of undesirable immune responses. The Fc domain of the immunoglobulin has also effector functions such as antibody dependent cell-mediated cytotoxicity (ADCC) or complement-dependent cytotoxicity (CDC). This effector functions are generally achieved via interaction between the Fc region of the Ig and FcRs on effector cells or via complement binding. Therefore, the blocking of effector functions of Fc should be performed to reduce the undesirable reactions such as cell killing, cytokine release, or inflammation.

In summary, there are needs for improved Fc fusion proteins with minimal loss of biological activity and with less risk of undesired immune responses.

SUMMARY OF THE INVENTION

The present invention provides a hybrid Fc, which is derived from combinations of human IgG subclasses or combinations of human IgD and IgG. The hybrid Fc is effective, when joined to a biologically active molecule, to increase serum half-life of the biologically active molecule as well as increase expression level of the polypeptide when a nucleotide coding for the Fc-polypeptide fusion protein is expressed.

The present invention also provides a hybrid Fc fusion polypeptide in which the hybrid Fc is joined to a biologically active molecule. The fusion protein sometimes is referred to as "biologically active-molecule-Fc fusion protein" or simply "fusion protein." The fusion protein may have a linker between the Fc and the biologically active molecule. The Fc may be coupled at its N-terminal to a C-terminal of the biologically active molecule.

The fusion protein may be produced by fabricating a nucleotide construct coding for and being capable of expressing the fusion protein; expressing it in a host cell; and harvest the fusion protein. Alternatively, the fusion protein may be produced by expressing a nucleotide coding for the Fc and coupling it to a biologically active molecule in a conventional manner.

The polypeptide according to one embodiment of the present invention may be represented by the following formula:

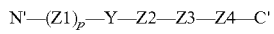

$$N'-(Z1)_p-Y-Z2-Z3-Z4-C'$$

wherein N' is the N-terminus and C' is the C-terminus of the polypeptide;

Z1 indicates an amino acid sequence including at least a C-terminal portion of the amino acid residues at positions 90 to 98 of SEQ ID NO:11 or at least a portion of the amino acid residues at positions 90-98 of SEQ ID NO:14;

Y indicates an amino acid sequence including at least a C-terminal portion of the amino acid residues at positions 99 to 113 of SEQ ID NO:11 or at least a portion of the amino acid residues at positions 99 to 162 of SEQ ID NO:14;

Z2 indicates an amino acid sequence including at least an N-terminal portion of the amino acid residues at positions 111 to 147 of SEQ ID NO:12 or at least a portion of the amino acid residues at positions 163 to 199 of SEQ ID NO:14;

Z3 indicates an amino acid sequence including at least a C-terminal portion of the amino acid residues at positions 118-223 of SEQ ID NO:11, 114-219 of SEQ ID NO:12, 165-270 of SEQ ID NO:24, or 115 to 220 of SEQ ID NO:13;

Z4 indicates an amino acid sequence including at least an N-terminal portion of the amino acid residues at positions 224-330 of SEQ ID NO:11, 220-326 of SEQ ID NO:12, 271-377 of SEQ ID NO:24, or 221-327 of SEQ ID NO:13; and p is an integer of 0 or 1, wherein the total number of the amino acid residues for Z2 and Z3 is between 80 and 140, both inclusive.

Z1 can be an amino acid sequence including 5 to 9 consecutive amino acid residues from the C-terminal side of the amino acid residues at positions 90-98 of SEQ ID NO:11, or 5-9 consecutive amino acid residues from the C-terminal side of the amino acid residues at positions 90-98 of SEQ ID NO:14. In some embodiments, Z1 can be 5, 6, 7, 8 or 9 C-terminal amino acid residues of an IgG1 CH1 domain (SEQ ID NO:11) or IgD CH1 domain (SEQ ID NO:14).

In another embodiment, Z1 is an amino acid sequence including amino acid residues at positions 90 to 98 of SEQ ID NO:11 or amino acid residues at positions 90 to 98 of SEQ ID NO:14. Z1 may be an amino acid sequence consisting of 5 to 9 amino acid residues at positions 90 to 98 of SEQ ID NO:11 or amino acid residues at positions 90 to 98 of SEQ ID NO:14. Z1 also may be an amino acid sequence consisting of amino acid residues 90 to 98 of SEQ ID NO:11 or amino acid residues 90 to 98 of SEQ ID NO:14.

Y can be an amino acid sequence including 5 or more, or 10 or more consecutive amino acid residues from the C-terminal side of the amino acid residues at positions 99 to 113 of SEQ ID NO:11 or 5 or more, or 10 or more consecutive amino acid residues from the C-terminal side of the amino acid residues at positions 99 to 162 of SEQ ID NO:14. In certain embodiments, Y can be an amino acid sequence including amino acid residues at positions 99 to 113 of SEQ ID NO:11, amino acid residues at positions 158 to 162 of SEQ ID NO:14, amino acid residues at positions 153 to 162 of SEQ ID NO:14, amino acid residues at positions 143 to 162 of SEQ ID NO:14, amino acid residues at positions 133 to 162 of SEQ ID NO:14, or amino acid residues at positions 99 to 162 of SEQ ID NO:14.

Z2 can be an amino acid sequence including 4 to 37, or 6-30 consecutive amino acid residues from the N-terminal side of the amino acid residues at positions 111 to 147 of SEQ ID NO:12 (hIgG2) or 4 to 37, or 6-30 consecutive amino acid residues from the N-terminal side of the amino acid residues at positions 163 to 199 of SEQ ID NO:14 (hIgD). In certain embodiments, Z2 can be 6 N-terminal amino aid residues of a human IgG2 CH2 domain or 8 N-terminal amino acid residues of a human IgD CH2 domain.

The total number of amino acid residues of Z2 and Z3 can be between 80 and 140. In an embodiment, the total number of amino acid residues of Z2 and Z3 is between 90 and 120, both inclusive. In another embodiment, the total number of amino acid residues of Z2 and Z3 is between 105 and 115, both inclusive. In one embodiment, the total number of amino acid residues of Z2 and Z3 is 108. In a still embodiment, the total number of amino acid residues of Z2 and Z3 is 109.

Z4 can be an amino acid sequence including 90 or more, or 100 or more consecutive amino acid residues at positions 224-330 of SEQ ID NO:11 (hIgG1), 220-326 of SEQ ID NO:12 (hIgG2), 271-377 of SEQ ID NO:24 (hIgG3), or 221 to 327 of SEQ ID NO:13 (hIgG4). Z4 can be an amino acid sequence of the amino acid residues at positions 224-330 of SEQ ID NO:11, 220-326 of SEQ ID NO:12, 271-377 of SEQ ID NO:24, or 221 to 327 of SEQ ID NO:13.

According to an embodiment, Z3-Z4 is an amino acid sequence selected from the group consisting of (i) a continuous amino acid sequence comprised of the C-terminal portion of the amino acid residues at positions 118 to 223 of SEQ ID NO:11 and the N-terminal portion of the amino acid residues at positions 224 to 330 of SEQ ID NO:11, (ii) a continuous amino acid sequence comprised of the C-terminal portion of the amino acid residues at positions 114 to 219 of SEQ ID NO:12 and the N-terminal portion of the amino acid residues at positions 220 to 326 of SEQ ID NO:12, (iii) a continuous amino acid sequence comprised of the C-terminal portion of the amino acid residues at positions 165 to 270 of SEQ ID NO: 24 and the N-terminal portion of the amino acid residues at positions 271 to 377 of SEQ ID NO:24, and (iv) a continuous amino acid sequence of the C-terminal portion of the amino acid residues at positions 115 to 220 of SEQ ID NO:13 and the N-terminal portion of the amino acid residues at positions 221 to 327 of SEQ ID NO:13.

The total number of amino acid residues of the polypeptide according to one embodiment of the present invention is from 154 to 288.

In one embodiment, Y can be an amino acid sequence including at least a portion of the amino acid residues at positions 99-113 of SEQ ID NO:11, p can be 1 or 0, Z2 can be an amino acid sequence including at least a portion of the amino acid residues at positions 111-147 of SEQ ID NO:12, and Z3 can be an amino acid sequence including at least a portion of the amino acid residues at positions 118-223 of SEQ ID NO:11, 114-219 of SEQ ID NO:12, 165-270 of SEQ ID NO:24, or 115 to 220 of SEQ ID NO:13. In this embodiment, when p is 1, Z1 can be an amino acid sequence including at least a portion of the amino acid residues at positions 90 to 98 of SEQ ID NO:11.

In further embodiments, Z3 can be 73 to 106 consecutive amino acid residues at positions 118-223 of SEQ ID NO:11, 114-219 of SEQ ID NO:12, 165-270 of SEQ ID NO:24, or 115-220 of SEQ ID NO:13, and the total number of the amino acid residues of Z2 and Z3 can be 110. Z2 can be an amino acid sequence of the amino acid residues at positions 111-116 of SEQ ID NO:12, and Z3 can be an amino acid sequence of the amino acid residues at positions 120-223 of SEQ ID NO:11, 116-219 of SEQ ID NO:12, 167-270 of SEQ ID NO:24, or 118 to 220 of SEQ ID NO:13.

In another embodiment, Y can be an amino acid sequence including at least a portion of the amino acid residues at positions 99 to 162 of SEQ ID NO:14, p can be 1 or 0 (zero), Z2 can be an amino acid sequence including at least a portion of the amino acid residues at positions 163 to 199 of SEQ ID NO:14, and Z3 can be an amino acid sequence including at least a portion of the amino acid residues at positions 121 to 220 of SEQ ID NO:13. In this embodiment, when p is 1, Z1 can be an amino acid sequence including the amino acid residues at positions 90 to 98 of SEQ ID NO:14.

In further embodiments, Y can be 20 consecutive amino acid residues or more, 30 consecutive amino acid residues or more, 40 consecutive amino acid residues or more, 50 consecutive amino acid residues or more, or 60 consecutive amino acid residues or more of the C-terminal side of the amino acid residues at positions 99-162 of SEQ ID NO:14. Z2 can be the amino acid residues at positions 163 to 170 of SEQ ID NO:14, Z3 can comprise 71 to 100 consecutive amino acid residues of the C-terminal side of the amino acid residues at positions 124-223 of SEQ ID NO:11, 120-219 of SEQ ID NO:12, 171-270 of SEQ ID NO:24, or 121-220 of SEQ ID NO:13. The total number of the amino acid residues for Z2 and Z3 can be 108.

In one embodiment, the polypeptide may be encoded by a nucleotide sequence selected from the group consisting of SEQ ID NO:1, SEQ ID NO:2, SEQ ID NO:3, SEQ ID NO:4, SEQ ID NO:5, SEQ ID NO:6, SEQ ID NO:26, and SEQ ID NO:27. The polypeptide is an amino acid sequence selected from the group consisting of SEQ ID NO:18, SEQ ID NO: 19, SEQ ID NO:20, SEQ ID NO:21, SEQ ID NO:22, SEQ ID NO:23, SEQ ID NO:28, and SEQ ID NO:29.

In an embodiment, the polypeptide is fused at its N-terminus with a biologically active molecule which shows an increased circulating half-life compared to the circulating half-life of the native form of said biologically active molecule. The biologically active molecule may be a polypeptide, protein, or a peptide. The biologically active molecule may be a polypeptide, peptide or a protein drug. The biologically active molecule may be a soluble protein such as, but not limited to, a hormone, cytokine, growth factor, a co-stimulatory molecule, hormone receptor, cytokine receptor, growth factor receptor, or short peptide. The biologically active molecule may be EPO or its variants/fragments, p40 or its variants/fragments (e.g., p40 variant which contains Asn303Gln substitution), G-CSF or its variants/fragments, TNF receptor, GM-CSF, IL-1, IL-2, IL-3, IL-4, IL-5, IL-6, IL-7, IL-8, IL-10, IL-10 receptor, TGF-beta, TGF-beta receptor, IL-17, IL-17 receptor, Factor VII, CXCL-11, FSH, human growth hormone, bone morphogenetic protein-1 (BMP-1), CTLA4, PD-1, GLP-1, betacellulin, OPG, RNAK, interferon-alpha, interferon-beta or their variants/fragments. The biologically active molecule may be a secreted protein, which may be in a mature form.

In one embodiment, there is provided a method of producing the polypeptide according to claim 1, wherein the method comprises the steps of: (i) introducing a DNA molecule coding for the polypeptide into a mammalian host cell, (ii) growing the cell under conditions where the polypeptide can be expressed in its growth medium; and (iii) harvesting the expressed polypeptide. The mammalian host cell may be a CHO, COS or BHK cells.

In another embodiment, there is provided a method of (i) reducing the symptoms of, preventing or treating an autoimmune disease, (ii) inhibiting rejection of a graft, or (iii) treating or preventing endotoxin-induced shock, including administering a therapeutically effective amount of the polypeptide described above, wherein the polypeptide is fused to a biologically active molecule.

In one embodiment, there is provided an isolated nucleic acid molecule which encodes the polypeptide according to embodiments of the present invention. The polypeptide may have an amino acid sequence selected from the group consisting of SEQ ID NO:18, SEQ ID NO:19, SEQ ID NO:20, SEQ ID NO:21, SEQ ID NO:22, SEQ ID NO:23, SEQ ID NO:28, and SEQ ID NO:29. The nucleic acid molecule may have a nucleotide sequence as shown in SEQ ID NO:1, SEQ ID NO:2, SEQ ID NO:3, SEQ ID NO:4, SEQ ID NO:5, SEQ ID NO:6, SEQ ID NO:26, or SEQ ID NO:27. The nucleic acid molecule may further include a signal sequence or leader sequence.

According to an embodiment of the invention, there are provided an expression vector including the nucleic acid molecule and a host cell containing the vector. Examples of the expression vector may include, be not limited to, pAD11 EPO-hFc-1, pAD11 G-CSF-hFc-1, pAD11 p40N303Q-hFc-1, pAD11 EPO-hFc-6, pAD11 G-CSF-hFc-6, pAD11 p40N303Q-hFc-6, pAD11 EPO-hFc-5, pAD11 G-CSF-hFc-5, pAD11 p40N303Q-hFc-5 and pAD11 TNFR-hFc-5.

In one embodiment, there is provided a method of delivering a biologically active molecule to a mammal, including the step of administering the nucleic acid molecule to the mammal in need thereof.

In another embodiment, a polypeptide includes an Fc domain which consists of a hinge region, a CH2 domain and a CH3 domain in an N-terminal to C-terminal direction, wherein said hinge region includes at least a portion of amino acid residues of a human IgD hinge region or human IgG1 hinge region; said CH2 domain includes at least a portion of amino acid residues of a human IgG4 CH2 domain, wherein 4-37 consecutive amino acid residues at the N-terminus of the human IgG4 CH2 domain are replaced with at least a portion of amino acid residues of the N-terminal region of a human IgG2 CH2 domain or the N-terminal region of a human IgD CH2 domain, and said CH3 domain includes at least a portion of amino acid residues of a human IgG4 CH3 domain.

The hinge region may include at least a portion of amino acid residues of the human IgG1 hinge region, said CH2 domain includes at least a portion of amino acid residues of the human IgG4 CH2 domain, wherein the 4-37 amino acid residues at the N-terminus of the human IgG4 CH2 domain are replaced with at least a portion of the amino acid residues of the N-terminal region of the human IgG2 CH2 domain.

The hinge region may include at least a portion of amino acid residues of the human IgD hinge region, said CH2 domain includes at least a portion of amino acid residues of the human IgG4 CH2 domain, wherein 4-37 amino acid residues at the N-terminus of the human IgG4 CH2 domain are replaced with at least a portion of the amino acid residues of the N-terminal region of the human IgD CH2 domain.

The polypeptide may further include a CH1 domain, wherein said CH1 domain includes at least a portion of amino acid residues of the human IgG1 CH1 domain, and wherein said CH1 domain is coupled to the N-terminus of said hinge region. The polypeptide may further include a CH1 domain, wherein said CH1 domain includes at least a portion of amino acid residues of the human IgD CH1 domain, and wherein said CH1 domain is coupled to the N-terminus of said hinge region. The polypeptide may further include a second polypeptide coupled to the N-terminus of said hinge region, wherein the second polypeptide is a biologically active non-immunoglobulin polypeptide. The polypeptide may further include a biologically active molecule coupled to the N-terminus of said CH1 domain or to the C-terminus of said CH4 domain through a linker, wherein said biologically active molecule is not an immunoglobulin polypeptide. The polypeptide and the biologically active molecule may be coupled to each other via a linker. The linker molecule is an albumin linker or a synthetic linker. The albumin linker comprises amino acid sequence 321 to 323, 318 to 325, 316 to 328, 313 to 330, 311 to 333, or 306 to 338 of SEQ ID NO:25. The synthetic linker may be a peptide of 10 to 20 amino acid residues composed of Gly and Ser residues. In one embodiment, such Gly-Ser linker is GGGGSGGGGSGGGSG (SEQ ID NO:32).

The present invention also encompasses an antibody molecule comprising a recombinant Fc region, the recombinant Fc region is described as above.

BRIEF DESCRIPTION OF THE INVENTION

Figure 7A:
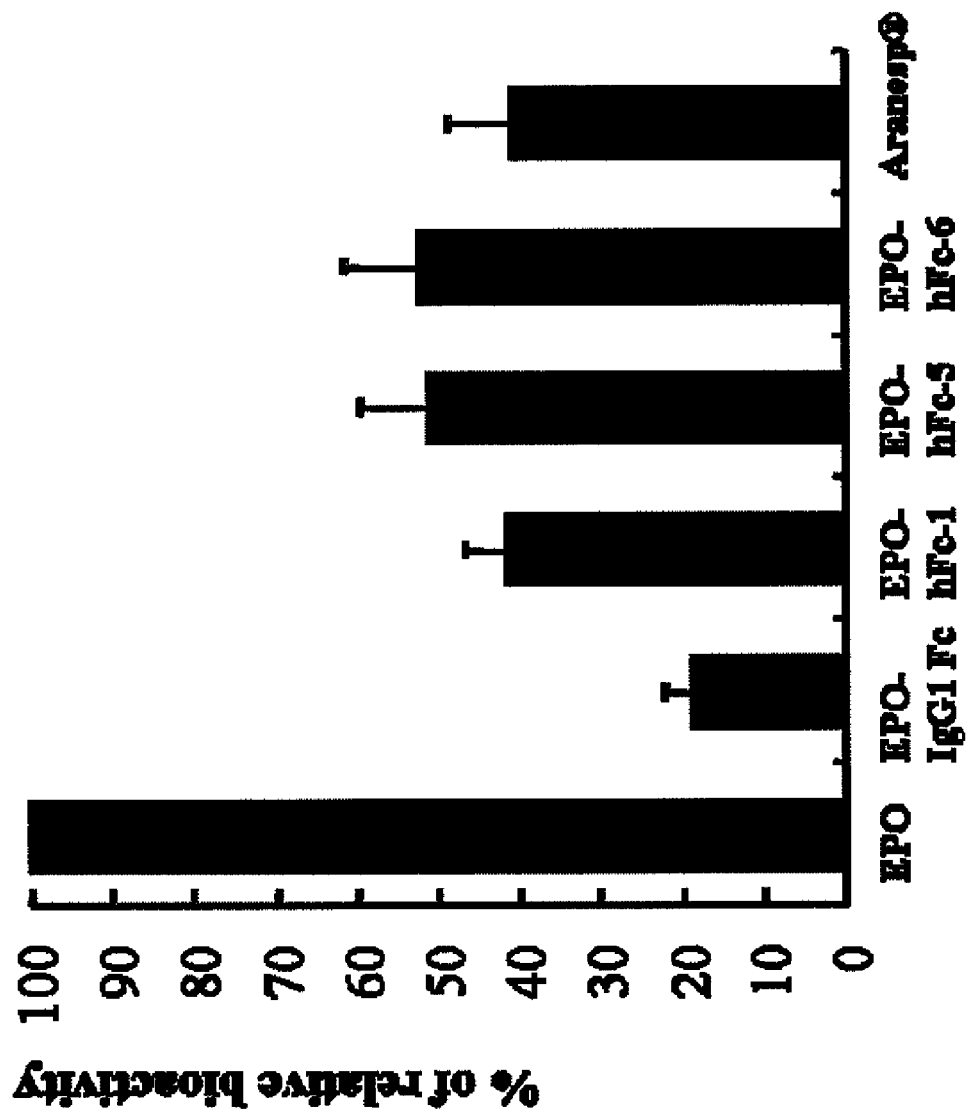
Figure 7B:
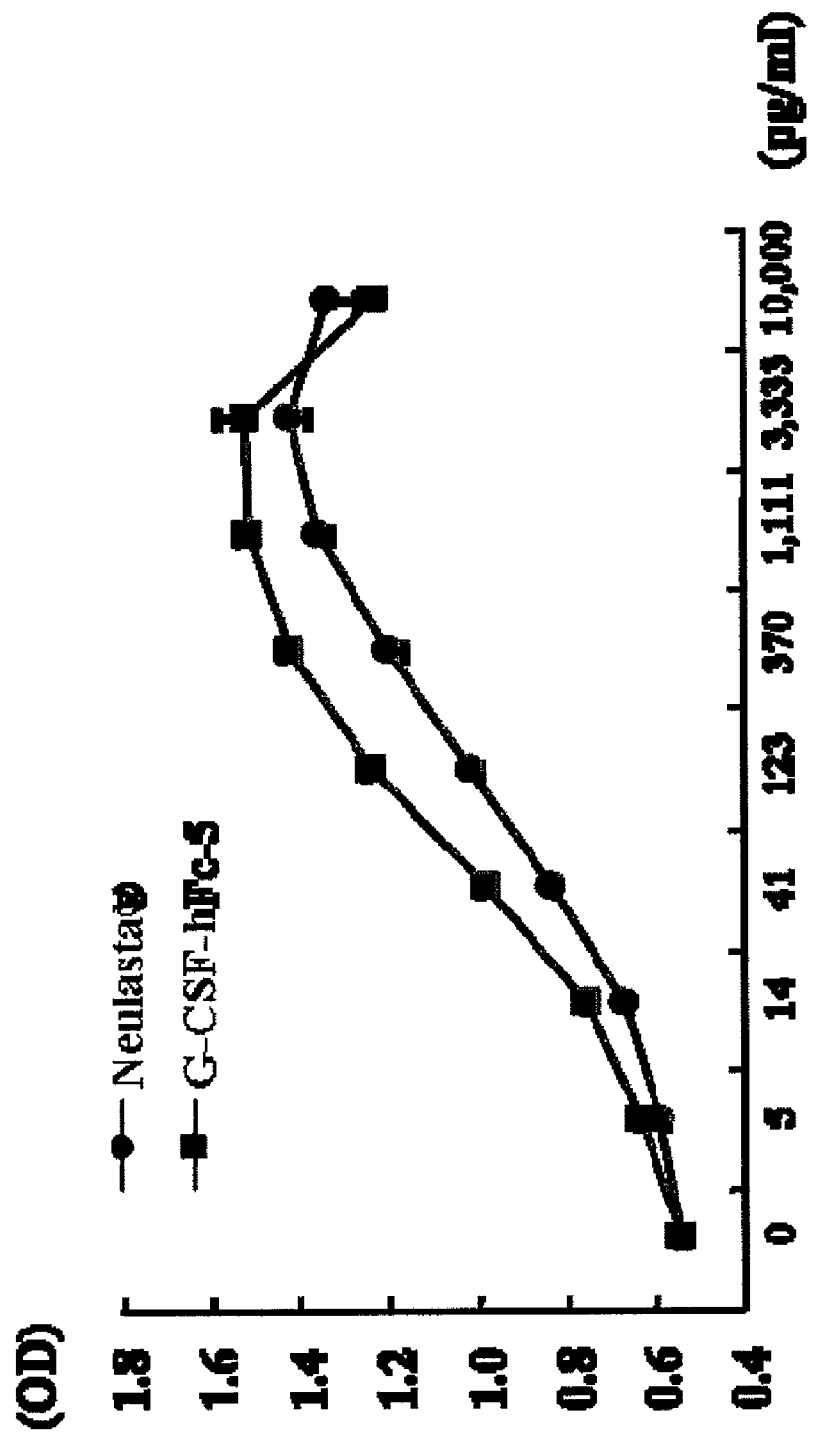
Figure 7C:
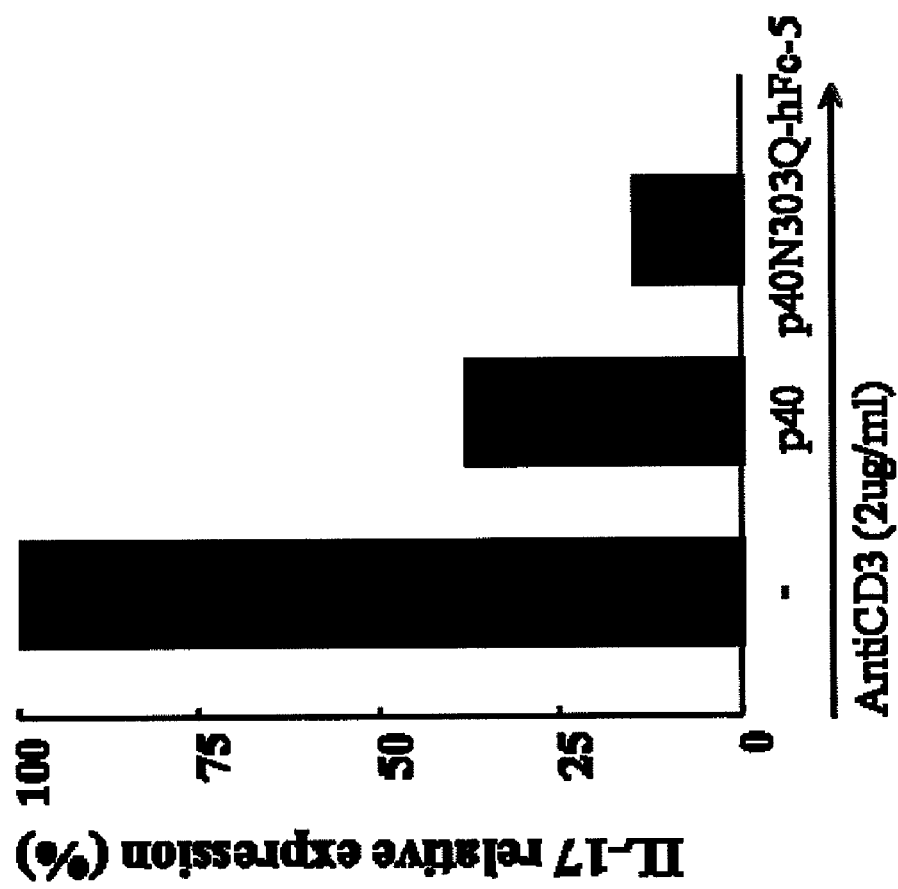
Figure 7D:
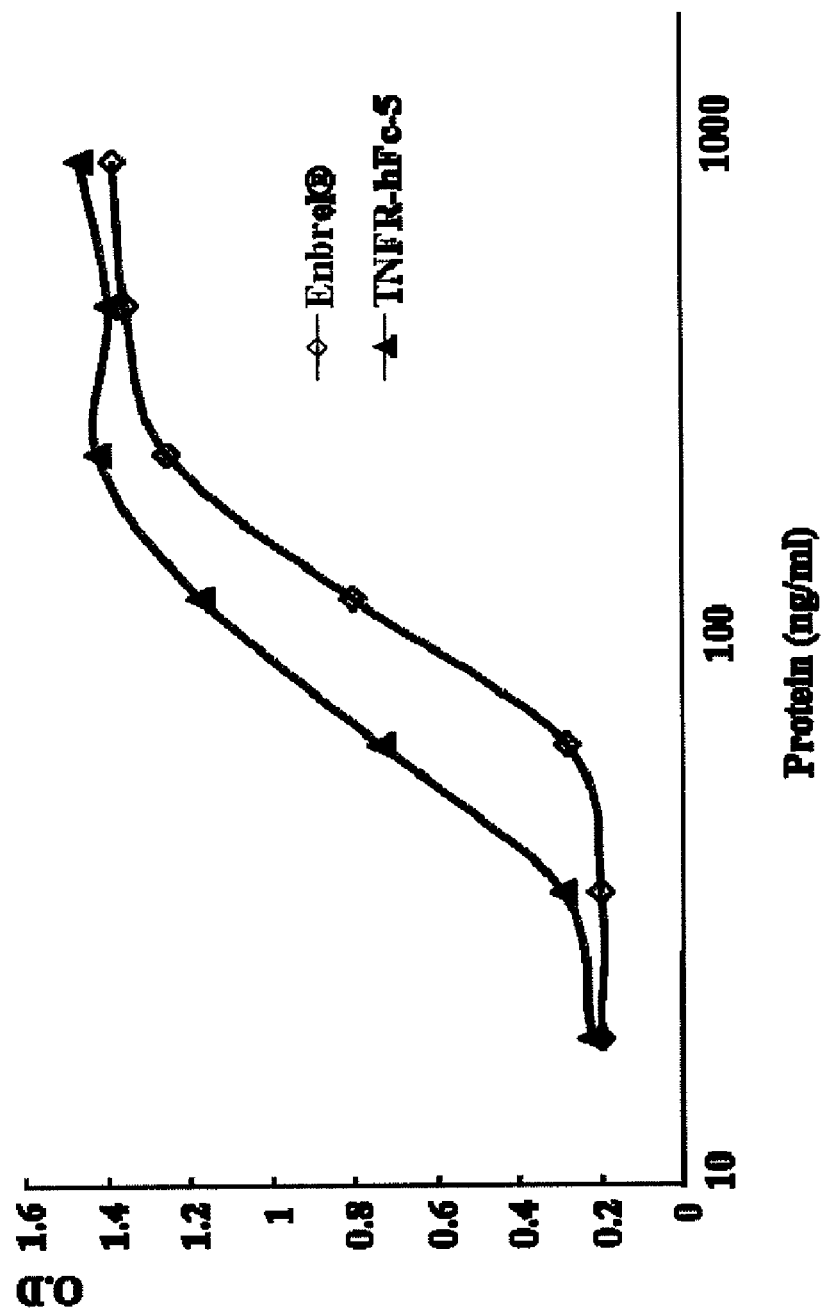

FIG. 7(a) shows the results of bioactivities of EPO-IgG1 Fc, EPO-hFc-1, EPO-hFc-5, EPO-hFc-6 and Aranesp® (darbepoetin alfa), compared to that of EPO in human F36E cell line; FIG. 7(b) shows the results of in vitro bioactivities of Neulasta® (pegfilgrastim) and G-CSF-hFc-5 in mouse hematopoietic cell line (NFS-60); FIG. 7(c) shows the results of in vitro bioactivities of p40 and p40N303Q-hFc-5 in human PBMCs; FIG. 7(d) shows the results of in vitro bioactivities of Enbrel® (etanercept) and TNFR-hFc-5 in Murine L929 cells; and FIG. 7(e) shows the results of in vitro bioactivites of thFc-1-AL(0)-IFN-beta and thFc-1-AL(3)-IFN-beta in human WISH cells.

Figure 8A:
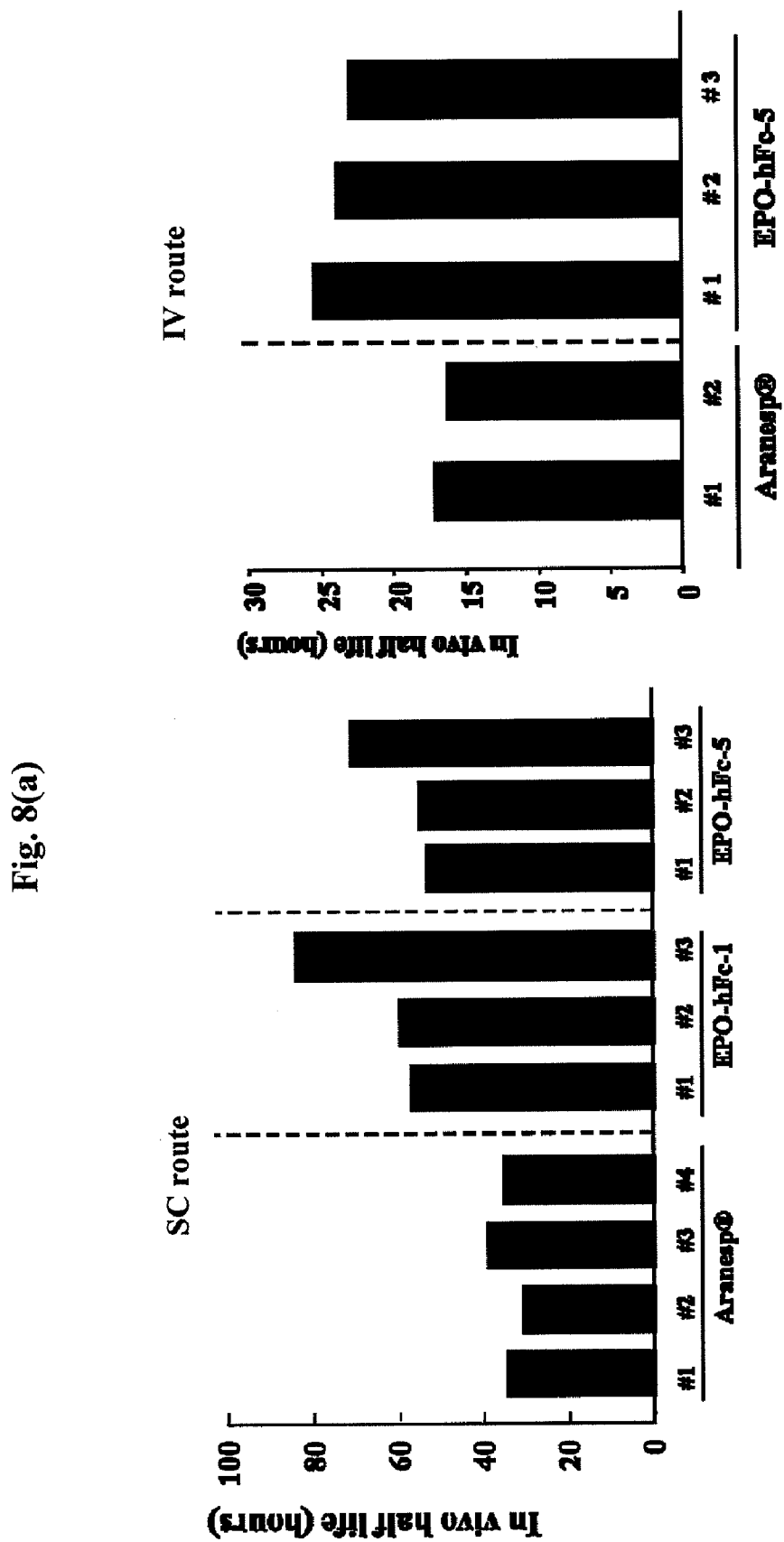
Figure 8B:
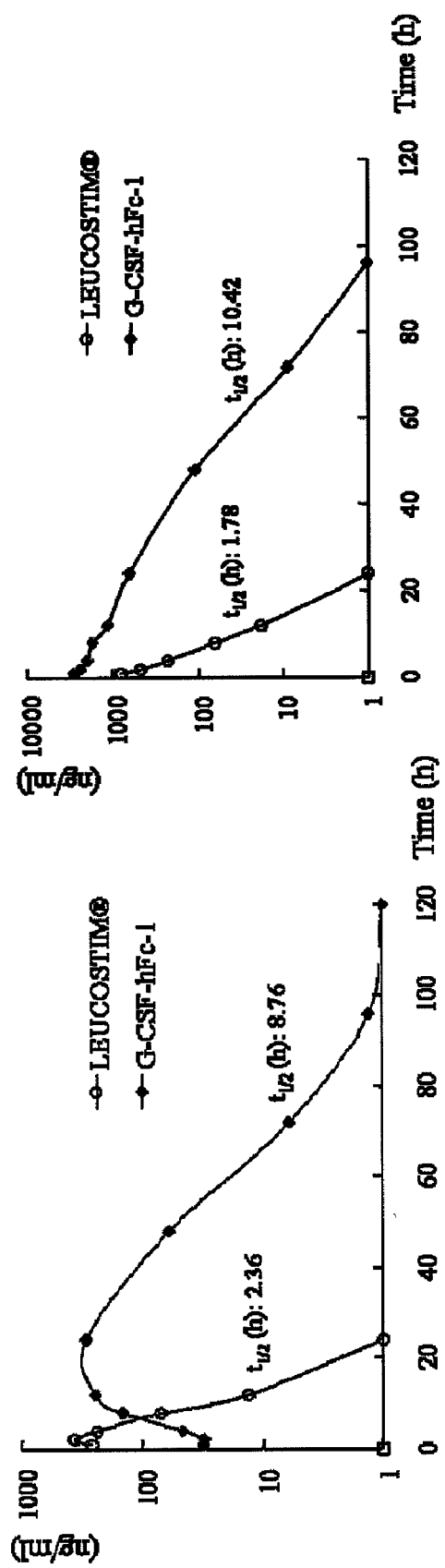
Figure 8C:
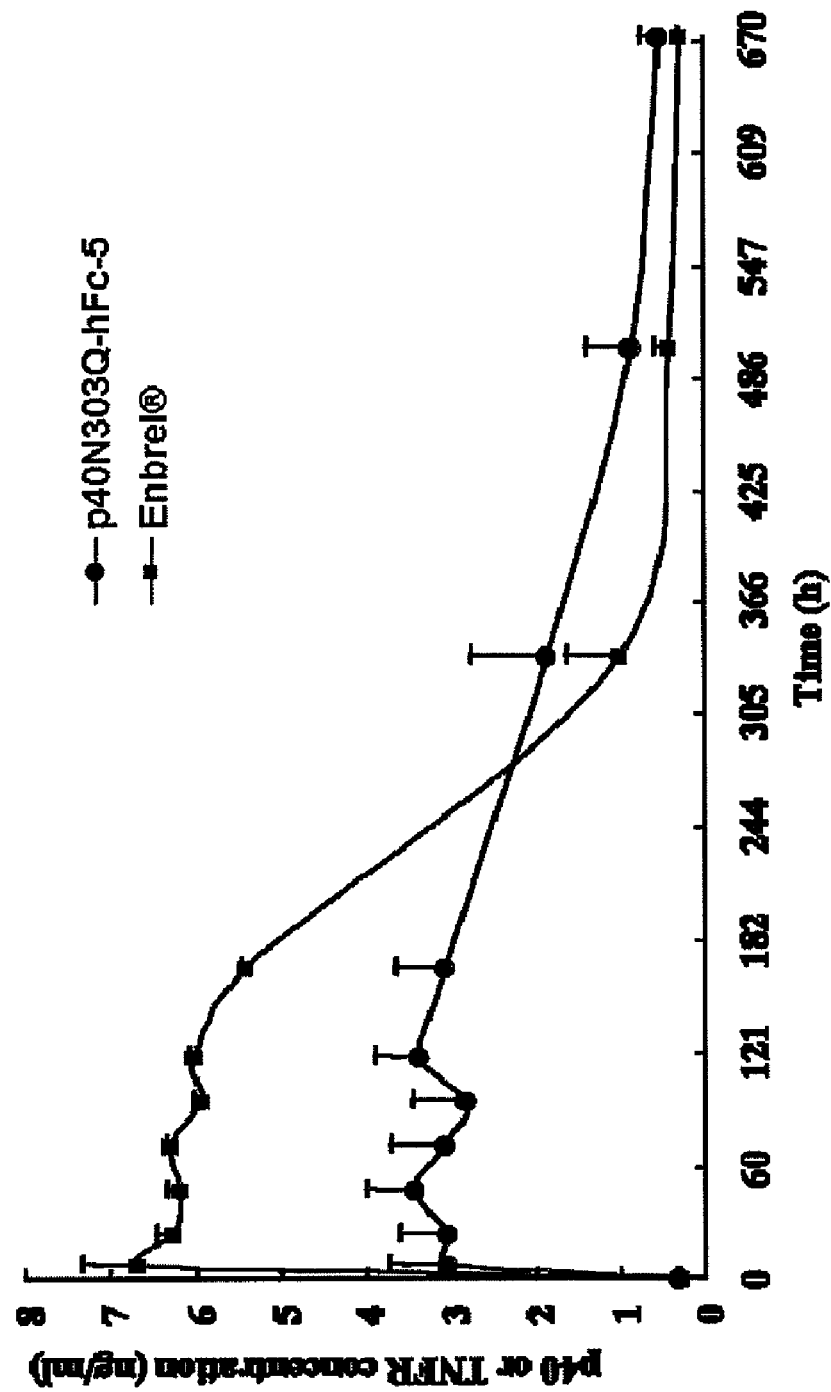
Figure 8D:
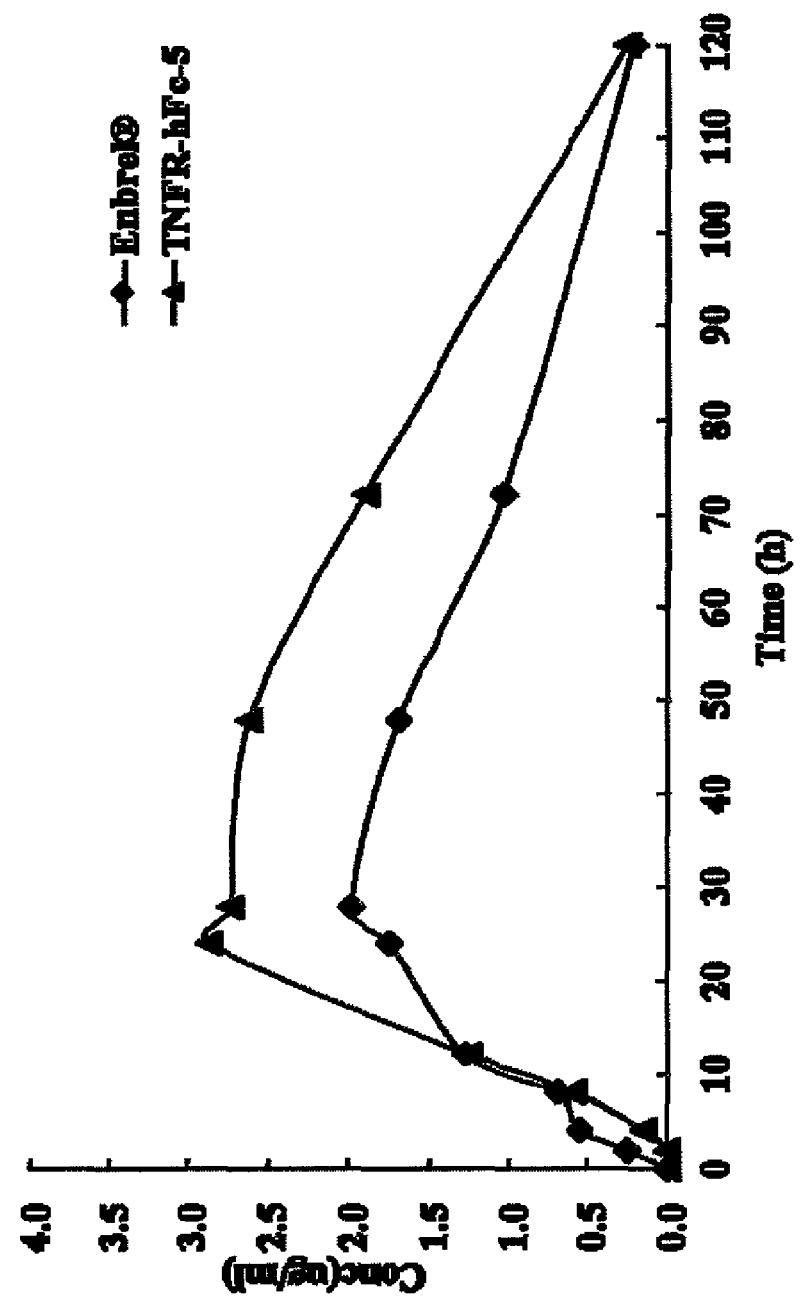

FIG. 8(a) shows the results of in vivo half life of Aranesp® (darbepoetin alfa), EPO-hFc-1, or EPO-hFc-5 administered to cynomolgus monkeys via SC route (left panel) and IV route (right panel); FIG. 8(b) shows the results of pharmacokinetics of LEUCOSTIM® (filgrastim) and G-CSF-hFc-1 administered to Sprague Dawley rats via SC route (left panel) and IV route (right panel); FIG. 8(c) shows the results of pharmacokinetics of p40N303Q-hFc-5 and Enbrel® (etanercept) administered to cynomolgus monkeys via SC route: FIG. 8(d) shows the results of pharmacokinetics of TNFR-hFc-5 and Enbrel® (etanercept) administered to Sprague Dawley rats via SC route.

Figure 9A:
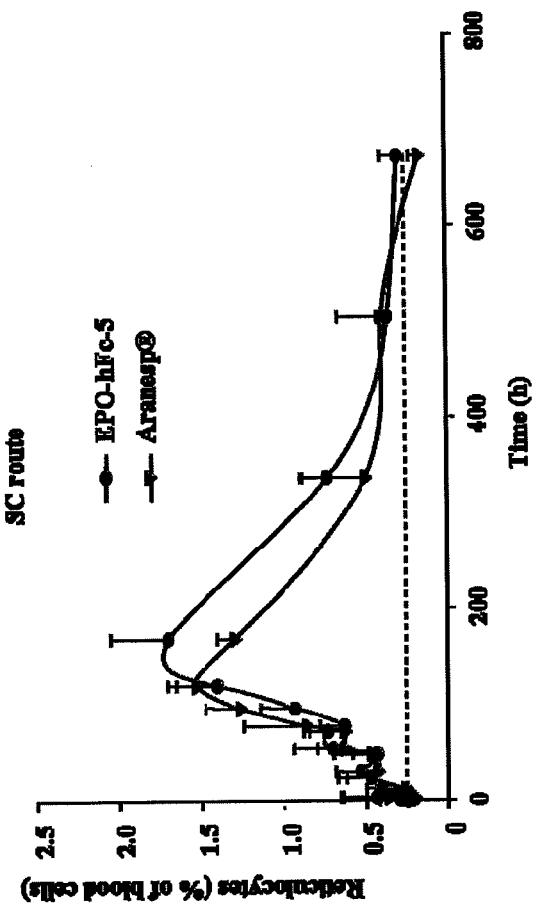
Figure 9A:
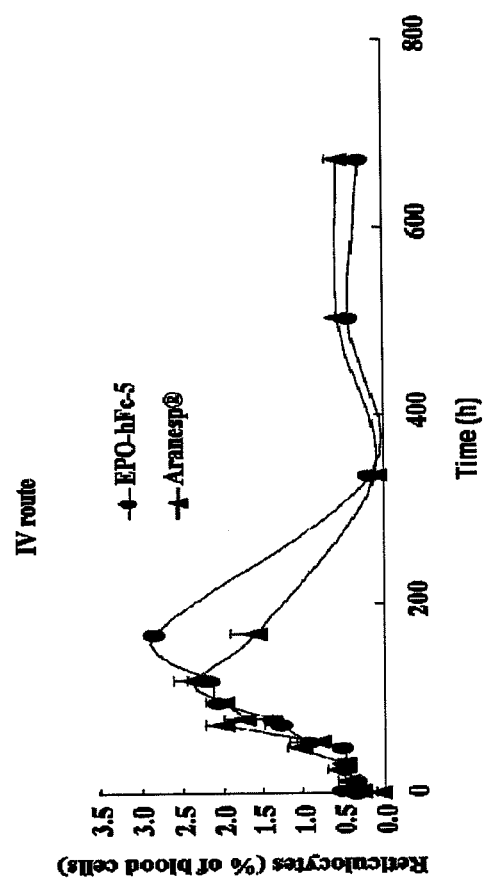
Figure 9B:
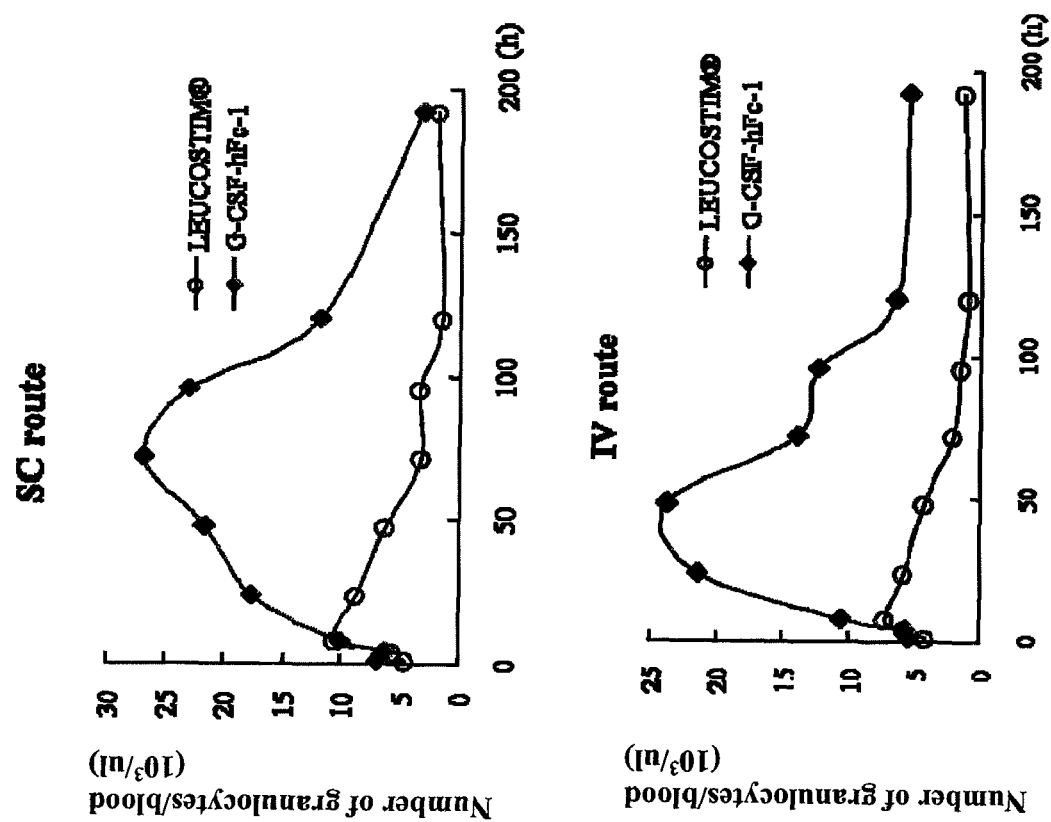

FIG. 9(a) shows the results of in vivo bioactivities of Aranesp® (darbepoetin alfa) and EPO-hFc-5 administered to cynomolgus monkeys via SC route (upper panel) and IV route (lower panel) and FIG. 9(b) shows the results of in vivo bioactivities of LEUCOSTIM® (filgrastim) and G-CSF-hFc-1 administered to Sprague Dawley rats via SC route (upper panel) and IV route (lower panel).

DETAILED DESCRIPTION OF THE INVENTION

The present invention provides a hybrid human immunoglobulin Fc fragment, which includes a hinge region, a CH2 domain and a CH3 domain in an N-terminal to C-terminal direction, wherein the hinge region is an at least partial amino acid sequence of a human IgD hinge region or a human IgG1 hinge region; and the CH2 domain is of human IgG4 CH2 domain, a portion of which, at its N-terminal region, is replaced by 4-37 amino acid residues of an N-terminal region of a human IgG2 CH2 or human IgD CH2 domain. Such hybrid Fc fragment, when joined to a biologically active molecule, such as a biologically active molecule, to produce a Fc fusion protein, minimizes non-specific immunoreactions of the Fc fusion protein, prolongs the serum half-life of the biologically active molecule, and optimizes the activity of the biologically active molecule.

In the Fc fusion protein according to one embodiment of the present invention, the combination of the N-terminal of IgD CH2 domain with the remaining portion of the IgG4 CH2 domain was designed that the region of the resulting fusion protein where two different Ig subunits are recombined is hydrophobic. The hydrophobic region of the resulting fused protein will be located inside a folded protein, minimizing undesired non-specific immune reaction.

The term "Fc fragment" or "Fc," as used herein, refers to a protein that contains the heavy-chain constant region 1 (CH1), the heavy-chain constant region 2 (CH2) and the heavy-chain constant region 3 (CH3) of an immunoglobulin, and not the variable regions of the heavy and light chains, and the light-chain constant region 1 (CL1) of the immunoglobulin. It may further include the hinge region at the heavy-chain constant region. Hybrid Fc or hybrid Fc fragment is sometimes referred to herein as "hFc."

In addition, the Fc fragment of the present invention may be in the form of having native sugar chains, increased sugar chains compared to a native form or decreased sugar chains compared to the native form, or may be in a deglycosylated form. The increase, decrease or removal of the immunoglobulin Fc sugar chains may be achieved by methods common in the art, such as a chemical method, an enzymatic method and a genetic engineering method using a microorganism. The removal of sugar chains from an Fc fragment results in a sharp decrease in binding affinity to the C1q part of the first complement component C1 and a decrease or loss in antibody-dependent cell-mediated cytotoxicity (ADCC) or complement-dependent cytotoxicity (CDC), thereby not inducing unnecessary immune responses in vivo. In this regard, an immunoglobulin Fc fragment in a deglycosylated or aglycosylated form may be, in some cases, more suitable to the object of the present invention as a drug carrier.

As used herein, the term "deglycosylation" refers to that sugar moieties are enzymatically removed from an Fc fragment, and the term "aglycosylation" means that an Fc fragment is produced in an unglycosylated form by a prokaryote, preferably E. coli.

The term "hybrid", as used herein, means that sequences encoding two or more immunoglobulin Fc fragments of different origin are present in a single-chain immunoglobulin Fc fragment.

In an embodiment, the hybrid human Fc includes a hinge region, a CH2 domain and a CH3 domain in an N-terminal to C-terminal direction, wherein the hinge region is an at least partial amino acid sequence of a human IgD hinge region or a human IgG1 hinge region; and the CH2 domain is of human IgG4 CH2 domain, a portion of which, at its N-terminal region, is replaced by 4-37 amino acid residues of an N-terminal region of a human IgG2 CH2 or human IgD CH2 domain. The hybrid human Fc can be joined at its N-terminus to a C-terminus of a biologically active molecule via a covalent bond.

In another embodiment, the biologically active molecule-hybrid Fc fusion polypeptide may be represented by the following formula:

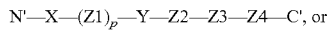

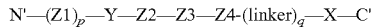

wherein N' is the N-terminus and C' is the C-terminus of the polypeptide; Z1 indicates an amino acid sequence including at least a C-terminal portion of the amino acid residues at positions 90 to 98 of SEQ ID NO:11 or at least a portion of the amino acid residues at positions 90-98 of SEQ ID NO:14; Y indicates an amino acid sequence including at least a C-terminal portion of the amino acid residues at positions 99 to 113 of SEQ ID NO:11 or at least a portion of the amino acid residues at positions 99 to 162 of SEQ ID NO:14; Z2 indicates an amino acid sequence including at least an N-terminal portion of the amino acid residues at positions 111 to 147 of SEQ ID NO:12 or at least an N-terminal portion of the amino acid residues at positions 163 to 199 of SEQ ID NO:14; Z3 indicates an amino acid sequence including at least a C-terminal portion of the amino acid residues at positions 118-223 of SEQ ID NO:11, 114-219 of SEQ ID NO:12, 165-270 of SEQ ID NO:24, or 115 to 220 of SEQ ID NO:13; Z4 indicates an amino acid sequence including at least an N-terminal portion of the amino acid residues at positions 221-327 of SEQ ID NO:13; and p and q are each an integer of 0 or 1, wherein the total number of the amino acid residues for Z2 and Z3 is between 80 and 140, both inclusive, linker is a linker molecule, and X is a biologically active molecule of interest.

In one embodiment, Z3-Z4 is an amino acid sequence selected from the group consisting of (i) a continuous amino acid sequence comprised of the C-terminal portion of the amino acid residues at positions 118 to 223 of SEQ ID NO:11 and the N-terminal portion of the amino acid residues at positions 224 to 330 of SEQ ID NO:11, (ii) a continuous amino acid sequence comprised of the C-terminal portion of the amino acid residues at positions 114 to 219 of SEQ ID NO:12 and the N-terminal portion of the amino acid residues at positions 220 to 326 of SEQ ID NO:12, (iii) a continuous amino acid sequence comprised of the C-terminal portion of the amino acid residues at positions 165 to 270 of SEQ ID NO:24 and the N-terminal portion of the amino acid residues at positions 271 to 377 of SEQ ID NO:24, and (iv) a continuous amino acid sequence of the C-terminal portion of the amino acid residues at positions 115 to 220 of SEQ ID NO:13 and the N-terminal portion of the amino acid residues at positions 221 to 327 of SEQ ID NO:13.

The total number of amino acid residues of the polypeptide according to one embodiment of the present invention is from 154 to 288.

The polypeptides of the formula N'—X—(Z1)$_p$—Y—Z2—Z3—Z4—C' and N'—(Z1)$_p$—Y—Z2—Z3—Z4-(linker)$_q$—X—C' increases the circulating half-life of the biologically active molecule X compared to a circulating half-life of X alone, when administered to a subject.

The linker may be derived from human albumin (CAA00606; SEQ ID NO:25). The linker may comprise amino acid sequence 321 to 323, 318 to 325, 316 to 328, 313 to 330, 311 to 333, or 306 to 338 of SEQ ID NO:25. Alternatively, the linker may be a synthetic linker. The synthetic linker may be a peptide composed of a total 10-20 residues of Gly and Ser. In one embodiment, the Gly-Ser linker is GGGGSGGGGSGGGGSG (SEQ ID NO:32).

Z1 can comprise at least a portion of the CH1 domain of human IgG1 (SEQ ID NO:11) or IgD (SEQ ID NO:14). Z1 can comprise 5 to 9 or 7 to 9 consecutive amino acid residues of the C-terminal region of the IgG1 CH1 domain (positions 90-98 of SEQ ID NO: 11) or the C-terminal region of the IgD CH1 domain (positions 90-98 of SEQ ID NO:14). In some embodiments, Z1 can be 5, 6, 7, 8 or 9 C-terminal amino acid residues of the IgG1 CH1 domain or IgD CH1 domain.

In some embodiments, Z1 is an amino acid sequence including amino acid residues at positions 90 to 98 of SEQ ID NO:11 or amino acid residues at positions 90 to 98 of SEQ ID NO:14. Z1 may be an amino acid sequence consisting of 5 to 9 amino acid residues at positions 90 to 98 of SEQ ID NO:11 or amino acid residues at positions 90 to 98 of SEQ ID NO:14. Z1 also may be an amino acid sequence consisting of amino acid residues 90 to 98 of SEQ ID NO:11 or amino acid residues 90 to 98 of SEQ ID NO:14.

Y can comprise at least a portion of the hinge region of human IgG1 or IgD. Y can comprise 5 or more, or 10 or more consecutive amino acid residues of the C-terminal IgG1 hinge region (amino acid positions 99 to 113 of SEQ ID NO:11) or IgD hinge region (amino acid positions 99 to 162 of SEQ ID NO:14). In certain embodiments, Y can be an amino acid sequence including amino acid residues at positions 99 to 113 of SEQ ID NO:11, amino acid residues at positions 158 to 162 of SEQ ID NO:14, amino acid residues at positions 153 to 162 of SEQ ID NO:14, amino acid residues at positions 143 to 162 of SEQ ID NO:14, amino acid residues at positions 133 to 162 of SEQ ID NO:14, or amino acid residues at positions 99 to 162 of SEQ ID NO:14.

Z2 can comprise 4 to 37, 6 to 30, 6 to 12, 6 to 8, 8 or 6 consecutive amino acid residues of the N-terminal region of the human IgG2 CH2 domain (the amino acid residues at positions 111 to 147 of SEQ ID NO:12) or the N-terminal region of the IgD CH2 domain (the amino acid residues at positions 163 to 199 of SEQ ID NO:14). In certain embodiments, Z2 can be 6 N-terminal amino aid residues of a human IgG2 CH2 domain (amino acid residues 111-116 of SEQ ID NO:12) or 8 N-terminal amino acid residues of a human IgD CH2 domain (amino acid residues 163-170 of SEQ ID NO:14).

The total number of amino acid residues of Z2 and Z3 can be between 90 and 120, both inclusive, or 105 and 115, both inclusive.

Z4 can be an amino acid sequence including 90 or more, or 100 or more consecutive amino acid residues of the IgG4 CH3 domain (amino acid residues at positions 224-330 of SEQ ID NO:11, 220-326 of SEQ ID NO:12, 271-377 of SEQ ID NO:24, or 221 to 327 of SEQ ID NO:13). Z4 can be of amino acid residues of more than 98% or 95% of the amino acid residues of the human IgG1, IgG2, IgG3, or IgG4 CH3 domain. In one exemplary embodiment, Z4 is an amino acid sequence comprising the entire amino acid sequence of the human IgG CH3 domain. For example, Z4 is the amino acid sequence of the human IgG4 CH3 domain, corresponding to amino acid residues 341-447 of the human IgG4, as numbered according to the EU Index, Kabat (which correspond to amino acid residues at positions 221-327 of SEQ ID NO:13).

In one embodiment, Y can be an amino acid sequence including at least a portion of the C-terminal amino acid residues of the human IgG1 hinge region (amino acid residues 99-113 of SEQ ID NO: 11), p can be 1 or 0, Z2 can be an amino acid sequence including at least a portion of the N-terminal region of the human IgG2 CH2 (amino acid residues at positions 111-147 of SEQ ID NO: 12), and Z3 can be an amino acid sequence including at least a portion of the C-terminal region of any of the human IgG subclasses (amino acid residues at positions 118-223 of SEQ ID NO: 11, 114-219 of SEQ ID NO: 12, 165-270 of SEQ ID NO: 24, or 115 to 220 of SEQ ID NO: 13). In this embodiment, when p is 1, Z1 can be an amino acid sequence including at least a portion of the C-terminal region of the human IgG1 CH1 domain (amino acid residues at positions 90 to 98 of SEQ ID NO: 11). For example, Z1 can be the amino acid residues 90 to 98 of SEQ ID NO: 11.

In further embodiments, Z3 can be 73 to 106 consecutive amino acid residues of the C-terminal region of the human IgG4 CH2 domain (positions 115-220 of SEQ ID NO: 13), of the human IgG1 CH2 domain (positions 118-223 of SEQ ID NO: 11), of the human IgG2 CH2 domain (positions 114-219 of SEQ ID NO: 12), of the human IgG3 CH2 domain (positions 165-270 of SEQ ID NO: 24), and the total number of the amino acid residues of Z2 and Z3 can be 110. For example, Z2 can be an amino acid sequence of the amino acid residues at positions 111-116 of SEQ ID NO: 12, and Z3 can be an amino acid sequence of the amino acid residues at positions 117 to 220 of SEQ ID NO: 13.

In another embodiment, Y can be an amino acid sequence including at least a portion of the C-terminal region of the human IgD hinge region (amino acid residues at positions 99 to 162 of SEQ ID NO: 14), p can be 1 or 0 (zero), Z2 can be an amino acid sequence including at least a portion of the N-terminal region of the human IgD CH2 domain (amino acid residues at positions 163 to 199 of SEQ ID NO: 14), and Z3 can be an amino acid sequence including at least a portion of the C-terminal region of the human IgG4 CH2 domain (amino acid residues at positions 121 to 220 of SEQ ID NO: 13). For example, Y can be the amino acid residues at positions 158 to 162, 133 to 162, or 99 to 162 of SEQ ID NO: 14, Z2 can be the amino acid residues at positions 163 to 170 of SEQ ID NO: 14, and Z3 can be amino acid residues at positions 121-220 of SEQ ID NO: 13.

In this embodiment, when p is 1, Z1 can be an amino acid sequence including the C-terminal region of the human IgD CH1 domain (amino acid residues at positions 90 to 98 of SEQ ID NO: 14). For example, Z1 can be amino acid residues 90 to 98 of SEQ ID NO: 14.

In this embodiment, Y can be 20 consecutive amino acid residues or more, 30 consecutive amino acid residues or more, 40 consecutive amino acid residues or more, 50 consecutive amino acid residues or more, or 60 consecutive amino acid residues or more of the C-terminal side of the human IgD hinge region (amino acid residues at positions 99-162 of SEQ ID NO: 14). Z3 can comprise 71 to 100 consecutive amino acid residues of the C-terminal side of the amino acid residues at positions 121-220 of SEQ ID NO: 13. The total number of the amino acid residues for Z2 and Z3 can be 108.

Table 1 shows amino acid sequences of the fragments of human IgG1, IgG2, IgG3 and IgD useful in the construction of the hFcs according to the embodiments of the present invention.

TABLE 1

| hFc domain | Acceptable range of the Ig fragments | Sequence of the longest fragments within the acceptable range, in an N-terminal to C-terminal direction | SEQ ID NO: | Location in the SEQ ID | Location in the EU index* |
|---|---|---|---|---|---|
| CH1 (Z1) | 5-9 C-terminal amino acid residues of IgG1 CH1 | SNTK▓▓▓▓** | 11 | 90-98 | 207-215 |
| | 5-9 C-terminal amino acid residues of IgD CH1 | ASKS▓▓▓▓ | 14 | 90-98 | Not Available |
| Hinge (Y) | 5-15 C-terminal amino acid residues of IgG1 hinge region | EPKSCDKTHT▓▓▓▓ | 11 | 99-113 | 216-230 |
| | 5-64 C-terminal amino acid residues of IgD hinge region | RWPESPKAQASSVPTAQP QAEGSLAKATTAPATTR NTGRGGEEKKKEKEKEE QEERETK▓▓▓▓ | 14 | 99-162 | Not Available |
| CH2, N-terminal side (Z2) | 4-37 N-terminal amino acid residues of IgG2 CH2 | ▓▓▓▓AGPSVFLFPPKPKD TLMISRTPEVTWVVVDV SH | 12 | 111-147 | 231-267 |
| | 4-37 N-terminal amino acid residues of IgG2 CH2 domain | ▓▓▓▓PLGVYLLTPAVQD LWLRDKATFTCFVVGSD LKD | 14 | 163-199 | Not Available |

TABLE 1-continued

| hFc domain | Acceptable range of the Ig fragments | Sequence of the longest fragments within the acceptable range, in an N-terminal to C-terminal direction | SEQ ID NO: | Location in the SEQ ID | Location in the EU index* |
|---|---|---|---|---|---|
| CH2, C-terminal side (Z3) + | 71-106 C-terminal amino acid residues of IgG4 CH2 + | LGGPSVFLFPPKPKDTLM ISRTPEVTCVVVDVSQED PEVQFNWYVDGVEVHN AKTKPREEQFNSTYRVVS VLTVLHQDWLNGKEYK CKVSNKGLPSSIEKTISKA K + | 13 | 115-220 + 221-327 | 235-340 + 341-447 |
| CH3 (Z4) | 8-107 N-terminal amino acid residues of IgG4 CH3 domain | GQPREPQVYTLPPSQEEM TKNQVSLTCLVKGFYPS DIAVEWESNGQPENNYK TTPPVLDSDGSFFLYSRL TVDKSRWQEGNVFSCSV MHEALHNHYTQKSLSLS LGK | | | |
| | 71-106 C-terminal amino acid residues of IgG3 CH2 + | LGGPSVFLFPPKPKDTLM ISRTPEVTCVVVDVSHED PEVQFKWYVDGVEVHN AKTKPREEQYNSTFRVVS VLTVLHQDWLNGKEYK CKVSNKALPAPIEKTISKT K + | 24 | 165-270 + 271-377 | 235-340 + 341-447 |
| | 80-107 N-terminal amino acid residues of IgG3 CH3 domain | GQPREPQVYTLPPSREEM TKNQVSLTCPVKGFYPSD IAVEWESSGQPENNYNTT PPMLDSDGSFFLYSKLTV DKSRWQQGNIFSCSVMH EALHNRFTQKSLSLSPGK | | | |
| | 71-106 C-terminal amino acid residues of IgG2 CH2 + | VAGPSVFLFPPKPKDTLM ISRTPEVTVVVDVSHE DPEVQFNWYVDGVEVH NAKTKPREEQFNSTFCVV SVLTVVHQDWLNGKEY KCKVSNKGLPAPIEKTIS KTK + | 12 | 114-219 + 220-326 | 234-340 + 341-447 |
| | 80-107 N-terminal amino acid residues of IgG2 CH3 domain | GQPREPQVYTLPPSREEM TKNQVSLTCLVKGFYPS DIAVEWESNGQPENNYK TTPPMLDSDGSFFLYSKL TVDKSRWQQGNVFSCSV MHEALHNHYTQKSLSLS PGK | | | |
| | 71-106 C-terminal amino acid residues of IgG1 CH2 + | LGGPSVFLFPPKPKDTLM ISRTPEVTCVVVDVSHED PEVKFNWYVDGVEVHN AKTKPREEQYNSTYRVV SVLTVLHQDWLNGKEYK CKVSNKALPAPIEKTISK AK + | 11 | 118-223 + 224-330 | 235-340 + 341-447 |
| | 80-107 N-terminal amino acid residues of IgG1 CH3 domain | GQPREPQVYTLPPSRDEL TKNQVSLTCLVKGFYPS DIAVEWESNGQPENNYK TTPPVLDSDGSFFLYSKL TVDKSRWQQGNVFSCSV MHEALHNHYTQKSLSLS PGK | | | |

*EU index is described in "Sequences of Proteins of Immunological Interest, 5th Edition, United States Department of Health and Human Services."
**The shaded region in each of the amino acid sequence indicates the shortest fragments of the acceptable amino acid residue ranges.

Figure 1:
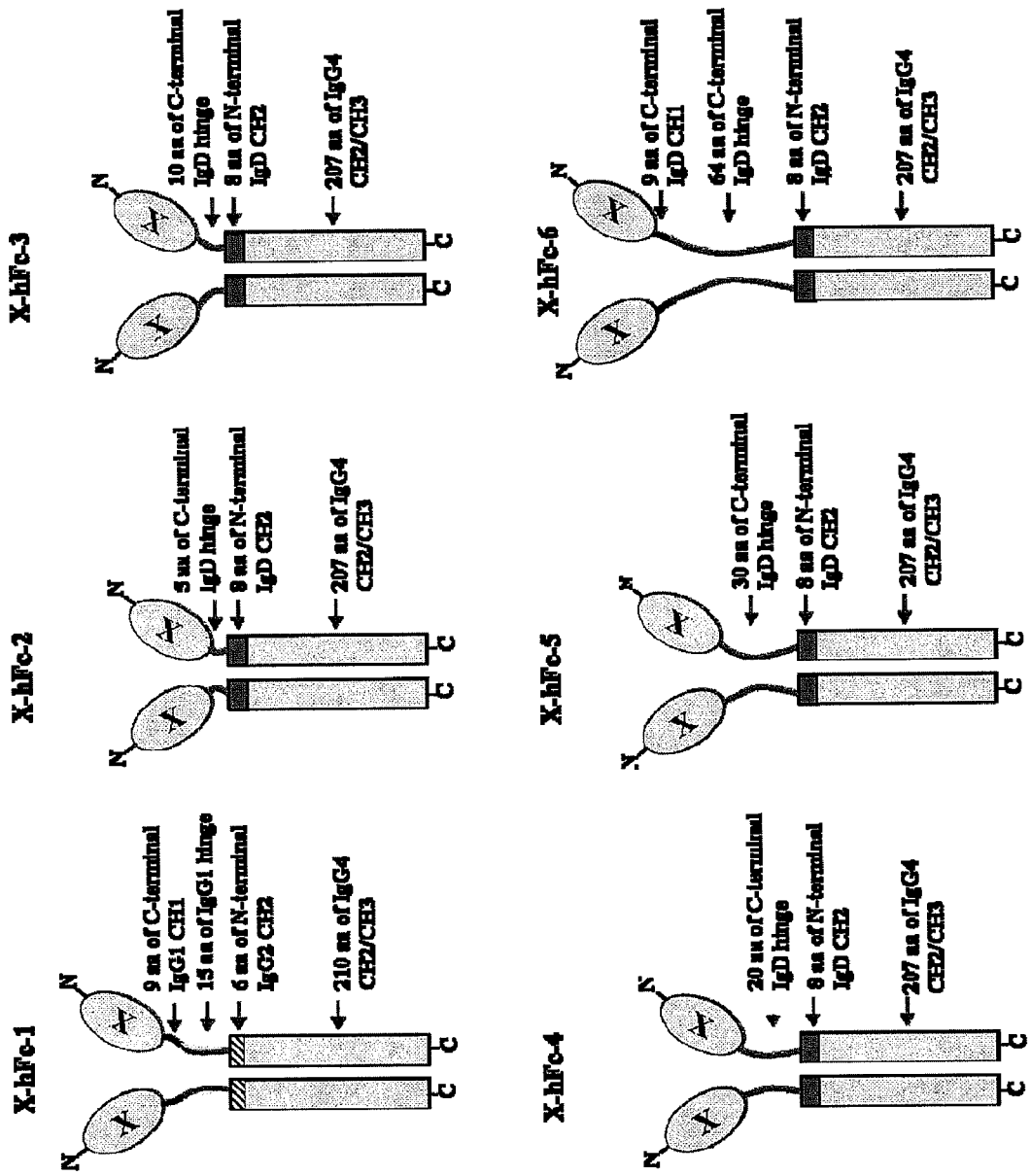
FIG. 1 shows the schematic diagram of hybrid Fcs (hFcs) that can be used as a carrier protein for biologically active molecules designated as "X".
Figure 2:
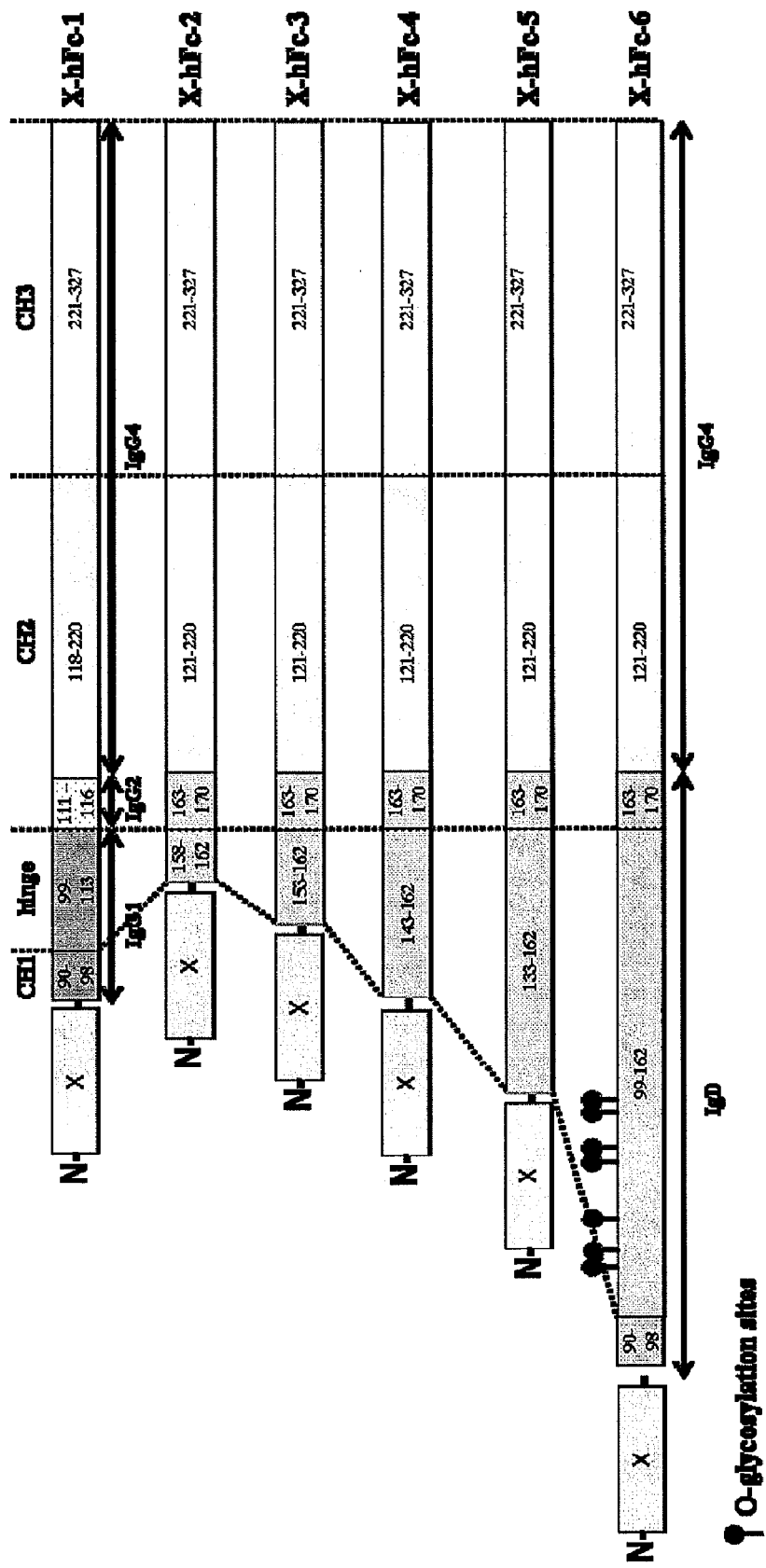
FIG. 2 shows the schematic representations of hFcs following detailed description about amino acid positions derived from IgG1 (SEQ ID NO: 11), IgG2 (SEQ ID: 12), IgG4 (SEQ ID: 13) and IgD (SEQ ID: 14). The same rule applies to the designation of amino acid positions in the polypeptide throughout the application, unless otherwise indicated.
Figure 3:
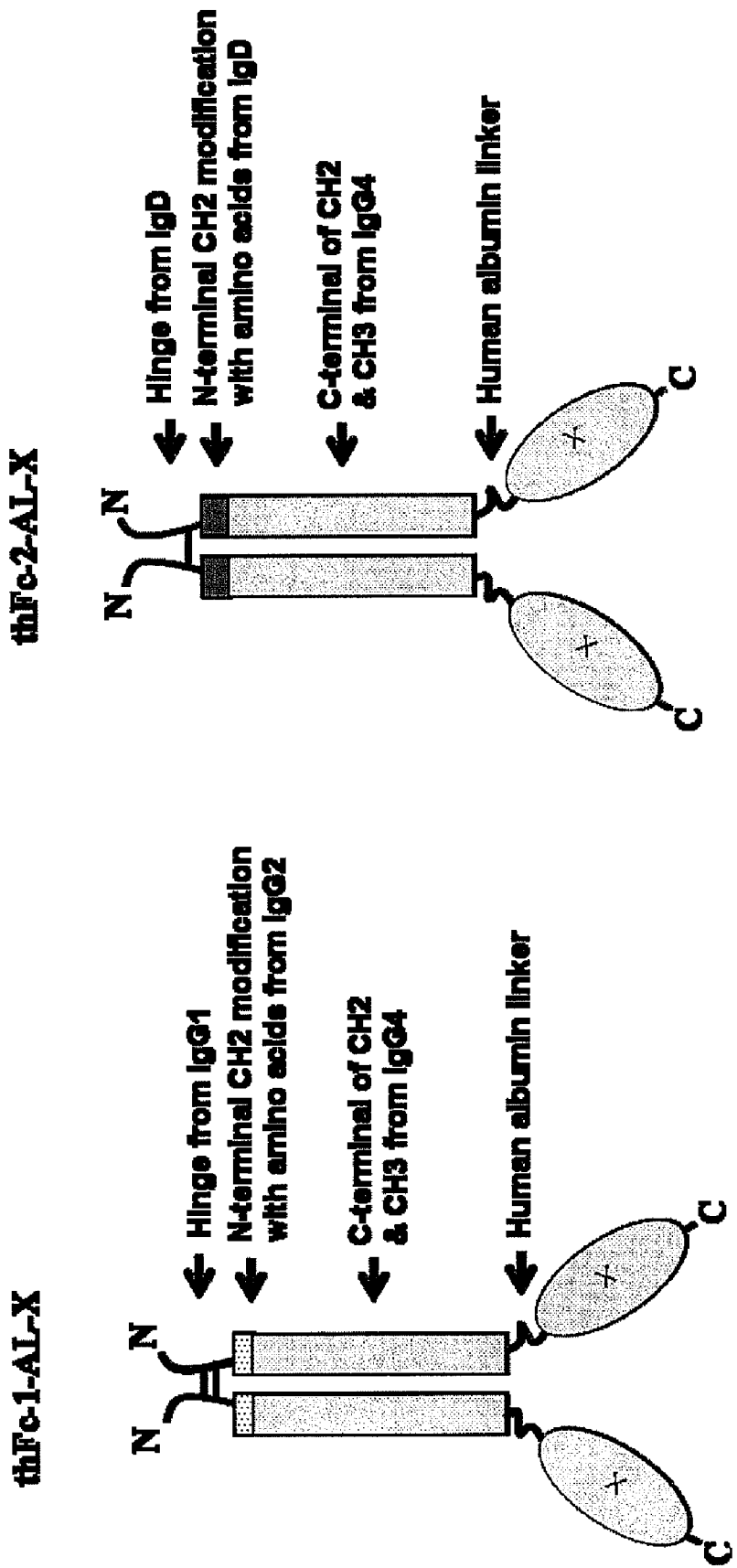
FIG. 3 shows the schematic representation of hFcs which each are conjugated to biologically active molecules designated as "X" at the C-terminal through an albumin linker peptide designated as "AL".
Figure 4:
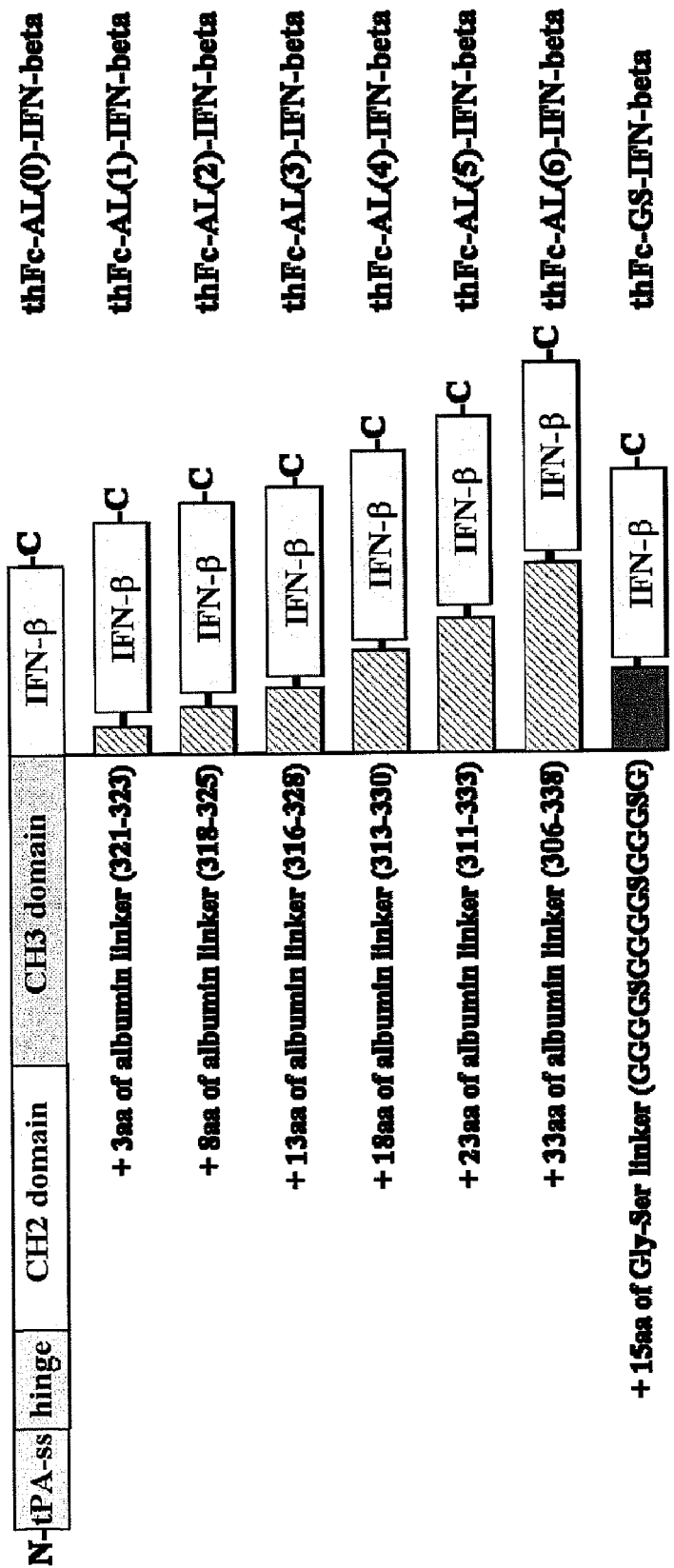
FIG. 4 shows the schematic representations of hFcs conjugated with linkers following detailed description about amino acid positions of albumin linkers derived from human albumin (SEQ ID NO:25).
Figure 5:
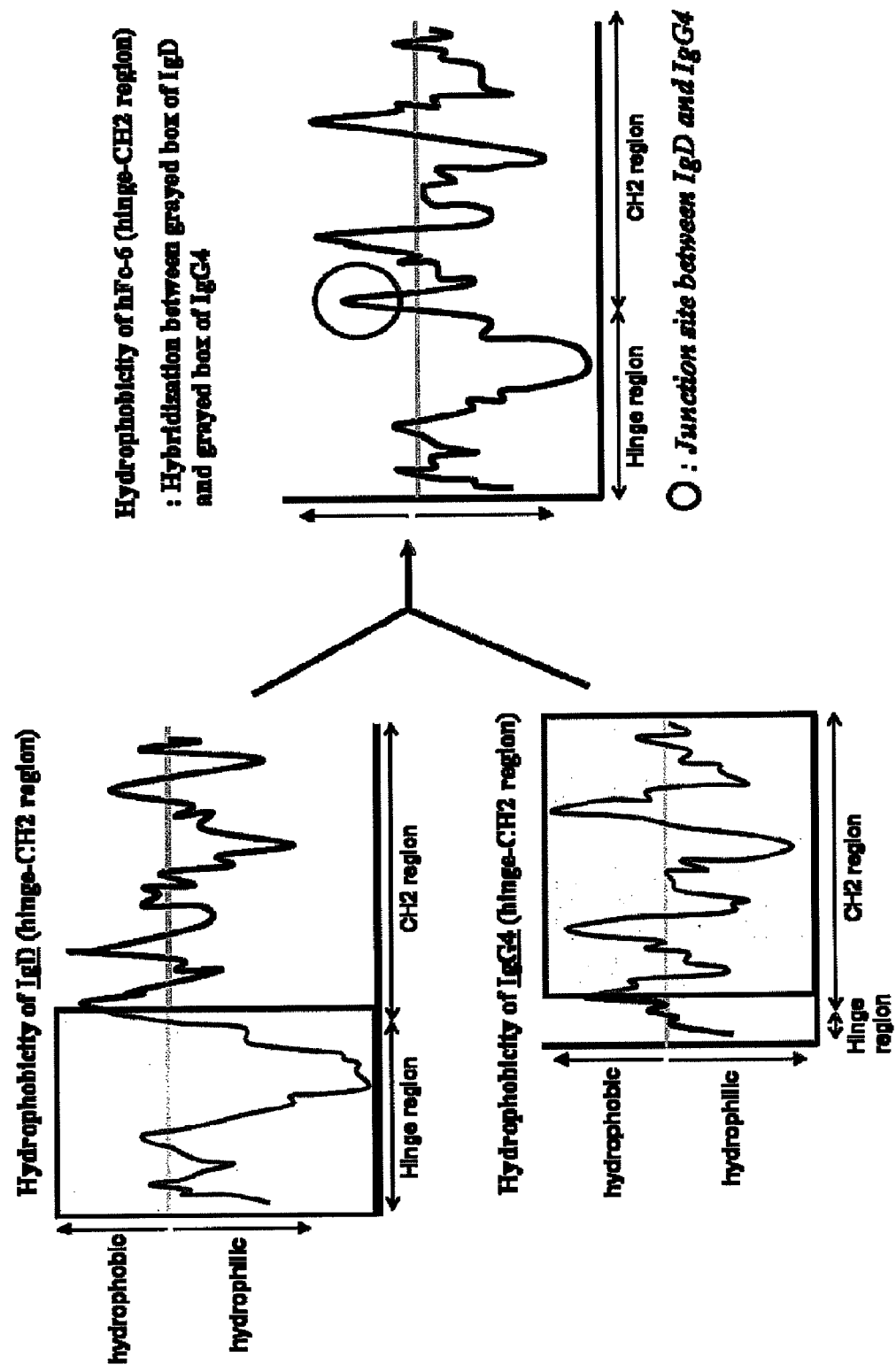
FIG. 5 shows the results of hydrophobicity plot of hFc-6.

In an embodiment, the present invention provides a hybrid Fc which is one of hFc-1, hFc-2, hFc-3, hFc-4, hFc-5, or hFc-6, as shown in FIGS. 1 and 2, or thFc-1 or thFc-2 as shown in FIGS. 3 and 4. Although FIGS. 1 and 3 depict double chain Fcs, the present invention encompasses single chain hybrid Fc molecules. Amino acid sequences of hFc-1 to hFc-6 are shown in SEQ ID NOs: 18-23, respectively and amino acid sequences of thFc-1 and thFc-2 are shown in SEQ ID NO: 28 and SEQ ID NO: 29, respectively. The present invention also encompasses a polynucleotide molecule coding for the hybrid Fc. They include, but are not limited to, a polynucleotide sequence as shown as SEQ ID NO: 1 (hFc-1), SEQ ID NO: 2 (hFc-2), SEQ ID NO: 3 (hFc-3), SEQ ID NO: 4 (hFc-4), SEQ ID NO: 5 (hFc-5), SEQ ID NO: 6 (hFc-6), SEQ ID NO: 26 (thFc-1) and SEQ ID NO: 27 (thFc-2).

The amino acid sequences of human immunoglobulins are known in the art and they are deposited with a publicly accessible depository. For example, amino acid sequences of human IgG1 constant region, human IgG2 constant region, human IgG3 constant region, human IgG4 constant region, and human IgD constant region are available at CAA75032, CAC20455, CAC20456, AAH25985 and P01880, respectively. These sequences are reproduced as SEQ ID NO: 11, 12, 24, 13 and 14, respectively.

A biologically active molecule X may be a soluble protein. It may include, but is not limited to, a hormone, cytokine, growth factor, co-stimulatory molecule, hormone receptor, cytokine receptor, growth factor receptor, or short peptide. For example, X may be an EPO, p40, G-CSF, TNF receptor or variants/fragments thereof X may be a GM-CSF, IL-1, IL-2, IL-3, IL-4, IL-5, IL-6, IL-7, IL-8, IL-10, IL-10 receptor, TGF-beta, TGF-beta receptor, IL-17, IL-17 receptor, Factor VII, CXCL-11, FSH, human growth hormone, bone morphogenetic protein-1, CTLA4, PD-1, GLP-1, betacellulin, OPG, RNAK, interferon-alpha, interferon-beta or their variants/fragments. It also may include, but is not limited to, a Fab region of an antibody. The biologically active molecule also may be a secreted protein. In one embodiment, the biologically active molecule does not belong to the immunoglobulin family.

The term "variant" refers to a polynucleotide or nucleic acid differing from a reference nucleic acid or polypeptide, but retaining essential properties thereof Generally, variants are overall closely similar, and, in many regions, identical to the reference nucleic acid or polypeptide. Also, the term "variant" refers to a biologically active portion of a biologically active molecule drug, and retaining at least one functional and/or therapeutic property thereof as described elsewhere herein or otherwise known in the art. Generally, variants are overall very similar, and, in many regions, identical to the amino acid sequence of the biologically active polypeptide of interest.

The present invention also provides proteins which comprise, or alternatively consist of, an amino acid sequence which is at least 80%, 85%, 90%, 95%, 96%, 97%, 98%, 99% or 100%, identical to, for example, the amino acid sequence of the polypeptides, as shown in SEQ ID NOs: 18-23 and 28-29. Fragments of these polypeptides are also provided. Further polypeptides encompassed by the invention are polypeptides encoded by polynucleotides which hybridize to the complement of a nucleic acid molecule encoding the polypeptides of the invention under stringent hybridization conditions (e.g., hybridization to filter bound DNA in 6× Sodium chloride/Sodium citrate (SSC) at about 45° C. followed by one or more washes in 0.2×SSC, 0.1% SDS at about 50-65° C.), under highly stringent conditions (e.g., hybridization to filter bound DNA in 6× sodium chloride/Sodium citrate (SSC) at about 45° C., followed by one or more washes in 0.1×SSC, 0.2% SDS at about 68° C.), or under other stringent hybridization conditions which are known to those of skill in the art (see, for example, Ausubel, F. M. et al., eds., 1989 Current protocol in Molecular Biology, Green publishing associates, Inc., and John Wiley & Sons Inc., New York, at pages 6.3.1 6.3.6 and 2.10.3). Polynucleotides encoding these polypeptides are also encompassed by the invention.

By a polypeptide having an amino acid sequence at least, for example, 95% "identical" to a query amino acid sequence, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, or substituted with another amino acid. These alterations of the reference sequence may occur at the amino- or carboxy-terminal positions of the reference amino acid sequence or anywhere between those terminal positions, interspersed either individually among residues in the reference sequence or in one or more contiguous groups within the reference sequence.

As a practical matter, whether any particular polypeptide is at least 80%, 85%, 90%, 95%, 96%, 97%, 98% or 99% identical to, for instance, the amino acid sequence of an albumin fusion protein of the invention or a fragment thereof, can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. 6:237 245 (1990)). In a sequence alignment the query and subject sequences are either both nucleotide sequences or both amino acid sequences. The result of the global sequence alignment is expressed as percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter.

The variant will usually have at least 75% (preferably at least about 80%, 90%, 95% or 99%) sequence identity with a length of normal HA or Therapeutic protein which is the same length as the variant. Homology or identity at the nucleotide or amino acid sequence level is determined by BLAST (Basic Local Alignment Search Tool) analysis using the algorithm employed by the programs blastp, blastn, blastx, tblastn and tblastx (Karlin et al., Proc. Natl. Acad. Sci. USA 87: 2264 2268 (1990) and Altschul, J. Mol. Evol. 36: 290 300 (1993), fully incorporated by reference) which are tailored for sequence similarity searching.

The polynucleotide variants of the invention may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, polypeptide variants in which less than 50, less than 40, less than 30, less than 20, less than 10, or 5-50, 5-25, 5-10, 1-5, or 1-2 amino acids are substituted, deleted, added in any combination are also preferred. Polynucleotide variants can be produced for a variety of reasons, e.g., to optimize codon expression for a particular host (change codons in the human mRNA to those preferred by a bacterial host, such as, yeast or E. coli).

For the purpose of constructing various Fc fusion proteins such as EPO-Fc fusion construct, G-CSF-Fc fusion construct, or human p40-Fc fusion construct, amino acid sequences of the human EPO, human G-CSF, human p40, and human TNF receptor are available from NP_000790 (SEQ ID NO: 15), CAA27291(SEQ ID NO: 16), AAG32620 (SEQ ID NO: 17), and NP_001057 (SEQ ID NO: 31), respectively. In one embodiment, a modified human p40 wherein amino acid residue Asn at position 303 is replaced with Gln is connected to the polypeptide.

According to another aspect of the present invention, a whole antibody containing the engineered Fc region is provided. The term "antibody" as used herein includes whole antibodies and antibody fragments that include at least two of CH1, hinge region, CH2 or CH3. Whole monoclonal antibodies are preferred. The heavy chain variable region of the antibody is selected for its binding specificity and can be of any type, such as, for example, non-human, humanized or fully human. Where the heavy chain variable region of the antibody is non-human (such as, for example, murine) and is combined recombinantly with an engineered Fc region in accordance with this disclosure, the resulting recombinant antibody is referred to as a chimeric antibody. Where the heavy chain variable region of the antibody is humanized and is combined recombinantly with an engineered Fc region in accordance with this disclosure, the resulting recombinant antibody is referred to as a humanized antibody. Where the heavy chain variable region of the antibody is human and is combined recombinantly with an engineered Fc region in accordance with this disclosure, the resulting recombinant antibody is referred to as a fully human antibody. For example, the variable region of the heavy chain is humanized and includes human framework regions and non-human (in this case murine) complementary determining regions (CDRs). It should be understood that the framework regions can be derived from one source or more than one source and that the CDRs can be derived from one source or more than one source. Methods for humanization of antibodies are known to those skilled in the art and are known in the art.

The light chain of the antibody can be human, non-human or humanized. In the embodiment shown in FIG. 1B, the light chain is humanized and includes human framework regions, non-human (in this case murine) CDRs and a human constant region. It should be understood that the framework regions can be derived from one source or more than one source and that the CDRs can be derived from one source or more than one source.

The antibody containing the engineered Fc region is selected based on its ability to bind to a cell surface molecule or a soluble molecule that binds to a cell surface molecule. Thus, for example, the antibody can be selected based on its ability to bind cell surface molecules such as cytokine receptors (e.g., IL-2R, TNF-aR, IL-15R, etc.); adhesion molecules (e.g., E-selectin, P-selectin, L-selectin, VCAM, ICAM, etc.); cell differentiation or activation antigens (e.g., CD3, CD4, CD8, CD20, CD25, CD40, etc.), and others. Alternatively, the antibody can be selected based on its ability to bind a soluble molecule that binds to cell surface molecules. Such soluble molecules include, but are not limited to, cytokines and chemokines (e.g., interleukin-1 (IL-1), IL-2, IL-3, IL-5, IL-6, etc.); growth factors (e.g., EGF, PGDF, GM-CSF, HGF, IGF, BMP-1, etc.); molecules inducing cell differentiation (e.g., EPO, TPO, SCF, PTN, etc.), and others.

In general, the construction of the antibodies disclosed herein is achieved by, using recognized manipulations utilized in genetic engineering technology. For example, techniques for isolating DNA, making and selecting vectors for expressing the DNA, purifying and analyzing nucleic acids, specific methods for making recombinant vector DNA, cleaving DNA with restriction enzymes, ligating DNA, introducing DNA including vector DNA into host cells by stable or transient means, culturing the host cells in selective or non-selective media to select and maintain cells that express DNA, are generally known in the field.

The monoclonal antibodies disclosed herein may be derived using the hybridoma method, which is known in the art, or other recombinant DNA methods well known in the art. In the hybridoma method, a mouse or other appropriate host animal is immunized with DNA, peptide or protein which elicits the production of antibodies by the lymphocytes.

Alternatively, lymphocytes may be immunized in vitro. The lymphocytes produced in response to the antigen are then are fused with myeloma cells using a suitable fusing agent, such as polyethylene glycol, to form a hybridoma cell. The hybridoma cells are then seeded and grown in a suitable culture medium that preferably contains one or more substances that inhibit the growth or survival of the unfused, parental myeloma cells. Preferred myeloma cells are those that fuse efficiently, support stable production of antibody by the selected antibody-producing cells, and are not sensitive to a medium such as HAT medium (Sigma Chemical Company, St. Louis, Mo., Catalog No. H-0262).

The antibodies containing the engineered Fc region can also be used as separately administered compositions given in conjunction with therapeutic agents. For diagnostic purposes, the antibodies may either be labeled or unlabeled.

Unlabeled antibodies can be used in combination with other labeled antibodies (second antibodies) that are reactive with the engineered antibody, such as antibodies specific for human immunoglobulin constant regions. Alternatively, the antibodies can be directly labeled. A wide variety of labels may be employed, such as radionuclides, fluors, enzymes, enzyme substrates, enzyme co-factors, enzyme inhibitors, ligands (particularly haptens), etc. Numerous types of immunoassays are available and are well known to those skilled in the art.

According to one embodiment, the present invention provides a method of producing the fusion protein, which method comprises: (i) introducing a DNA molecule coding for the fusion protein into a mammalian host cell, (ii) growing the cell under conditions the fusion protein is expressed in its growth medium; and (iii) harvesting the produced fusion protein.

In another exemplary embodiment, there is provided a pharmaceutical composition comprising the fusion protein or an antibody molecule or an antibody fragment described above. It also provides a method of treating or preventing certain symptoms by administering the pharmaceutical composition. For example, a method is provided, which (i) reduces the symptoms of preventing/treating an autoimmune disease, (ii) inhibits rejection of a graft, (iii) treats/prevents endotoxin-induced shock, comprising administering a therapeutically effective amount of the fusion protein of the hybrid Fc and a p40 protein or its variants/fragments.

The composition may comprises a pharmaceutical carrier. A pharmaceutical carrier can be any compatible, non-toxic substance suitable for delivery of the antibodies to the patient. Sterile water, alcohol, fats, waxes, and inert solids may be included in the carrier. Pharmaceutically accepted adjuvants (buffering agents, dispersing agent) may also be incorporated into the pharmaceutical composition.

The antibody compositions may be administered to a subject in a variety of ways. For example, the pharmaceutical compositions may be administered parenterally, e.g., subcutaneously, intramuscularly or intravenously. These compositions may be sterilized by conventional, well known sterilization techniques. The compositions may contain pharmaceutical acceptable auxiliary substances as required to approximate physiological conditions such as pH adjusting and buffering agents, toxicity adjusting agents and the like, for example sodium acetate, sodium chloride, potassium chloride, calcium chloride, sodium lactate, etc. The concentration of the fusion protein, antibody, or antibody fragment in these formulations can vary widely, e.g., from less than about 0.5%, usually at or at least about 1% to as much as 15 or 20% by weight and will be selected primarily based on fluid volumes, viscosities, etc., in accordance with the particular mode of administration selected.

The present invention also provides an isolated nucleic acid molecule which encodes for the fusion protein, and an expression vector carrying the nucleic acid molecule. Such nucleic acid may be directly delivered to a subject which needs a polypeptide encoded by the nucleic acid. Alternatively, the polynucleotide is produced by expressing the nucleic acid in a medium and then administered to a subject.

The term "peptide," "polypeptide" or "protein" refers to molecules of 2 to 40 amino acids, with molecules of 3 to 20 amino acids preferred and those of 6 to 15 amino acids most preferred. Exemplary peptides may be randomly generated by any of the methods cited above, carried in a peptide library (e.g., a phage display library), or derived by digestion of proteins.

The term "drug", as used herein, refers to a substance displaying therapeutic activity when administered to humans or animals, and examples of the drug include, but are not limited to, polypeptides, compounds, extracts and nucleic acids. Preferred is a polypeptide drug.

The terms "physiologically active polypeptide," "biologically active molecule," "physiologically active protein," "active polypeptide," "polypeptide drug," and "protein drug", as used herein, are interchangeable in their meanings, and are featured in that they are in a physiologically active form exhibiting various in vivo physiological functions.

The polypeptide drug has a disadvantage of being unable to sustain physiological action for a long period of time due to its property of being easily denatured or degraded by proteolytic enzymes present in the body. However, when the polypeptide drug is joined (or coupled) to the immunoglobulin Fc fragments according to embodiments of the present invention to form a fusion protein, the drug has increased structural stability and serum half-life. Also, the polypeptide joined to the Fc fragment has a much smaller decrease in physiological activity than other known polypeptide drug formulations. Therefore, compared to the in vivo bioavailability of conventional polypeptide drugs, the fused polypeptide comprising the polypeptide drug and the Fc fragment, or a conjugate of the polypeptide drug and the Fc fragment according to the present invention is characterized by having markedly improved in vivo bioavailability. This is also clearly described through embodiments of the present invention. That is, when joined to the Fc fragment of the present invention, IFN-α, G-CSF, EPO, p40, TNF receptor, and other protein drugs displayed an increase in vivo bioavailability compared to their native forms or other conventional fused forms.

It is understood that the present invention exploits conventional recombinant DNA methodologies for generating the Fc fusion proteins, antibodies containing engineered Fc region according to the present invention and antibody fragments useful in the practice of the invention. The Fc fusion constructs preferably are generated at the DNA level, and the resulting DNAs integrated into expression vectors, and expressed to produce the fusion proteins, antibody or antibody fragment of the invention.

As used herein, the term "vector" is understood to mean any nucleic acid including a nucleotide sequence competent to be incorporated into a host cell and to be recombined with and integrated into the host cell genome, or to replicate autonomously as an episome. Such vectors include linear nucleic acids, plasmids, phagemids, cosmids, RNA vectors, viral vectors and the like. Non-limiting examples of a viral vector include a retrovirus, an adenovirus and an adeno-associated virus. As used herein, the term "gene expression" or "expression" of a target protein, is understood to mean the transcription of a DNA sequence, translation of the mRNA transcript, and secretion of an Fc fusion protein product or antibody or antibody fragment.

A useful expression vector is RcCMV (Invitrogen, Carlsbad) or variants thereof The useful expression vector should carry human cytomegalovirus (CMV) promoter to promote constitute transcription of the interest gene in mammalian cells and carry bovine growth hormone polyadenylation signal sequence to increase steady state level of RNA after transcription. In an embodiment of the present invention, the expression vector is pAD11, which is a modified vector of RcCMV. Examples of the expression vector carrying a nucleotide sequence coding for a biologically active molecule drug may include, not is limited to, pAD11 EPO-hFc-1, pAD11 G-CSF-hFc-1, pAD11 p40N303Q-hFc-1, pAD11 EPO-hFc-6, pAD11 G-CSF-hFc-6, pAD11 p40N303Q-hFc-6, pAD11 EPO-hFc-5, pAD11 G-CSF-hFc-5, pAD11 p40N303Q-hFc-5 or pAD11 TNFR-hFc-5, as described in more detail in Examples.

An appropriate host cell can be transformed or transfected with the DNA sequence of the invention, and utilized for the expression and/or secretion of the target protein. Currently preferred host cells for use in the invention include immortal hybridoma cells, NS/0 myeloma cells, 293 cells, Chinese hamster ovary cells, HeLa cells, and COS cells.

One expression system that has been used to produce high level expression of fusion proteins or antibody or antibody fragment in mammalian cells is a DNA construct encoding, in the 5' to 3' direction, a secretion cassette, including a signal sequence and an immunoglobulin Fc region, and a target protein such as p40, EPO, G-CSF, TNF receptor. Several target proteins have been expressed successfully in such a system and include, for example, IL2, CD26, Tat, Rev, OSF-2, ss; IG-H3, IgE Receptor, PSMA, and gp120. These expression constructs are disclosed in U.S. Pat. Nos. 5,541,087 and 5,726,044 to Lo et al., contents of which are incorporated herein by reference.

The fusion proteins or antibody molecule or antibody fragments of the invention may or may not be include a signal sequence when expressed. As used herein, the term "signal sequence" is understood to mean a segment which directs the secretion of the biologically active molecule drug; fusion protein and thereafter is cleaved following translation in the host cell. The signal sequence of the invention is a polynucleotide which encodes an amino acid sequence which initiates transport of a protein across the membrane of the endoplasmic reticulum. Signal sequences which are useful in the invention include antibody light chain signal sequences, e.g., antibody 14.18 (Gillies et al., J. Immunol. Meth. 1989. 125: 191-202), antibody heavy chain signal sequences, e.g., the MOPC141 antibody heavy chain signal sequence (Sakano et al., Nature 1980. 286: 676-683), and any other signal sequences which are known in the art (see, e.g., Watson et al., Nucleic Acids Research 1984. 12:5145-5164).

Signal sequences have been well characterized in the art and are known typically to contain 16 to 30 amino acid residues, and may contain greater or fewer amino acid residues. A typical signal peptide consists of three regions: a basic N-terminal region, a central hydrophobic region, and a more polar C-terminal region. The central hydrophobic region contains 4 to 12 hydrophobic residues that anchor the signal peptide across the membrane lipid bilayer during transport of the nascent polypeptide. Following initiation, the signal peptide is usually cleaved within the lumen of the endoplasmic reticulum by cellular enzymes known as signal peptidases. Potential cleavage sites of the signal peptide generally follow the "(−3,−1) rule." Thus a typical signal peptide has small, neutral amino acid residues in positions-1 and -3 and lacks proline residues in this region.

The signal peptidase will cleave such a signal peptide between the −1 and +1 amino acids. Thus, the signal sequence may be cleaved from the amino-terminus of the fusion protein during secretion. This results in the secretion of an Fc fusion protein consisting of the immunoglobulin Fc region and the target protein. A detailed discussion of signal peptide sequences is provided by von Heijne (1986) Nucleic Acids Res. 14:4683.

As would be apparent to one of skill in the art, the suitability of a particular signal sequence for use in the secretion cassette may require some routine experimentation.

Such experimentation will include determining the ability of the signal sequence to direct the secretion of an Fc fusion protein and also a determination of the optimal configuration, genomic or cDNA, of the sequence to be used in order to achieve efficient secretion of Fc fusion proteins. Additionally, one skilled in the art is capable of creating a synthetic signal peptide following the rules presented by von Heijne (1986), and testing for the efficacy of such a synthetic signal sequence by routine experimentation. A signal sequence can also be referred to as a "signal peptide," "leader sequence," or "leader peptides."

The fusion of the signal sequence and the immunoglobulin Fc region is sometimes referred to as secretion cassette. An exemplary secretion cassette useful in the practice of the invention is a polynucleotide encoding, in a 5' to 3' direction, a signal sequence of an immunoglobulin light chain gene and an Fcγ1 region of the human immunoglobulin γ1 gene. The Fcγ1 region of the immunoglobulin Fcγ1 gene preferably includes at least a portion of the immunoglobulin hinge domain and at least the CH3 domain, or more preferably at least a portion of the hinge domain, the CH2 domain and the CH3 domain. As used herein, the "portion" of the immunoglobulin hinge region is understood to mean a portion of the immunoglobulin hinge that contains at least one, preferably two cysteine residues capable of forming interchain disulfide bonds. The DNA encoding the secretion cassette can be in its genomic configuration or its cDNA configuration. Under certain circumstances, it may be advantageous to produce the Fc region from human immunoglobulin Fcγ2 heavy chain sequences. Although Fc fusions based on human immunoglobulin γ1 and γ2 sequences behave similarly in mice, the Fc fusions based on the γ2 sequences can display superior pharmacokinetics in humans.

In another embodiment, the DNA sequence encodes a proteolytic cleavage site interposed between the secretion cassette and the target protein. A cleavage site provides for the proteolytic cleavage of the encoded fusion protein thus separating the Fc domain from the target protein. As used herein, "proteolytic cleavage site" is understood to mean amino acid sequences which are preferentially cleaved by a proteolytic enzyme or other proteolytic cleavage agents. Useful proteolytic cleavage sites include amino acids sequences which are recognized by proteolytic enzymes such as trypsin, plasmin or enterokinase K. Many cleavage site/cleavage agent pairs are known (see, for example, U.S. Pat. No. 5,726,044).

Further, substitution or deletion of constructs of these constant regions, in which one or more amino acid residues of the constant region domains are substituted or deleted also would be useful. One example would be to introduce amino acid substitutions in the upper CH2 region to create an Fc variant with reduced affinity for Fc receptors (Cole et al. (1997) J. Immunol. 159: 3613). One of ordinary skill in the art can prepare such constructs using well known molecular biology techniques.

Non-limiting examples of protein drugs capable of being conjugated to the immunoglobulin Fc fragment of the present invention include human growth hormone, bone morphogenetic protein-1 (BMP-1), growth hormone releasing hormone, growth hormone releasing peptide, interferons and interferon receptors (e.g., interferon-α, -β and -γ, water-soluble type I interferon receptor, etc.), granulocyte colony stimulating factor (G-CSF), granulocyte-macrophage colony stimulating factor (GM-CSF), glucagon-like peptides (e.g., GLP-1, etc.), G-protein-coupled receptor, interleukins (e.g., interleukin-1, -2, -3, -4, -5, -6, -7, -8, -9, -10, -11, -12, -13, -14, -15, -16, -17, -18, -19, -20, -21, -22, -23, -24, -25, -26, -27, -28, -29, -30, etc.) and interleukin receptors (e.g., IL-1 receptor, IL-4 receptor, etc.), enzymes (e.g., glucocerebrosidase, iduronate-2-sulfatase, alpha-galactosidase-A, agalsidase alpha and beta, alpha-L-iduronidase, butyrylcholinesterase, chitinase, glutamate decarboxylase, imiglucerase, lipase, uricase, platelet-activating factor acetylhydrolase, neutral endopeptidase, myeloperoxidase, etc.), interleukin and cytokine binding proteins (e.g., IL-18 bp, TNF-binding protein, etc.), macrophage activating factor, macrophage peptide, B cell factor, T cell factor, protein A, allergy inhibitor, cell necrosis glycoproteins, immunotoxin, lymphotoxin, tumor necrosis factor, tumor suppressors, metastasis growth factor, alpha-1 antitrypsin, albumin, alpha-lactalbumin, apo lipoprotein-E, erythropoietin, highly glycosylated erythropoietin, angiopoietins; hemoglobin, thrombin, thrombin receptor activating peptide, thrombomodulin, factor VII, factor VIa, factor VIII, factor IX, factor XIII, plasminogen activating factor, fibrin-binding peptide, urokinase, streptokinase, hirudin, protein C, C-reactive protein, renin inhibitor, collagenase inhibitor, superoxide dismutase, leptin, platelet-derived growth factor, epithelial growth factor, epidermal growth factor, angiostatin, angiotensin, bone growth factor, bone stimulating protein, calcitonin, insulin, atriopeptin, cartilage inducing factor, elcatonin, connective tissue activating factor, tissue factor pathway inhibitor, follicle stimulating hormone, luteinizing hormone, luteinizing hormone releasing hormone, nerve growth factors (e.g., nerve growth factor, ciliary neurotrophic factor, axogenesis factor-1, brain-natriuretic peptide, glial derived neurotrophic factor, netrin, neurophil inhibitor factor, neurotrophic factor, neuturin, etc.), parathyroid hormone, relaxin, secretin, somatomedin, insulin-like growth factor, adrenocortical hormone, glucagon, cholecystokinin, pancreatic polypeptide, gastrin releasing peptide, corticotropin releasing factor, thyroid stimulating hormone, autotaxin, lactoferrin, myostatin, receptors (e.g., TNFR(P75), TNFR(P55), IL-1 receptor, VEGF receptor, B cell activating factor receptor, etc.), receptor antagonists (e.g., IL1-Ra etc.), cell surface antigens (e.g., CD 2, 3, 4, 5, 7, 11a, 11b, 18, 19, 20, 23, 25, 33, 38, 40, 45, 69, etc.), virus vaccine antigens, monoclonal antibodies, polyclonal antibodies, antibody fragments (e.g., scFv, Fab, Fab', F(ab')2 and Fd), and virus derived vaccine antigens. An antibody fragment may be Fab, Fab', F(ab')2, Fd or scFv, which is capable of binding to a specific antigen, and preferably Fab'. The Fab fragments contain the variable domain (VL) and constant domain (CL) of the light chain and the variable domain (VH) and the first constant domain (CH1) of the heavy chain. The Fab' fragments differ from the Fab fragments in terms of adding several amino acid residues including one or more cysteine residues from the hinge region to the carboxyl terminus of the CH1 domain. The Fd fragments comprise only the VH and CH1 domain, and the F(ab')2 fragments are produced as a pair of Fab' fragments by either disulfide bonding or a chemical reaction. The scFv (single-chain Fv) fragments comprise the VL and VH domains that are linked to each other by a peptide linker and thus are present in a single polypeptide chain.

In particular, preferred as biologically active molecules are those requiring frequent dosing upon administration to the body for therapy or prevention of diseases, which include human growth hormone, interferons (interferon-α, -β, -γ, etc.), granulocyte colony stimulating factor (G-CSF), erythropoietin (EPO), TFN receptor, p40, and antibody fragments. In addition, certain derivatives are included in the scope of the biologically active molecules of the present invention as long as they have function, structure, activity or stability substantially identical to or improved compared over native forms of the biologically active molecules. In the present invention, the most preferable polypeptide drug is interferon-alpha.

In another aspect of the invention, IgG-Fc and IgG-CH fusion proteins, for example, are synthesized as monomers that can assemble to form dimers. Typically, the dimers are joined by disulfide bonds in the IgG Hinge region. Conditioned media from cells secreting the IgG fusion proteins can contain mixtures of IgG fusion protein monomers and dimers. For use as human therapeutics it will be desirable to use homogeneous populations of either IgG fusion protein monomers or dimers, but not mixtures of the two forms.

Methods for obtaining essentially pure preparations of dimeric active polypeptide-IgG fusion proteins are also provided. The methods are generally accomplished by obtaining a host cell capable of expressing the IgG fusion protein, collecting the conditioned media, and purifying the dimeric fusion protein from monomeric fusion protein, aggregates and contaminating proteins by column chromatography procedures. Suitable host cells for expressing the IgG fusion proteins include yeast, insect, mammalian or other eukaryotic cells. In an embodiment, the host cell may be a mammalian cell, particularly COS, CHO or BHK cells.

Novel fusion proteins of a polypeptide drug and a Fc fragment are also provided. In one embodiment, a polypeptide drug such as EPO, p40, G-CSF or TNF receptor is joined directly to the hybrid Fc fragment without an intervening peptide linker. In another embodiment, the polypeptide drug is joined to each other through a peptide linker of 1 to 50 amino acids, and more preferably through a peptide linker of 1 to 7 amino acids. Particularly useful linkers for this purpose include an immunologically inactive peptide composed of Gly and Ser residues (eg. Gly Gly Ser Gly Gly Ser Gly Gly Gly Gly Ser Gly Gly Gly Gly Ser; SEQ ID NO: 32) or composed of amino acids at positions 282-314 of SEQ ID NO: 25 derived in human albumin.

In the case when a linker is used, the linker and a polypeptide drug may be made in a certain direction. That is, the linker may be linked to the N-terminus, the C-terminus or a free group of the hybrid Fc fragment, and may also be linked to the N-terminus, the C-terminus or a free group of the polypeptide drug. When the linker is a peptide linker, the linkage may take place at a certain linking site.

When a polypeptide drug and a hybrid Fc is expressed separately and then joined to each other, the coupling may be performed using any of a number of coupling agents known in the art. Non-limiting examples of the coupling agents include 1,1-bis(diazoacetyl)-2-phenylethane, glutaradehyde, N-hydroxysuccinimide esters such as esters with 4-azidosalicylic acid, imidoesters including disuccinimidyl esters such as 3,3'-dithiobis (succinimidylpropionate), and bifunctional maleimides such as bis-N-maleimido-1,8-octane.

The present invention also provides methods for the production of polypeptide drug-hybrid Fc fragment.

The present invention also provides methods for treating conditions alleviated by the administration of a polypeptide drug. These methods include administering to a mammal having the condition, which may or may not be directly related to a disease of interest, an effective amount of a polypeptide of the invention. For example, a nucleic acid, such as DNA or RNA, encoding a desired polypeptide drug-hybrid Fc fragment fusion protein can be administered to a subject, preferably a mammal, as a therapeutic agent. Additionally, a cell containing a nucleic acid encoding a polypeptide drug-hybrid Fc fragment fusion protein can be administered to a subject, preferably a mammal, as a therapeutic agent. Furthermore, a polypeptide drug-hybrid Fc fragment fusion construct can be administered to a subject, preferably a mammal, as a therapeutic agent. Such chimeric polypeptide may be administered intravenously, subcutaneously, orally, buccally, sublingually, nasally, parenterally, rectally, vaginally or via a pulmonary route.

An EPO (including its variants/fragments)-fc fusion protein of the present invention may be useful in raising and maintaining hematocrit in a mammal.

p40 is a subunit of IL-12. IL-12 is a 75 kDa heterodimeric cytokine that has several functions in vivo. For example, IL-12 stimulates proliferation of activated T and NK cells and promotes Th1-type helper cell responses. IL-12 exerts its biological effects by binding to the IL-12 receptor on the plasma membrane of activated T and NK cells, and the ability of IL-12 to bind to the IL-12 receptor has been attributed to the p40 subunit of IL-12. Therefore, a p40 (including its variants/fragments)-fc fusion protein of the present invention may be useful in reducing the symptoms of/preventing/treating an autoimmune disease, (ii) inhibiting rejection of a graft, or (iii) treating/preventing endotoxin-induced shock. Also, a p40 (including its variants/fragments)-fc fusion protein of the present invention may be useful in treating/preventing/amelioration the symptoms of rheumatoid arthritis, ankylosing spondylitis, inflammatory bowel disease, multiple sclerosis or psoriasis. Variants and fragments are known in the art, including, not limited to, WO 97/20062, contents of which are incorporated herein as reference. One embodiment of p40 variant includes, but is not limited to, p40 containing Asn303Gln substitution.

Granulocyte colony stimulating factor (G-CSF) is a protein that is essential for the proliferation and differentiation of granulocytes, particularly neutrophils. Granulocytes engulf and devour microbial invaders and cell debris and thus are crucial to infection response. Chemotherapy destroys granulocytes and/or decrease the production of granulocytes. Therefore, a G-CSF (including its variants/fragments)-fc fusion protein of the present invention may be useful in treating/preventing/amelioration the symptoms of chemotherapy-induced neutropenia myelosuppression after bone marrow transplantation, acute leukemia, aplastic anemia, myelodysplastic syndrome, severe chronic neutropenias, or mobilization of peripheral blood progenitor cells for transplantation.

The fusion proteins of the invention not only are useful as therapeutic agents, but one skilled in the art recognizes that the fusion proteins are useful in the production of antibodies for diagnostic use. Likewise, appropriate administration of the DNA or RNA, e.g., in a vector or other delivery system for such uses, is included in methods of use of the invention.

Compositions of the present invention may be administered by any route which is compatible with the particular molecules. It is contemplated that the compositions of the present invention may be provided to an animal by any suitable means, directly (e.g., locally, as by injection, implantation or topical administration to a tissue locus) or systemically (e.g., parenterally or orally). Where the composition is to be provided parenterally, such as by intravenous, subcutaneous, ophthalmic, intraperitoneal, intramuscular, buccal, rectal, vaginal, intraorbital, intracerebral, intracranial, intraspinal, intraventricular, intrathecal, intracisternal, intracapsular, intranasal or by aerosol administration, the composition preferably includes part of an aqueous or physiologically compatible fluid suspension or solution. Thus, the carrier or vehicle is physiologically acceptable so that in addition to delivery of the desired composition to the patient, it does not otherwise adversely affect the patient's electrolyte and/or volume balance. The fluid medium for the agent thus can include normal physiologic saline.

The DNA constructs (or gene constructs) of the invention also can be used as a part of a gene therapy protocol to deliver nucleic acids encoding a polypeptide drug or a fusion protein construct thereof.

The invention features expression vectors for in vivo transfection and expression of a polypeptide drug of interest or a fusion protein construct thereof in particular cell types so as to reconstitute or supplement the function of the desired polypeptide drug. Expression constructs of the desired polypeptide drug, or fusion protein constructs thereof, may be administered in any biologically effective carrier, e.g. any formulation or composition capable of effectively delivering the desired polypeptide drug-encoding gene or fusion protein construct thereof to cells in vivo.

Approaches include insertion of the subject gene in viral vectors including recombinant retroviruses, adenovirus, adeno-associated virus, and herpes simplex virus-1, or recombinant bacterial or eukaryotic plasmids. Preferred dosages per administration of nucleic acids encoding the fusion proteins of the invention are within the range of 0.1 mg-100 mg for humans, more preferably 1 mg-10 mg, and most preferably 2 mg-10 mg. It is contemplated that the optimal dosage and mode of administration may be determined by routine experimentation well within the level of skill in the art.

Preferred dosages of the fusion protein per administration are within the range of 0.1 mg-1,000 mg for humans, more preferably, 1 mg-100 mg and most preferably 5 mg-20 mg. It is contemplated that the optimal dosage, however, also depends upon the disease being treated and upon the existence of side effects. However, optimal dosages may be determined using routine experimentation. Administration of the fusion protein may be by periodic bolus injections, or by continuous intravenous, subcutaneous, or intraperitoneal administration from an external reservoir (for example, from an intravenous bag) or internal (for example, from a bioerodable implant).

Furthermore, it is contemplated that the fusion proteins of the invention also may be administered to the intended recipient together with a plurality of different biologically active molecules. It is contemplated, however, that the optimal combination of fusion protein and other molecules, modes of administration, dosages may be determined by routine experimentation well within the level of skill in the art.

The invention is illustrated further by the following non-limiting examples.

Example 1

Preparation of Expression Vectors for hFc-1, hFc-2, hFc-3, hFc-4, hFc-5, and hFc-6 Fusion Proteins The hFc-1 includes 9 amino acids (90-98) of C-terminal IgG1 CH1 region, hinge region (99-113) of IgG1, 6 amino acids (111-116) of N-terminal IgG2 CH2 region, 103 amino acids (118-220) of IgG4 CH2 region, and 107 amino acids (221-327) of IgG4 CH3 region (FIGS. 1 and 2). An amino acid sequence of hFc-1 is shown in SEQ ID NO: 18. To obtain codon-optimized nucleotides each coding for hFc-1 (SEQ ID NO: 1), human EPO (SEQ ID NO: 7), human G-CSF (SEQ ID NO: 8) and human p40N303Q (a mutant derived from substitution of Asn with Gln at the 303rd amino acid of human p40 subunit) (a nucleotide sequence of p40N303Q is shown as SEQ ID NO: 9, and an amino acid sequence of human p40 is shown as SEQ ID NO: 17), respectively, these nucleotide molecules were synthesized by custom service of TOP Gene Technologies (Quebec, Canada) (www.topgenetech.com). To increase the level of protein expression, it is very helpful to optimize codon usage of the gene. The pattern of codon usage differs between organisms. Some codons are used more frequently in one organism but used rarely in another organism. This bias in codon usage has been attributed to translational efficiency, the ability of the organism to synthesize the encoded protein. To insert each fusion gene to an expression vector, pAD11 (SEQ ID NO: 10), a EcoR I site was generated at 5' end of ATG sequence of EPO, G-CSF, and p40N303Q and Xba I site was generated at 3' end of the termination codon of hFc-1. The expression vector pAD11 was obtained from RcCMV backbone (available from Invitrogen, Carlsbad). pAD11, includes a promoter derived from cytomegalovirus (CMV), poly (A) sequences derived from bovine growth hormone, globin intervening sequence (gIVS) derived from rabbit beta globin (Mol Cell Biol, 1988 8: 4395) and etc. To make the pAD11 vector, there are several modifications from the RcCMV vector (Invitrogen). A neomycin resistant region was removed by treatment with Xho I enzyme and gIVS was added at 3' of CMV promoter region. In addition, a mouse dihydrofolate reductase (DHFR) gene (Pubmed, N.M. 010049) was added at 5' of CMV promoter. The pAD11 vector was developed after many expression tests in combination with several elements including them described above. In our unpublished result, pAD11 vector showed about 12-fold increase in expression level, compared to RcCMV vector (Invitrogen). To make a junction site between 3' end of EPO, G-CSF and p40N303Q and 5' end of hFc-1 in frame, a Nhe I site at 3' end of the coding sequence of EPO, G-CSF and p40N303Q and at 5' end of the coding sequence of hFc-1 was generated. After subcloning using each restriction enzymes site, the final expression vectors for hFc-1 fused with EPO, G-CSF or p40N303Q were generated, and then designated as pAD11 EPO-hFc-1, pAD11 G-CSF-hFc-1 and pAD11 p40N303Q-hFc-1, respectively.

Amino acid sequences of hFc-2, hFc-3, hFc-4, hFc-5 and hFc-6 are shown in SEQ ID NOs: 19-23, respectively. The hFc-6 includes 9 amino acids (90-98) of the C-terminal IgD CH1 domain, 64 amino acids of the hinge region (99-162) of IgD, 8 amino acids (SHTQPLGV; 163-170) of the N-terminal IgD CH2 domain, 100 amino acids (121-220) of the IgG4 CH2 domain, and 107 amino acids (221-327) of the IgG4 CH3 domain (FIGS. 1 and 2). To obtain codon-optimized nucleotide molecule coding for hFc-6 (SEQ ID NO: 6), the gene was synthesized by custom service of TOP Gene Technologies (www.topgenetech.com). To make a fusion between 3' end of EPO, G-CSF, or p40N303Q and the 5' end of hFc-6 in frame, the Nhe I site (gctagc: Ala-Ser) included in the N-terminal coding region (90 and 91 amino acids) of hFc-6 was used. Also, to insert each hFc-6 fusion gene into pAD11 vector, a Xba I site was generated at the 3' end of hFc-6 gene. After subcloning using each restriction enzymes site, the final expression vectors for hFc-6 fused EPO, G-CSF and p40N303Q were generated, and then designated as pAD11 EPO-hFc-6, pAD11 G-CSF-hFc-6 and pAD11 p40N303Q-hFc-6, respectively. The hFc-2, hFc-3, hFc-4, and hFc-5 have identical CH2 and CH3 regions, but they have different sizes of IgD hinge (FIGS. 1 and 2). The hFc-2 (SEQ ID NO: 19), hFc-3 (SEQ ID NO: 20), hFc-4 (SEQ ID NO: 21), and hFc-5 (SEQ ID NO: 22) includes 5 amino acids (158-162), 10 amino acids (153-162), 20 amino acids (143-162), 30 amino acids (133-162) of C-terminal IgD hinge, respectively (FIGS. 1 and 2). To make the fusion genes between EPO, G-CSF, p40N303Q or TNFR (tumor necrosis factor receptor II) (SEQ ID NO: 30) and nucleic acid molecules coding for these hFcs (SEQ ID NOs: 2-5), the minimal gene fragments in total size of the fused genes were synthesized by custom service of TOP Gene Technologies (www.topgenetech.com). The synthesized fragments of each EPO, G-CSF, p40N303Q or TNFR fused with a nucleotide molecule coding for hinge and N-terminal CH2 region of each hFc-2, hFc-3, hFc-4, or hFc-5 include the sequences ranged from the entire EPO, G-CSF, p40N303Q or TNFR sequences to the identical enzyme site, BstE TI site (GGTGACC) that is located at 138-140$^{th}$ amino acid residues of CH2 region in IgG4 (SEQ ID NO: 13). The subcloning vectors including several gene fragments were cut with EcoR I and BstE II located at 5' end and 3' end, respectively, and then ligated to the CH2-CH3 region of the hFc-6. Finally, the each fusion gene was subcloned to the pAD11 using EcoR I and Xba I sites, and then designated as pAD11 EPO-hFc-2, pAD11 EPO-hFc-3, pAD11 EPO-hFc-4, pAD11 EPO-hFc-5, pAD11 G-CSF-hFc-2, pAD11 G-CSF-hFc-3, pAD11 G-CSF-hFc-4, pAD11 G-CSF-hFc-5, pAD11 p40N303Q-hFc-2, pAD11 p40N303Q-hFc-3, pAD11 p40N303Q-hFc-4, pAD11 p40N303Q-hFc-5 and pAD11 TNFR-hFc-5, respectively.

Example 2

Preparation of Expression Vectors for thFc-1 and thFc-2 Coupled to IFN-β

The thFc-1 includes 23 amino acids (MDAMLRGLCCV-LLLCGAVFVSPS) of signal sequence of human tissue plasminogen activator (tPA), 15 amino acids (99-113) of IgG1 hinge region, 6 amino acids (111-116) of N-terminal IgG2 CH2 region, 103 amino acids (118-220) of IgG4 CH2 region, and 107 amino acids (221-327) of IgG4 CH3 region (FIG. 3). An amino acid sequence of thFc-1 is shown in SEQ ID NO: 28. The thFc-2 includes 23 amino acids (MDAMLRGLCCV-LLLCGAVFVSPS) of tPA signal sequence, 15 amino acids (148-162) of IgD hinge region, 8 amino acids (163-170) of N-terminal IgD CH2 region, 100 amino acids (121-220) of IgG4 CH2 region, and 107 amino acids (221-327) of IgG4 CH3 region (FIG. 3). An amino acid sequence of thFc-2 is shown in SEQ ID NO: 29. To obtain codon-optimized nucleotides coding for thFc-1 (SEQ ID NO: 26) or thFc-2 (SEQ ID NO: 27) coupled to the N-terminus of human IFN-beta deleted its signal sequence, these nucleotide molecules were synthesized by custom service of TOP Gene Technologies (Quebec, Canada) (www.topgenetech.com). To insert each fusion gene to an expression vector, pAD11 (SEQ ID NO: 10), a EcoR I site was generated at 5' end of thFc-1 or thFc-2 and Not I site was generated at 3' end of the termination codon of IFN-beta. After subcloning using each restriction enzymes site, the final expression vectors were designated as pAD11 thFc-1-AL(0)-IFN-beta and pAD11 thFc-2-AL(0)-IFN-beta, respectively.

To make thFc coupled to IFN-beta via different sizes of albumin linkers or Gly-Ser linker, the gene fragments ranged from Pst I site of CH3 region of thFc-1 coupled to IFN-beta deleted its signal sequence via different sizes of albumin linkers (3aa, 8aa, 13aa, 18aa, 23aa and 33aa) or Gly-Ser linker (15aa) were synthesized by custom service of TOP Gene Technologies (www.topgenetech.com) (FIG. 4). To insert 7 different gene fragments to expression vectors, pAD11 thFc-1-AL(0)-IFN-beta and pAD11 thFc-2-AL(0)-IFN-beta, a Pst I site was generated at 5' end of them and Not I site was generated at 3' end of the termination codon of IFN-beta. After subcloning using each restriction enzymes site, the final expression vectors were designated as pAD11 thFc-1-AL(1)-IFN-beta, pAD11 thFc-1-AL(2)-IFN-beta, pAD11 thFc-1-AL(3)-IFN-beta, pAD11 thFc-1-AL(4)-IFN-beta, pAD11 thFc-1-AL(5)-IFN-beta, pAD11 thFc-1-AL(6)-IFN-beta pAD11, thFc-1-GS-IFN-beta, pAD11 thFc-2-AL(1)-IFN-beta, pAD11 thFc-2-AL(2)-IFN-beta, pAD11 thFc-2-AL(3)-IFN-beta, pAD11 thFc-2-AL(4)-IFN-beta, pAD11 thFc-2-AL(5)-IFN-beta, pAD11 thFc-2-AL(6)-IFN-beta pAD11, and thFc-2-GS-IFN-beta.

Example 3

Expression of Human EPO-hFcs, Human G-CSF-hFcs, Human p40N303Q-hFcs, Human TNFR-hFc-5 and thFcs-IFN-beta Proteins COS-7 cells were used for expression test and cultured with DMEM media (Invitrogen, Carlsbad) supplemented with 10% fetal bovine serum (Hyclone, South Logan) and antibiotics (Invitrogen, Carlsbad). The vectors encoding EPO-hFcs, G-CSF-hFcs, p40N303Q-hFcs, TNFR-hFc-5, thFcs-IFN-beta were transfected to 5×10$^6$ COS-7 cells using conventional electroporation methods. At 48 h after transfection, supernatants and cells were harvested. To check the expression of fusion protein from each vector, all the samples were used for ELISA assay with several kits (R&D system, Minneapolis, #DEP00 for EPO; Biosource, Camarillo, #KHC2032, for G-CSF; R&D system, Minneapolis, #DY1240 for p40N303Q; R&D system, Minneapolis, #DRT200 for TNFR, PBL Biomedical Laboratories, #41410-1A for IFN-beta) and western blot analysis with anti-human IgG antibodies (Santa Cruz Biotechnology, Santa Cruz). As a result, all the vectors showed correct expression pattern in the supernatants and cell lysates (data not shown).

Example 4

Purification of hFc-Fused Proteins

The CHO/DHFR$^{-/-}$ cells (chinese hamster ovary cells, DG44, ATCC) were cultured with α-MEM (Invitrogen, Carlsbad), 10% dialyzed fetal bovine serum (JRH Biosciences, Kansas), HT supplement (Invitrogen, Carlsbad) and antibiotics (Invitrogen, Carlsbad). The expression vectors were transfected to the CHO cells according to the conventional CaPO$_4$ coprecipitation methods. At 48 h after transfection, the CHO cells were detached from the plates and diluted at several folds (½, ⅕, 1/20, 1/50, 1/100, 1/200, 1/500). The diluted cells were plated to 100 mm dishes and cultured with the media without HT supplement. During screening process, the fresh media without HT supplement were supplied to the cells without passage. The colonies were generated for 2-3 weeks after plating and the individual colonies were moved to 48 well plates. The positive colonies were screened after ELISA assay for EPO, G-CSF, p40N303Q, and TNFR detections. Each colony that showed the highest expression was cultured in a large scale (5 L) using serum free media (JRH Biosciences, Kansas). The serum-free supernatants harvested were used for purification of each fusion protein. For purification, HiTrap recombinant protein A FF (Amersham biosciences, Piscataway) columns were equilibrated with 20 mM Sodium phosphate (pH 7.0). The filtered supernatants were added to the columns and eluted with 0.1M sodium citrate (pH 3.0). The eluted proteins were finally obtained after dialysis with membrane (MWCO 12-14K, Spectrapor, Rancho Dominguez) more than three times. All the concentration of protein samples was determined by BCA kit (Pierce Biotechnology, Rockford) for the measurement of the total protein and by ELISA kits for the measurement of EPO-hFcs, G-CSF-hFcs, p40N303Q-hFcs, TNFR-hFc-5 and thFcs-IFN-beta.

Example 5

FcγRI and C1q Binding Assay

Figure 6A:
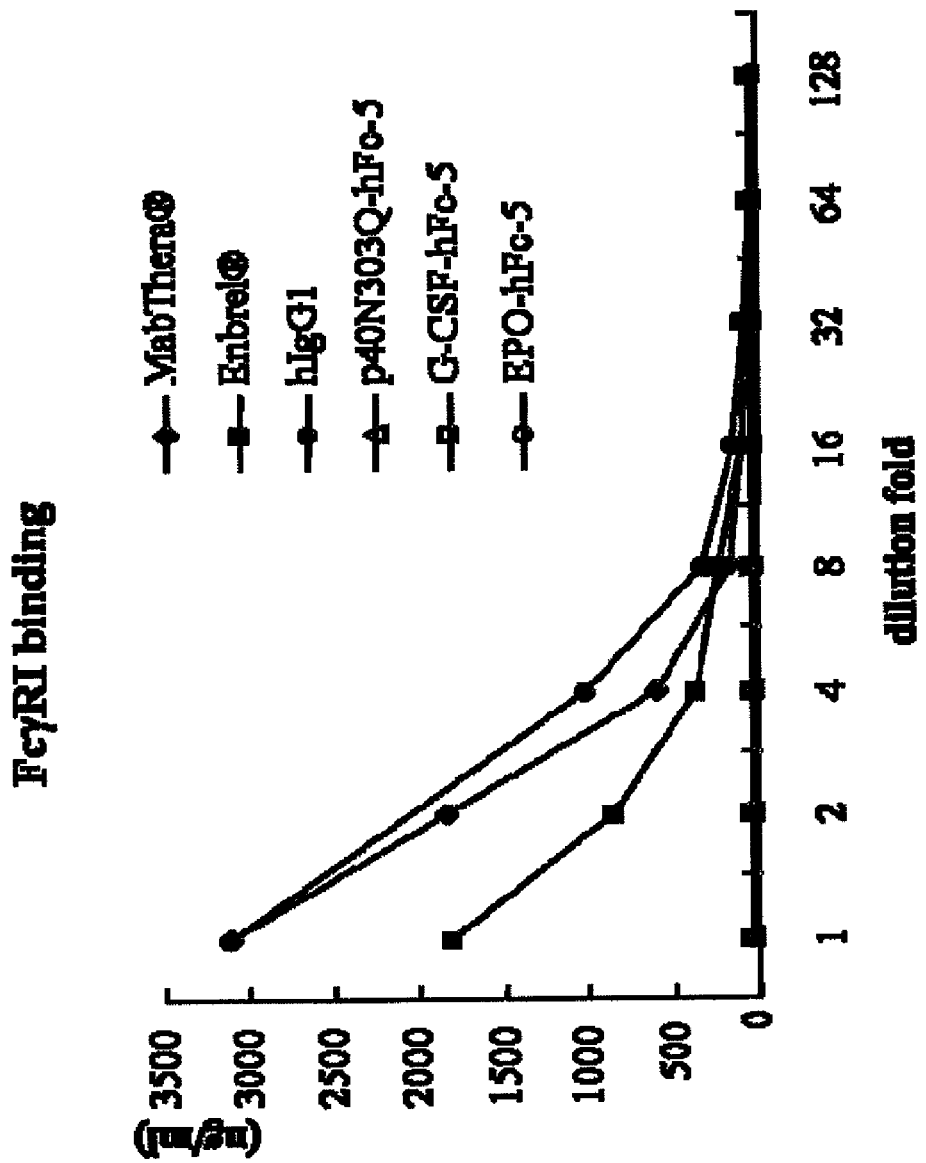
FIG. 6(a) shows the results of FcγR1 binding activities of MabThera® (Rituximab), hIgG1, Enbrel® (etanercept), EPO-hFc-5, G-CSF-hFc-5, p40N303Q-hFc-5 using specific ELISA assay.
Figure 6B:
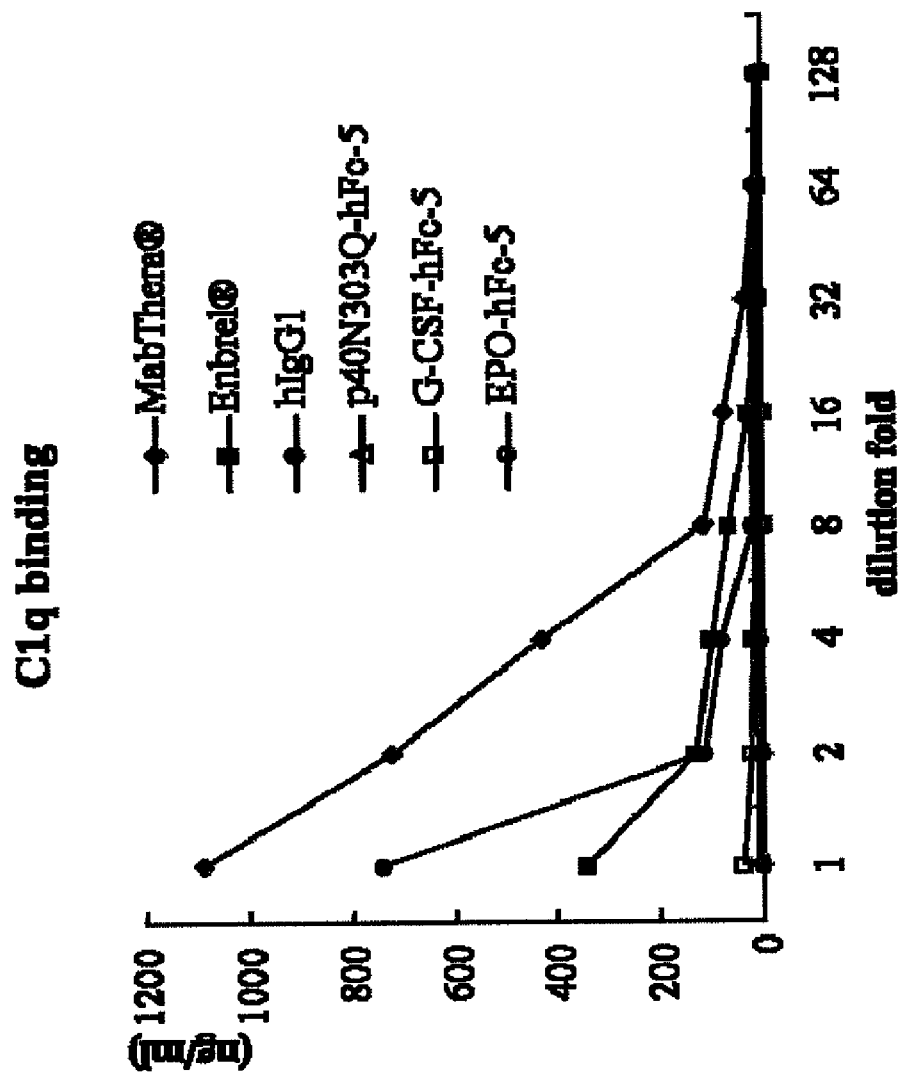
FIG. 6(b) shows the results of C1q binding activities of MabThera® (Rituximab), hIgG1, Enbrel® (etanercept), EPO-hFc-5, G-CSF-hFc-5, p40N303Q-hFc-5 using specific ELISA assay.

To investigate whether hFc-5-fused proteins bind to FcγRI and C1q, MabThera® (Rituximab, Roche), hIgG1 (Calbiochem, Cat#, 400120), Enbrel® (etanercept, Amgen), EPO-hFc-5, G-CSF-hFc-5 and p40N303Q-hFc-5 were serially diluted (from 2 ug/ml to 16 ng/ml with 2-fold) and coated on the 8 well strip (COSTAR, New York) overnight at 4° C. To make a standard curve, FcγRI (R&D, cat# BAF1257) or C1q (AbD serotech, Cat#. 2221-5504) were also serially diluted (from 2 ug/ml to 32 ng/ml with 2-fold) and coated on the 8 well strip (COSTAR, New York) overnight at 4° C. After washing each strip of samples with washing buffer (PBS containing 0.05% tween) and blocking with 10% FBS in PBS for 1 hour at RT, FcγRI or C1q were added into each well at 2 ug/ml following incubation for 2 hours at room temperature (RT). All strips were washed with washing buffer. For C1q binding test, HRP conjugated anti-C1q (AbD serotech, cat#. 2221-5004P) was added into each well at 2.5 ug/ml following 30 min incubation at RT under dark condition. For FcγRI binding test, biotinylated anti-FcγRI (R&D, cat#. 1257-FC) was added into each well at 2 ug/ml following 1 hour incubation at RT. After washing them with washing buffer, Streptavidine-HRP (BD, cat#. 554066) diluted with 3,000 fold was added into each strip following 30 minute incubation at RT under dark condition. After washing the strips, TMB solution (1:1 mixture of TMB Peroxidase substrate and Peroxidase substrate solution B, KPL, cat#. 50-76-01, cat#, 50-65-00) was added for development and 2N $H_2SO_4$ was added for stopping development. As shown in FIG. 6(a) and FIG. 6(b), MabThera®, Enbrel® and hIgG1 were shown to be well bound to FcγRI and C1q, but EPO-hFc-5, G-CSF-hFc-5 and p40N303Q-hFc-5 were not.

Example 6

In Vitro Bioactivity of Purified hFc-Fused Proteins

To investigate the in vitro bioactivities of EPO-hFc proteins, human F35E cell line was cultured in RPM11640 media (Cambrex, Charles City) supplemented with 10% FBS, antibiotics and 5 IU/ml recombinant human EPO (DongA, Republic of Korea). Bioassays were set up by seeding $2 \times 10^4$ cells to test wells of a 96-well cell culture plate (Corning, Netherlands). The samples with serial dilutions (0, 0.064 mIU/ml to 25 IU/ml with 5-fold) of EPO, EPO-hFc-1, EPO-hFc-5, EPO-hFc-6, EPO-IgG1 Fc or Aranesp® (darbepoetin alfa, Amgen) were added to the these wells and the plates were incubated at 37° C. for 72 hours in a humidified 5% $CO_2$ incubator. According to the manufacturer's protocol, MTT assay was performed by using cell growth colorimetric assay kit (Sigma-Aldrich. Korea). The human F35E cell line showed a strong proliferative response to rEPO, as evidenced by a dose-dependent manner in cell number and absorbance values. As shown in FIG. 7(a), Aranesp® and EPO proteins coupled to IgG1 Fc or hFcs showed loss of biological activity, compared to EPO protein. However, EPO-hFc-1, EPO-hFc-5 and EPO-hFc-6 showed significantly higher bioactivity than EPO-IgG1 Fc. In addition, EPO-hFc-5 and EPO-hFc-6 showed slightly higher bioactivity than Aranesp®, indicating that these hFc-fused proteins appear to be better than Aranesp® in terms of maintaining bioactivity of EPO protein.

To investigate the in vitro bioactivities of G-CSF-hFc protein, mouse hematopoietic cell line, NFS-60 was cultured in RPM11640 media (Cambrex, Charles City) supplemented with 10% FBS, antibiotics and 100 units/ml recombinant mouse IL-3 (R&D system, Minneapolis). Bioassays were set up by seeding $2 \times 10^4$ cells to wells of a 96-well cell culture plate (Corning, Netherlands). The samples with serial dilutions (ranged from 0 to 10,000 pg/ml with 3-fold) of G-CSF-hFc-5 and Neulasta® (pegfilgrastim, Amgen) were added to these wells and the plates were incubated at 37° C. for 72 hours in a humidified 5% $CO_2$ incubator. Protein samples were assayed in triplicate wells and this experiment was performed repeatedly for five times. At 72 hours after incubation, MTT assay was performed by using cell growth colorimetric assay kit (Sigma-Aldrich. Korea), according to the manufacturer's protocol. As illustrated in FIG. 7(b), G-CSF-hFc-5 showed slightly higher in vitro bioactivity than Neulasta®.

To investigate the in vitro bioactivity of p40N303Q-hFc protein, peripheral blood mononuclear cells (PBMCs) of rheumatoid arthritis patients were incubated with 2 ug/ml of anti-human CD3 antibody (R&D system, # MAB 100) with or without 10 ng/ml of human p40 (R&D system) or p40N303Q-hFc-5 in RPM11640 media (Cambrex, Charles City) supplemented with 10% FBS, and antibiotics. After day 6, the cells positive for CD4 and IL-17 were measured by FACS analysis. As shown in FIG. 7(c), p40N303Q-hFc-5 showed stronger suppressive effect on the generation of $CD4^+/IL-17^-$ cells than p40 protein, indicating the inhibitory function of p40N303Q-hFc-5 on Th17 polarization.

To investigate the in vitro bioactivity of TNFR-hFc protein, murine L929 cells were cultured in RPM11640 media (Cambrex, Charles City) supplemented with 10% FBS and antibiotics. Cytopathic inhibition assay was set up by seeding $3 \times 10^4$ cells to wells of a 96-well cell culture plate (Corning, Netherlands), then treated with 1 ng/ml of TNF-α. The samples with serial dilutions (ranged from 15.6 to 1,000 ng/ml with 2-fold) of TNFR-hFc-5 and Enbrel® (etanercept, Amgen) were added to these wells and the plates were incubated at 37° C. for 48 hours in a humidified 5% $CO_2$ incubator. After incubation, MTT assay was performed by using cell growth colorimetric assay kit (Sigma-Aldrich, Korea), according to the manufacturer's protocol. As illustrated in FIG. 7(d), TNFR-hFc-5 showed slightly higher in vitro bioactivity than Enbrel®.

To investigate the in vitro bioactivities of thFc-1-AL(0)-IFN-beta and thFc-1-AL(3)-IFN-beta proteins, WISH cells (ATCC, CCL-25) were cultured in DMEM/F12 (Cambrex, Charles City) supplemented with 10% FBS and antibiotics. Cytopathic inhibition assay was set up by seeding $3 \times 10^4$ cells to wells of a 96-well cell culture plate (Corning, Netherlands), then treated with 1,500 PFU/well of VSV (ATCC, VR-158). The samples with serial dilutions (from 40 IU/ml with 2-fold) of recombinant IFN-beta (WHO standard, NIBSC 00/572), thFc-1-AL(0)-IFN-beta and thFc-1-AL(3)-IFN-beta proteins were added to these wells and the plates were incubated at 37° C. for 48 hours in a humidified 5% $CO_2$ incubator. After incubation, MTT assay was performed by using cell growth colorimetric assay kit (Sigma-Aldrich. Korea), according to the manufacturer's protocol. As illustrated in FIG. 7(e), thFc-1-AL(3)-IFN-beta showed about 20 fold higher in vitro bioactivity than thFc-1-AL(0)-IFN-beta, indicating the important role of albumin liker to maintain the bioactivity of IFN-beta fused to Fc.

Example 7

In Vivo Half Life of Purified hFc-Fused Proteins

To compare the half life of EPO-hFc-1, EPO-hFc-5 and Aranesp®, fifteen cynomolgus monkeys were treated with these proteins in a dose of 2,400 IU/kg via single subcutaneous (SC) injection or a single intravenous (IV) injection. Blood samples of each monkey were obtained before injection and at 1, 3, 6, 12, 24, 30, 48, 54, 72, 78, 96, 120, 168, 336, 504, and 672 h post-injection. Blood samples were incubated at room temperature for 30 min to be clotted. After centrifugation at 3000 rpm for 10 min, sera from each sample were obtained and stored at deep freezer. All samples obtained at each point were tested for the quantification of EPO by EPO ELISA kit (R&D, cat #. DEP00). As shown in FIG. 8(a), all individual monkeys injected with EPO-hFc-1 or EPO-hFc-5 via SC or IV routes showed longer half life than individual monkeys injected with Aranesp® via SC or IV routes.

To investigate the pharmacokinetics of G-CSF-hFc-1, 100 ug/kg of LEUCOSTIM® (filgrastim, DongA, Republic of Korea) as a control and G-CSF-hFc-1 were administrated via SC or IV routes to two male Sprague Dawley Rats (Charles River Laboratories, Wilmington) per group. Blood was obtained before injection and 1, 2, 3, 4, 8, 12, 24, 48, 72, 96, 120 and 192 h post-injection. Sera obtained by centrifugation at 3,000 rpm for 10 min after incubation at room temperature for 30 min and stored at deep freezer. Samples were quantified with several dilution folds such as ½, ⅕, 1/50, 1/250, 1/500 using G-CSF kit (Biosource, Camarillo, #KHC2032). As shown in FIG. 8(b), G-CSF-hFc-1 injected via SC or IV routes showed longer half-life than LEUCOSTIM®. G-CSF-hFc-1 and G-CSF had 8.76 h and 2.36 h of in vivo $t_{1/2}$ after SC administration and 10.42 h and 1.78 h after IV administration, respectively. Therefore, G-CSF-hFc-1 showed an enhancement of 3.7-fold following SC injections and 5.9-fold following IV injection, compared to the LEUCOSTIM®.

To investigate the pharmacokinetics of p40N303Q-hFc-5 and Enbrel®, three cynomolgus monkeys per group were treated with a single SC injection in a dose of 100 ug/kg. Blood samples of each monkey were obtained before injection and at 8, 24, 48, 72, 96, 120, 168, 336, 504, and 672 h post-injection. Blood samples were incubated at room temperature for 30 min to be clotted. After centrifugation at 3000 rpm for 10 min, sera from each sample were obtained and stored at deep freezer. All samples obtained at each point were tested for the quantification of human p40 and human TNFR TI by ELISA kits (R&D system, Minneapolis, #DY1240 and #DRT200, respectively). As shown in FIG. 8(c), p40N303Q-hFc-5 showed longer half life than Enbrel® (average 199 h vs 127 h), although p40N303Q-hFc-5 showed lower Cmax value than Enbrel® (average 3 ng/ml vs 7 ng/ml).

To investigate the pharmacokinetics of TNFR-hFc-5 and Enbrel®, three male Sprague Dawley Rats (Charles River Laboratories, Wilmington) per group were treated with a single SC injection in a dose of 500 ug/kg. Blood samples of each rat were obtained before injection and at 2, 4, 8, 12, 24, 30, 48, 72 and 120 h post-injection. Blood samples were incubated at room temperature for 30 min to be clotted. After centrifugation at 3,000 rpm for 10 min, sera from each sample were obtained and stored at deep freezer. All samples obtained at each point were tested for the quantification of human TNFR TI by ELISA kits (R&D system, Minneapolis, #DRT200). As shown in FIG. 8(d), TNFR-hFc-5 showed slightly higher AUC level than Enbrel® (average 198.1 vs 172.9 ug*h/ml), although TNFR-hFc-5 showed similar half life to Enbrel®(average 28.6 h vs 29.4 h).

Example 8

In Vivo Bioactivity of Purified hFc-Fused Proteins

To compare the in vivo bioactivity of EPO-hFc-5 and Aranesp®, three cynomolgus monkeys per group were treated with a SC injection or a single IV injection in a dose of 2,400 IU/kg. Blood samples of each monkey were obtained before injection and at 1, 3, 6, 12, 24, 30, 48, 54, 72, 78, 96, 120, 168, 336, 504, and 672 h post-injection. The number of various blood cells including reticulocytes was measured to evaluate the in vivo bioactivity of EPO-hFc-5 and Aranesp®. As shown in FIG. 9(a), EPO-hFc-5 showed slightly higher in vitro potency than Aranesp® in both SC and IV routes in terms of increase of reticulocytes in monkeys.

To investigate the in vivo bioactivity of G-CSF-hFc-1, LEUCOSTIM® (filgrastim, DongA, Republic of Korea) as a control and G-CSF-hFc-1 in a dose of 100 ug/kg were administrated via SC or IV routes to two male Sprague Dawley Rats (Charles River Laboratories, Wilmington) per group. Blood was obtained using EDTA tube before injection and 1, 2, 3, 4, 8, 12, 24, 48, 72, 96, 120 and 192 h post-injection. Each blood sample was treated with RBC lysis buffer (BD Bioscience, Korea) for 4 minutes and total WBCs (white blood cells) diluted in FACS buffer were counted repeatedly three times using hematocytometer. The number of granulocyte was measured using FACS caliber by determination of cell size by FSC (forward scatter) and granules by SSC (side scatter). As illustrated in FIG. 9(b), LEUCOSTIM® treated via SC and IV routes induced the peak number of WBC and granulocyte at 24 hours post-injection, while G-CFS-hFc-1 induced the peak number of WBC and granulocytes at 72 hours post-SC injection and 48 hours post-IV injection. From 24 h to 120 h after injection, G-CSF-hFc-1 had more sustained in vivo bioactivity, compared with LEUCOSTIM®.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A polypeptide represented by the following formula:

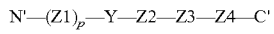

wherein N' is the N-terminus and C' is the C-terminus of the polypeptide,

Z1 is an amino acid sequence consisting of the amino acid residues at positions 90 to 98 of SEQ ID NO:14;

Y is an amino acid sequence consisting of 5 or more consecutive amino acid residues from the C-terminus at positions 99 to 162 of SEQ ID NO:14;

Z2 is an amino acid sequence consisting of the amino acid residues at positions 163 to 170 of SEQ ID NO:14;

Z3 is an amino acid sequence consisting of the amino acid residues at positions 121 to 220 of SEQ ID NO: 13;

Z4 is an amino acid sequence consisting of the amino acid residues at positions 221 to 327 of SEQ ID NO: 13; and p is an integer of 0 or 1.

2. The polypeptide of claim 1, wherein Y is amino acid residues at positions 158 to 162 of SEQ ID NO: 14, amino acid residues at positions 153 to 162 of SEQ ID NO: 14, amino acid residues at positions 143 to 162 of SEQ ID NO: 14, amino acid residues at positions 133 to 162 of SEQ ID NO: 14, or amino acid residues at positions 99 to 162 of SEQ ID NO: 14.

3. The polypeptide according to claim 1, wherein p is 0 (zero).

4. The polypeptide according to claim 1, wherein the polypeptide is encoded by a nucleotide sequence selected from the group consisting of SEQ ID NO: 1, SEQ ID NO: 2, SEQ ID NO: 3, SEQ ID NO: 4, SEQ ID NO: 5 and SEQ ID NO: 6, SEQ ID NO: 26 and SEQ ID NO: 27.

5. The polypeptide according to claim 1, wherein the polypeptide has an amino acid sequence selected from the group consisting of SEQ ID NO: 18, SEQ ID NO: 19, SEQ ID NO: 20, SEQ ID NO: 21, SEQ ID NO: 22 and SEQ ID NO: 23, SEQ ID NO: 28 and SEQ ID NO: 29.

6. The polypeptide according to claim 5, wherein the polypeptide has the amino acid sequence of SEQ ID NO: 18.

7. The polypeptide according to claim 5, wherein the polypeptide has the amino acid sequence of SEQ ID NO: 22.

8. The polypeptide according to claim 5, wherein the polypeptide has the amino acid sequence of SEQ ID NO: 23.

9. A chimeric polypeptide comprising the polypeptide of claim 1 and a biologically active molecule, wherein the biologically active molecule is fused at the N-terminus or the C-terminus of the polypeptide, and wherein said biologically active molecule shows an increased circulating half-life compared to the circulating half-life of the non-fused form of said biologically active molecule.

10. The chimeric polypeptide of claim 9, wherein the biologically active molecule is a hormone, cytokine, growth factor, co-stimulatory molecule, hormone receptor, cytokine receptor, growth factor receptor, or short peptide.

11. The chimeric polypeptide according to claim 9, wherein said biologically active molecule is EPO.

12. The chimeric polypeptide according to claim 9, wherein said biologically active molecule is p40 (SEQ ID NO: 17) or, TNF receptor.

13. The chimeric polypeptide according to claim 12, wherein said biologically active molecule is a variant of said p40 in which the variant consists of Asn303Gln substitution in the said p40.

14. The chimeric polypeptide according to claim 9, wherein said biologically active molecule is a G-CSF.

15. The chimeric polypeptide according to claim 9, wherein said biologically active molecule is a GM-CSF, IL-1, IL-2, IL-3, IL-4, IL-5, IL-6, IL-7, IL-8, human growth hormone, bone morphogenetic protein-1, interferon-alpha, IL-10, FSH, Factor VII, CTLA4, IFN-beta, PD-1, IL-10R, CXCL-11, TGF-beta receptor, TGF-beta, IL-17R, GLP-1, BTC, OPG, RANK.

16. The chimeric polypeptide according to claim 9, wherein said biologically active molecule is a secreted protein.

17. The chimeric polypeptide according to claim 16, wherein said biologically active molecule is a mature form of the secreted protein.

18. The chimeric polypeptide according to claim 9, wherein said biologically active molecule is a Fab region of an antibody.

19. The chimeric polypeptide according to claim 9, wherein said polypeptide and said biologically active molecule are coupled to each other via a linker, wherein the linker is an albumin linker or a synthetic linker.

20. The chimeric polypeptide of claim 19, wherein said albumin linker comprises amino acid sequence 321 to 323, 318 to 325, 316 to 328, 313 to 330, 311 to 333, or 306 to 338 of SEQ ID NO: 25.

21. The chimeric polypeptide of claim 19, wherein said synthetic linker is a peptide of 10 to 20 amino acid residues, wherein the peptide being composed of Gly and Ser residues.

22. A method of producing the polypeptide according to claim 1 or claim 9, wherein the method comprises the steps of: (i) introducing a nucleic acid molecule coding for the polypeptide into a mammalian host cell, (ii) growing the cell under conditions where the polypeptide can be expressed in its growth medium; and (iii) harvesting the expressed polypeptide.

23. An isolated nucleic acid molecule which encodes the polypeptide of claim 1 or the chimeric polypeptide according to claim 9.

24. The nucleic acid molecule according to claim 23, wherein said polypeptide has an amino acid sequence selected from the group consisting of SEQ ID NO: 18, SEQ ID NO: 19, SEQ ID NO: 20, SEQ ID NO: 21, SEQ ID NO: 22, SEQ ID NO: 23, SEQ ID NO: 28 and SEQ ID NO: 29.

25. The nucleic acid molecule according to claim 24, wherein the nucleic acid molecule is one selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 26 and SEQ ID NO: 27.

26. An expression vector comprising the nucleic acid molecule according to claim 23.

* * * * *